United States Patent
Kawada et al.

(10) Patent No.: US 10,032,993 B2
(45) Date of Patent: Jul. 24, 2018

(54) AROMATIC HETEROCYCLIC COMPOUND, MANUFACTURING METHOD THEREOF, ORGANIC SEMICONDUCTOR MATERIAL, AND ORGANIC SEMICONDUCTOR DEVICE

(71) Applicant: NIPPON STEEL & SUMIKIN CHEMICAL CO., LTD., Tokyo (JP)

(72) Inventors: Atsushi Kawada, Kitakyushu (JP); Takuo Nagahama, Kitakyushu (JP); Hiroyuki Hayashida, Kitakyushu (JP); Kouta Masutani, Kitakyushu (JP)

(73) Assignee: NIPPON STEEL & SUMIKIN CHEMICAL CO., LTD., Tokyo (JP)

( * ) Notice: Subject to any disclaimer, the term of this patent is extended or adjusted under 35 U.S.C. 154(b) by 310 days.

(21) Appl. No.: 14/780,609

(22) PCT Filed: Mar. 17, 2014

(86) PCT No.: PCT/JP2014/057166
§ 371 (c)(1),
(2) Date: Sep. 28, 2015

(87) PCT Pub. No.: WO2014/156773
PCT Pub. Date: Oct. 2, 2014

(65) Prior Publication Data
US 2016/0056390 A1    Feb. 25, 2016

(30) Foreign Application Priority Data
Mar. 29, 2013    (JP) ................... 2013-074538

(51) Int. Cl.
*H01L 51/00* (2006.01)
*C07D 491/048* (2006.01)
(Continued)

(52) U.S. Cl.
CPC ...... *H01L 51/0071* (2013.01); *C07D 491/048* (2013.01); *C07D 495/04* (2013.01);
(Continued)

(58) Field of Classification Search
CPC ............. H01L 51/0071; H01L 51/0068; H01L 51/0094; H01L 51/0073; H01L 51/42;
(Continued)

(56) References Cited

U.S. PATENT DOCUMENTS

2012/0273770 A1   11/2012   Sunagawa et al.
2014/0061616 A1    3/2014   Sunagawa et al.

FOREIGN PATENT DOCUMENTS

JP    2009-267134 A    11/2009
JP    2010-87408 A      4/2010
(Continued)

OTHER PUBLICATIONS

English Translation of JP2010087408.*
(Continued)

*Primary Examiner* — Peter F Godenschwager
*Assistant Examiner* — Andrew J Oyer
(74) *Attorney, Agent, or Firm* — Birch, Stewart, Kolasch & Birch, LLP

(57) ABSTRACT

Provided are an organic semiconductor material having a high charge mobility, oxidation stability, and solvent solubility, an organic semiconductor device using the same, and a novel aromatic heterocyclic compound to be used for the same and a production method therefor. The aromatic heterocyclic compound is represented by the following general formula (1), has two heteroatoms, and has a structure in which six rings are fused. In the formula, X represents an oxygen atom or N—R, and R represents hydrogen or a monovalent substituent. The organic semiconductor material contains the aromatic heterocyclic compound, and is used
(Continued)

for an organic semiconductor film or an organic device, such as an organic thin-film transistor or an organic photovoltaic device.

4 Claims, 4 Drawing Sheets

(51) Int. Cl.
*C07D 495/04* (2006.01)
*H01L 51/42* (2006.01)
*H01L 51/05* (2006.01)

(52) U.S. Cl.
CPC ...... *H01L 51/0068* (2013.01); *H01L 51/0073* (2013.01); *H01L 51/0094* (2013.01); *H01L 51/0558* (2013.01); *H01L 51/42* (2013.01); *Y02E 10/549* (2013.01); *Y02P 70/521* (2015.11)

(58) Field of Classification Search
CPC ............ H01L 51/0558; C07D 491/048; C07D 495/04; Y02P 70/521; Y02E 10/549
See application file for complete search history.

(56) References Cited

FOREIGN PATENT DOCUMENTS

| | | | | |
|---|---|---|---|---|
| JP | 2010087408 | A | * | 4/2010 |
| JP | 2010087408 | A | * | 4/2010 |
| JP | 2013-232521 | A | | 11/2013 |
| JP | 2013-234151 | A | | 11/2013 |
| JP | 2013234151 | A | * | 11/2013 |
| KR | 10-2011-0041726 | A | | 4/2011 |
| WO | WO 2011/074232 | A1 | | 6/2011 |
| WO | WO 2012/090462 | A1 | | 7/2012 |

OTHER PUBLICATIONS

English Translation of JP2013234151.*
International Search Report, issued in PCT/JP2014/057166, dated Jun. 10, 2014.
Anthony et al., "A Road Map to Stable, Soluble, Easily Crystallized Pentacene Derivatives," Organic Letters (2002), vol. 4, No. 1, pp. 15-18.
English translation of International Preliminary Report on Patentability and Written Opinion dated Sep. 29, 2015, in PCT International Application No. PCT/JP2014/057166.
Ktauk et al., "High-mobility polymer gate dielectric pentacene tin flim transistors," J. Appl. Phys. (Nov. 1, 2002), vol. 92, No. 9, pp. 5259-5263.
Sinringhaus et al., "Integrated Optoelectronic Devices Based on Conjugated Polymers," Science (Jun. 12, 1998), vol. 280, pp. 1741-1744.
Sundar et al., "Elastomeric Transistor Stamps: Reversible Probing of Charge Transport in Organic Crystals," Science (Mar. 12, 2004), vol. 303, pp. 1644-1646.
Xiao et al., "A Highly π-stacked Organic Semiconductor for Field-Effect Transistors Based on Linearly Condensed Pentathienoacene," J. Am.Chem. Soc. (2005), vol. 127, pp. 13281-13288.

* cited by examiner

AROMATIC HETEROCYCLIC COMPOUND, MANUFACTURING METHOD THEREOF, ORGANIC SEMICONDUCTOR MATERIAL, AND ORGANIC SEMICONDUCTOR DEVICE

TECHNICAL FIELD

The present invention relates to a novel aromatic heterocyclic compound, an organic semiconductor material containing the same, an organic semiconductor film obtained by using the organic semiconductor material, and an organic semiconductor device, such as an organic field-effect transistor.

BACKGROUND ART

In general, a high-temperature process and a high-vacuum process are essential for the formation of a semiconductor device using silicon, which is an inorganic semiconductor material, into a thin film. The high-temperature process is needed and hence silicon cannot be formed into a thin film on a plastic substrate or the like. Accordingly, it has been difficult to impart flexibility to a product into which the semiconductor device is incorporated or to reduce the weight of the product. In addition, the high-vacuum process is needed, and hence an increase in area of the product into which the semiconductor device is incorporated and a reduction in cost of the product have been difficult.

Under such circumstances, in recent years, research has been conducted on an organic semiconductor device utilizing an organic semiconductor material as an organic electronic part (such as an organic electroluminescence (EL) device, an organic field-effect transistor device, or an organic thin-film photoelectric conversion device). Such organic semiconductor material can markedly reduce a production process temperature as compared to the inorganic semiconductor material, and hence can be formed into a thin film on the plastic substrate or the like. Further, when an organic semiconductor having high solubility in a solvent and having satisfactory film formability is used, a thin film can be formed by an application method which does not require a vacuum process, for example, with an inkjet apparatus or the like. Consequently, the increase in area and the reduction in cost, which have been difficult in the case of the semiconductor device using silicon, which is the inorganic semiconductor material, are expected to be realized. As described above, the organic semiconductor material has advantages in, for example, the increase in area, the flexibility, the reduction in weight, and the reduction in cost as compared to the inorganic semiconductor material. Accordingly, the organic semiconductor material has been expected to find applications in organic semiconductor products taking advantage of such characteristics, e.g., information tags, large-area sensors such as electronic artificial skin sheets and sheet-type scanners, and displays such as liquid crystal displays, electronic paper, and organic EL panels.

The organic semiconductor material to be used for the organic semiconductor device expected to find a wide range of applications as described above is required to have a high charge mobility. For example, in an organic FET device, the charge mobility directly affects a switching speed and performance of an apparatus to be driven, and hence an improvement in charge mobility is an essential issue in achieving practical use. Further, as described above, in order to enable production of a semiconductor device by the application method, the organic semiconductor material is required to have solvent solubility, oxidation stability, and satisfactory film formability.

The high charge mobility is particularly mentioned as a characteristic required of the organic semiconductor. From this viewpoint, an organic semiconductor material having a charge-transporting property comparable to that of amorphous silicon has been reported in recent years. For example, the same level of charge mobility as that of the amorphous silicon has been reported in an organic field-effect transistor device (OFET) using, as an organic semiconductor material, pentacene, which is a hydrocarbon-based acene-type polycyclic aromatic molecule in which five benzene rings are linearly fused (Non Patent Literature 1). However, the use of pentacene as an organic semiconductor material for an OFET is disadvantageous from the viewpoints of an increase in area, flexibility, a reduction in weight, and a reduction in cost because an organic semiconductor thin-film layer is formed by a deposition method in an ultrahigh vacuum. In addition, there has been proposed a method of forming a pentacene crystal in a dilute solution of trichlorobenzene without employing a vacuum deposition method, but the production method is difficult and hence a stable device has not been obtained yet (Patent Literature 1). The fact that the hydrocarbon-based acene-type polycyclic aromatic molecule like pentacene has low oxidation stability has also been pointed out as a problem.

In addition, a polythiophene derivative having a long-chain alkyl group, such as poly(3-hexylthiophene), is soluble in a solvent, and its use in production of an organic semiconductor device by the application method has been reported (Non Patent Literature 2). However, there has been a problem in that its charge mobility is lower than that of a crystalline compound, and hence characteristics of the resultant organic semiconductor device are low.

In addition, pentathienoacene, in which thiophene rings are fused, is improved in oxidation resistance as compared to pentacene. However, pentathienoacene has a low carrier mobility and requires many steps in its synthesis, and hence has not been a material preferred for practical use (Non Patent Literature 3).

In addition, recently, there has been a report of an extremely high mobility achieved with a single crystal of rubrene, which is an acene having high solubility (Non Patent Literature 4). However, a film of rubrene formed by solution casting does not adopt such single-crystal structure, and does not provide a sufficient mobility.

As examples of a hydrocarbon-based acene-type compound having high solvent solubility and being relatively stable against oxidation, some compounds each obtained by substituting the 6- and 13-positions of pentacene with silylethynyl groups have been reported to provide coating films having good stability (Non Patent Literature 5). However, in such report, a qualitative property, i.e. an improvement in stability against oxidation is only mentioned in the text, and stability sufficient for practical use has not yet been obtained.

Under such circumstances, as a material having stability and a high carrier mobility, a heteroacene-based skeleton obtained by introducing a heteroatom, such as nitrogen or sulfur, into a hydrocarbon-based acene-type polycyclic aromatic skeleton has been reported in recent years.

For example, a polycyclic ring-fused compound in which two benzofuran skeletons, indole skeletons, or benzothiophene skeletons are fused to a naphthalene ring has been proposed as a material for an organic semiconductor layer of an organic TFT. However, there is no disclosure of, for example, a specific example in which two or more kinds of heteroatoms are introduced (Patent Literature 2 and Patent Literature 3).

CITATION LIST

Patent Literature

[PTL 1] WO 2003/01659 A1
[PTL 2] WO 2011/074232 A1
[PTL 3] WO 2012/090462 A1

Non Patent Literature

[NPL 1] Journal of Applied Physics, Vol. 92, 5259 (2002)
[NPL 2] Science, Vol. 280, (5370) 1741 (1998)
[NPL 3] Journal Of American Chemical Society, Vol. 127, 13281 (2005)
[NPL 4] Science, Vol. 303 (5664), 1644 (2004)
[NPL 5] Org. Lett., Vol. 4, 15 (2002)

SUMMARY OF INVENTION

An object of the present invention is to provide an organic semiconductor material having a high charge mobility, oxidation stability, and solvent solubility, an organic semiconductor device using the same, and a novel aromatic heterocyclic compound to be used for the same and a production method therefor.

The inventors of the present invention have made extensive investigations. As a result, the inventors have found an aromatic heterocyclic compound suitable as an organic semiconductor material having a high charge mobility, oxidation stability, and solvent solubility, and have found that an organic semiconductor device having high characteristics is obtained through the use of the compound in an organic semiconductor material or an organic semiconductor device. Thus, the inventors have attained the present invention.

According to one embodiment of the present invention, there is provided an aromatic heterocyclic compound, which is represented by the following general formula (1).

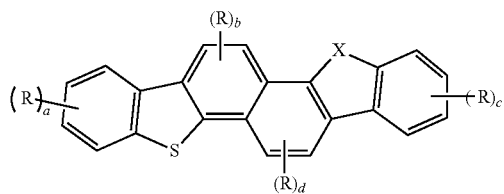

(1)

Wherein, X represents an oxygen atom or N—R; R's each independently represent a hydrogen atom or a monovalent substituent; a and c each represent an integer of from 1 to 4; and b and d each represent an integer of 1 or 2.

Aromatic heterocyclic compounds represented by the general formula (1) according to preferred embodiments of the present invention are as described below.

1) At least one of R's represents a monovalent substituent other than a hydrogen atom.
2) At least one of R's represents a monovalent group selected from the group consisting of: a halogen atom; a hydroxy group; a substituted or unsubstituted aliphatic hydrocarbon group having 1 to 30 carbon atoms; a substituted or unsubstituted alkoxy group having 1 to 30 carbon atoms; an amino group; a substituted amino group having 1 to 30 carbon atoms; a thiol group; a substituted sulfonyl group having 1 to 30 carbon atoms; a cyano group; a substituted or unsubstituted aromatic hydrocarbon group having 6 to 48 carbon atoms; a substituted or unsubstituted aromatic heterocyclic group having 2 to 48 carbon atoms; a substituted or unsubstituted aromatic hydrocarbon-substituted alkynyl group having 8 to 50 carbon atoms; a substituted or unsubstituted aromatic heterocycle-substituted alkynyl group having 4 to 50 carbon atoms; a substituted or unsubstituted aromatic hydrocarbon-substituted alkenyl group having 8 to 50 carbon atoms; a substituted or unsubstituted aromatic heterocycle-substituted alkenyl group having 4 to 50 carbon atoms; a substituted or unsubstituted alkylsilylalkynyl group having 5 to 30 carbon atoms; a substituted or unsubstituted alkylsilyl group having 3 to 30 carbon atoms; a substituted or unsubstituted siloxane group having 1 to 30 silicon atoms; a substituted or unsubstituted siloxane alkyl group having 1 to 30 silicon atoms; and a substituted or unsubstituted polysilane group having 1 to 30 silicon atoms.
3) The aromatic heterocyclic compound is represented by the following general formula (2).

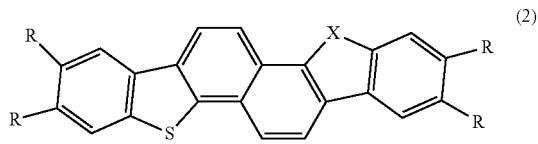

(2)

In the formula, X and R have the same meanings as X and R in the general formula (1), respectively.

According to another embodiment of the present invention, there is provided a production method for the aromatic heterocyclic compound represented by the general formula (1), where at least one of R's represents a monovalent group, the method including allowing an aromatic heterocyclic compound represented by the following general formula (7) and a compound represented by the following general formula (8) to react with each other to produce a compound in which $X_1$ in the general formula (7) is substituted with R.

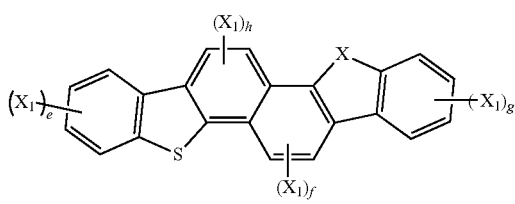

(7)

In the formula: X has the same meaning as X in the general formula (1); $X_1$'s each independently represent a reactive group selected from a halogen atom, a hydroxy group, —B(OH)$_2$, a sulfonyl group, a trifluoromethanesulfonate, a nonafluorobutanesulfonate, a fluorosulfonic acid ester, and a tosylate, or R in the general formula (1), provided that at least one of $X_1$'s represents a reactive group other than R; e and g each represent an integer of from 1 to 4; and f and h each represent an integer of 1 or 2.

R—Y (8)

In the formula: R has the same meaning as R in the general formula (1); and Y represents a group which reacts with $X_1$ in the general formula (7) to leave as $X_1$—Y and to allow substitution of $X_1$ with R.

According to another embodiment of the present invention, there is provided an organic semiconductor material, including the aromatic heterocyclic compound represented by the general formula (1). According to another embodiment of the present invention, there is provided an organic semiconductor film, which is formed of the organic semiconductor material. According to another embodiment of the present invention, there is provided an organic semiconductor film, which is formed through a step of applying and drying a solution prepared by dissolving the organic semiconductor material in an organic solvent. According to other embodiments of the present invention, there are provided an organic semiconductor device, including the organic semiconductor material, an organic thin-film transistor, including a semiconductor layer using the organic semiconductor material, and an organic photovoltaic device, including a semiconductor layer using the organic semiconductor material.

The aromatic heterocyclic compound of the present invention has, as a basic skeleton, a six-ring-fused structure in which benzothiophene is fused to one of the rings of naphtalene and a benzofuran ring or an indole ring is fused to the other ring. By virtue of the asymmetricity based on the introduction of two kinds of heteroatoms, the aromatic heterocyclic compound of the present invention has oxidation stability, high solubility, satisfactory film formability, and a high charge mobility characteristic. Therefore, the aromatic heterocyclic compound of the present invention is suitable as an organic semiconductor material, and the organic semiconductor device using the organic semiconductor material can express high characteristics. The organic semiconductor material is expected to find applications in, for example, organic field-effect transistors, organic thin-film solar cells, information tags, large-area sensors, such as electronic artificial skin sheets and sheet-type scanners, and displays such as liquid crystal displays, electronic paper, and organic EL panels, and hence has a high technical value.

DESCRIPTION OF EMBODIMENTS

Figure 1:
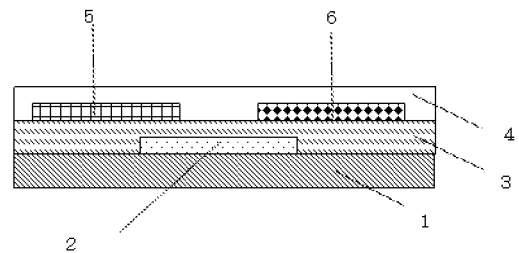
FIG. 1 is a schematic sectional view for illustrating an example of an organic field-effect transistor device.

An aromatic heterocyclic compound of the present invention is represented by the general formula (1). The aromatic heterocyclic compound represented by the general formula (1) is referred to as aromatic heterocyclic compound (1).

In the general formula (1), X represents an oxygen atom or N—R. R's each independently represent a hydrogen atom or a monovalent substituent. In addition, a and c each represent an integer of from 1 to 4, and b and d each represent an integer of 1 or 2. Herein, the monovalent substituent means a non-hydrogen atom or a group.

Out of R's, adjacent ones may be combined to form a ring. When R represents a monovalent substituent, R preferably represents a halogen atom, a hydroxy group, a substituted or unsubstituted aliphatic hydrocarbon group having 1 to 30 carbon atoms, a substituted or unsubstituted alkoxy group having 1 to 30 carbon atoms, an amino group, a substituted amino group having 1 to 30 carbon atoms, a thiol group, a substituted sulfonyl group having 1 to 30 carbon atoms, a cyano group, a substituted or unsubstituted aromatic hydrocarbon group having 6 to 48 carbon atoms, a substituted or unsubstituted aromatic heterocyclic group having 2 to 48 carbon atoms, a substituted or unsubstituted aromatic hydrocarbon-substituted alkynyl group having 8 to 50 carbon atoms, a substituted or unsubstituted aromatic heterocycle-substituted alkynyl group having 4 to 50 carbon atoms, a substituted or unsubstituted aromatic hydrocarbon-substituted alkenyl group having 8 to 50 carbon atoms, a substituted or unsubstituted aromatic heterocycle-substituted alkenyl group having 4 to 50 carbon atoms, a substituted or unsubstituted alkylsilylalkynyl group having 5 to 30 carbon atoms, a substituted or unsubstituted alkylsilyl group having 3 to 30 carbon atoms, a substituted or unsubstituted siloxane group having 1 to 30 silicon atoms, a substituted or unsubstituted siloxane alkyl group having 1 to 30 silicon atoms, or a substituted or unsubstituted polysilane group having 1 to 30 silicon atoms.

When R represents a halogen atom, preferred specific examples thereof include fluorine, bromine, chlorine, and iodine.

When R represents an unsubstituted aliphatic hydrocarbon group, an aliphatic hydrocarbon group having 1 to 30 carbon atoms is preferred, and an aliphatic hydrocarbon group having 1 to 12 carbon atoms is more preferred. Specific examples thereof may include: linear saturated hydrocarbon groups, such as a methyl group, an ethyl group, a n-propyl group, a n-butyl group, a n-pentyl group, a n-hexyl group, a n-octyl group, a n-dodecyl group, a n-tetradecyl group, a n-octadecyl group, a n-docosyl group, and a n-tetracosyl group; branched saturated hydrocarbon groups, such as an isopropyl group, an isobutyl group, a neopentyl group, a 2-ethylhexyl group, a 2-hexyloctyl group, and a 4-decyldodecyl group; saturated alicyclic hydrocarbon groups, such as a cyclopentyl group, a cyclohexyl group, a cyclooctyl group, a 4-butylcyclohexyl group, and a 4-dodecylcyclohexyl group; and unsaturated hydrocarbon groups, such as a vinyl group, an allyl group, a butenyl group, a pentenyl group, a hexenyl group, an octenyl group, a cyclobutenyl group, a cyclopentenyl group, a cyclohexenyl group, a cyclooctenyl group, an ethynyl group, a propynyl group, a butynyl group, a pentynyl group, a hexynyl group, and an octynyl group.

When R represents an unsubstituted alkoxy group, an alkoxy group having 1 to 30 carbon atoms is preferred, and an alkoxy group having 1 to 12 carbon atoms is more preferred. Specific examples thereof may include a methoxy group, an ethoxy group, a n-propoxy group, an i-propoxy group, a butoxy group, a pentyloxy group, a n-hexyloxy group, and an octyloxy group.

When R represents a substituted amino group, a substituted amino group having 1 to 30 carbon atoms is preferred, and a substituted amino group having 1 to 12 carbon atoms is more preferred. The substituted amino group may be secondary or tertiary. Specific examples thereof may include: alkylamino groups, such as a methylamino group, a dimethylamino group, an ethylamino group, a diethylamino group, and an octylamino group; and aromatic amino groups, such as a phenylamino group, a diphenylamino group, a naphthylamino group, a phenylnaphthylamino group, a pyridylphenylamino group, a piperidylnaphthylamino group, and a bipyridylamino group.

When R represents a substituted sulfonyl group, a substituted sulfonyl group having 1 to 30 carbon atoms is preferred, and a substituted sulfonyl group having 1 to 12 carbon atoms is more preferred. Specific examples thereof may include: alkylsulfonyl groups, such as a methylsulfonyl group, an ethylsulfonyl group, an ethylsulfonyl group, and an octylsulfonyl group; and aromatic sulfonyl groups, such as a phenylsulfonyl group, a naphthylsulfonyl group, a pyridylsulfonyl group, and a piperidylsulfonyl group.

When R represents an unsubstituted aromatic hydrocarbon group or aromatic heterocyclic group, an aromatic hydrocarbon group having 6 to 48 carbon atoms, or an aromatic heterocyclic group having 2 to 48 carbon atoms is preferred, and an aromatic hydrocarbon group having 6 to 24 carbon atoms, or an aromatic heterocyclic group having 3 to 18 carbon atoms is more preferred.

Specific examples of the unsubstituted aromatic hydrocarbon group or aromatic heterocyclic group include benzene, pentalene, indene, naphthalene, azulene, heptalene, octalene, indacene, acenaphthylene, phenalene, phenanthrene, anthracene, trindene, fluoranthene, acephenanthrylene, aceanthrylene, triphenylene, pyrene, chrysene, tetraphene, tetracene, pleiadene, picene, perylene, pentaphene, pentacene, tetraphenylene, helicene, hexaphene, rubicene, coronene, trinaphthylene, heptaphene, pyranthrene, ovalene, corannulene, fulminene, anthanthrene, zethrene, terrylene, naphthacenonaphthacene, truxene, furan, furofuran, difurofuran, benzofuran, isobenzofuran, benzofurobenzofuran, xanthene, oxanthrene, dibenzofuran, peri-xanthenoxanthene, thiophene, thienothiophene, dithienothiophene, benzothiophene, isobenzothiophene, benzothienobenzothiophene, thioxanthene, thianthrene, phenoxathiin, thionaphthene, isothianaphthene, thiophthene, thiophanthrene, dibenzothiophene, pyrrole, pyrrolopyrrole, indoloindole, dipyrrolopyrrole, pyrazole, tellurazole, selenazole, thiazole, isothiazole, oxazole, furazan, pyridine, pyrazine, pyrimidine, pyridazine, triazine, indolizine, indole, isoindole, indazole, purine, quinolizine, isoquinoline, carbazole, imidazole, naphthyridine, phthalazine, quinazoline, benzodiazepine, quinoxaline, cinnoline, quinoline, pteridine, phenanthridine, acridine, perimidine, phenanthroline, phenazine, carboline, phenotellurazine, phenoselenazine, phenothiazine, phenoxazine, anthyridine, thebenidine, quindoline, quinindoline, acrindoline, phthaloperine, triphenodithiazine, triphenodioxazine, phenanthrazine, anthrazine, thiazole, thiadiazole, benzothiazole, benzothiadiazole, benzimidazole, benzoxazole, benzisoxazole, benzisothiazole, indolocarbazole, and a group produced by removing hydrogen from an aromatic compound in which a plurality of such aromatic rings are linked to each other. More preferred examples of the unsubstituted aromatic hydrocarbon group or aromatic heterocyclic group include benzene, naphthalene, phenanthrene, anthracene, chrysene, furan, thiophene, thienothiophene, dithienothiophene, pyrrole, carbazole, indolocarbazole, and a group produced by removing hydrogen from an aromatic compound in which a plurality of such aromatic rings are linked to each other. It should be noted that in the case of the group produced from an aromatic compound in which a plurality of aromatic rings are linked to each other, the number of aromatic rings to be linked to each other is preferably from 2 to 10, more preferably from 2 to 7, and the aromatic rings to be linked to each other may be identical to or different from each other. In the case of a fused ring, a fused ring in which two to five rings are fused is preferred. It should be noted that when aromatic rings are linked to each other, the case of containing a heterocycle is included in the aromatic heterocyclic group. The term "aromatic ring" as used herein is meant to include an aromatic hydrocarbon ring, an aromatic heterocycle, or both. The terms "aromatic compound" and "aromatic group" are also similarly used.

In this case, the group produced by the linking of a plurality of aromatic rings is, for example, represented by any one of the following formulae.

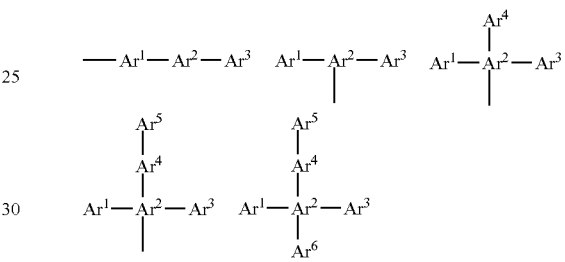

($Ar^1$ to $Ar^6$ each represent a substituted or unsubstituted aromatic ring.)

Specific examples of the group produced by linking a plurality of aromatic groups to each other include groups each produced by removing hydrogen from biphenyl, terphenyl, terthiophene, bipyridine, bipyrimidine, phenylnaphthalene, diphenylnaphthalene, phenylphenanthrene, pyridylbenzene, pyridylphenanthrene, bithiophene, terthiophene, bidithienothiophene, phenylindolocarbazole, or the like.

When R represents an unsubstituted aromatic hydrocarbon-substituted alkynyl group or alkenyl group, or an unsubstituted aromatic heterocycle-substituted alkynyl group or alkenyl group, an aromatic hydrocarbon-substituted alkenyl group or alkenyl group having 8 to 50 carbon atoms, or an aromatic heterocycle-substituted alkynyl group or alkenyl group having 6 to 50 carbon atoms is preferred, and an aromatic hydrocarbon-substituted alkenyl group or alkenyl group having 8 to 26 carbon atoms, or an aromatic heterocycle-substituted alkynyl group or alkenyl group having 6 to 26 carbon atoms is more preferred. An aromatic hydrocarbon group or an aromatic heterocyclic group with which the alkynyl group or the alkenyl group is substituted is similar to the aromatic hydrocarbon group or the aromatic heterocyclic group described above. Specific examples thereof may include phenylethenyl, naphthylethenyl, phenylethynyl, naphthylethynyl, thienylethenyl, furanylethenyl, thienylethynyl, and furanylethynyl.

When R represents an unsubstituted alkylsilylalkynyl group, an alkylsilylalkynyl group having 5 to 30 carbon atoms is preferred, and an alkylsilylalkynyl group having 5 to 20 carbon atoms is more preferred. Specific examples thereof may include a trimethylsilylethynyl group, a triethylsilylethynyl group, a triisopropylsilylethynyl group, and a triisobutylsilylethynyl group.

When R represents an unsubstituted alkylsilyl group, an alkylsilyl group having 3 to 30 carbon atoms is preferred, and an alkylsilyl group having 3 to 20 carbon atoms is more preferred. Specific examples thereof may include a trimethylsilyl group, a triethylsilyl group, a triisopropylsilyl group, and a triisobutylsilyl group.

When R represents an unsubstituted siloxane group, a siloxane group having 1 to 30 silicon atoms is preferred, and a siloxane group having 1 to 20 silicon atoms is more preferred. Specific examples thereof may include disiloxane, trisiloxane, tetrasiloxane, pentamethyldisiloxane, heptamethyltrisiloxane, nonamethyltetrasiloxane, pentaphenyldisiloxane, heptaphenyltrisiloxane, and nonaphenyltetrasiloxane.

When R represents an unsubstituted siloxyalkyl group, a siloxyalkyl group having 1 to 30 silicon atoms is preferred, and a siloxyalkyl group having 1 to 20 silicon atoms is more preferred. The siloxanealkyl group is understood as a group obtained by substituting the siloxane group with the linear saturated hydrocarbon group. Specific examples thereof may include disiloxaneethyl, trisiloxaneethyl, tetrasiloxaneethyl, disiloxanebutyl, trisiloxanebutyl, tetrasiloxanebutyl, pentamethyldisiloxaneethyl, heptamethyltrisiloxaneethyl, nonamethyltetrasiloxaneethyl, pentamethyldisiloxanebutyl, heptamethyltrisiloxanebutyl, and nonamethyltetrasiloxanebutyl.

When R represents an unsubstituted polysilane group, a polysilane group having 1 to 30 silicon atoms is preferred, and a polysilane group having 1 to 20 silicon atoms is more preferred. Specific examples thereof may include silane, disilane, trisilane, tetrasilane, pentamethyldisilane, heptamethyltrisilane, nonamethyltetrasilane, triphenylsilane, pentaphenyldisilane, heptaphenyltrisilane, and nonaphenyltetrasilane.

When R represents the aliphatic hydrocarbon group, alkoxy group, substituted amino group, substituted sulfonyl group, aromatic hydrocarbon group, aromatic heterocyclic group, aromatic hydrocarbon-substituted alkynyl group, aromatic heterocycle-substituted alkynyl group, aromatic hydrocarbon-substituted alkenyl group, aromatic heterocycle-substituted alkenyl group, alkylsilylalkynyl group, alkylsilyl group, siloxane group, siloxanealkyl group, or polysilane group, the groups may each further have a substituent, and the total number of the substituents is from 1 to 4, preferably 1 or 2. It should be noted that the group produced from an aromatic compound in which a plurality of aromatic rings are linked to each other may also similarly have a substituent. Preferred examples of the substituent include an alkyl group having 1 to 20 carbon atoms, an alkenyl group having 2 to 20 carbon atoms, an alkynyl group having 2 to 20 carbon atoms, an alkoxy group having 1 to 20 carbon atoms, an alkylamino group having 1 to 20 carbon atoms, an aromatic amino group having 6 to 20 carbon atoms, an alkylthio group having 1 to 20 carbon atoms, a hydroxy group, an alkoxycarbonyl group having 2 to 10 carbon atoms, an alkylsulfonyl group having 1 to 10 carbon atoms, a haloalkyl group having 1 to 10 carbon atoms, an alkylamide group having 2 to 10 carbon atoms, a trialkylsilyl group having 3 to 20 carbon atoms, a trialkylsilylalkyl group having 4 to 20 carbon atoms, a trialkylsilylalkenyl group having 5 to 20 carbon atoms, a trialkylsilylalkynyl group having 5 to 20 carbon atoms, an aromatic hydrocarbon group having 6 to 20 carbon atoms, an aromatic heterocyclic group having 2 to 20 carbon atoms, an aromatic hydrocarbon-substituted alkynyl group having 8 to 22 carbon atoms, an aromatic heterocycle-substituted alkynyl group having 4 to 22 carbon atoms, an aromatic hydrocarbon-substituted alkenyl group having 8 to 22 carbon atoms, and an aromatic heterocycle-substituted alkenyl group having 4 to 22 carbon atoms.

Specific examples thereof may include: linear saturated hydrocarbon groups, such as a methyl group, an ethyl group, a n-propyl group, an i-propyl group, a n-butyl group, a n-pentyl group, a n-hexyl group, a n-octyl group, a n-dodecyl group, a n-tetradecyl group, a n-octadecyl group, a n-docosyl group, and a n-tetracosyl group; branched saturated hydrocarbon groups, such as an isobutyl group, a neopentyl group, a 2-ethylhexyl group, a 2-hexyloctyl group, and a 4-decyldodecyl group; saturated alicyclic hydrocarbon groups, such as a cyclopentyl group, a cyclohexyl group, a cyclooctyl group, a 4-butylcyclohexyl group, and a 4-dodecylcyclohexyl group; and a methoxy group, an ethoxy group, a n-propoxy group, an i-propoxy group, a n-hexyloxy group, a methylamino group, a dimethylamino group, an ethylamino group, a dimethylamino group, a phenylamino group, a diphenylamino group, a methylthio group, an ethylthio group, an ethenyl group, a 1-propenyl group, a 2-propenyl group, an i-propenyl group, a 1-butenyl group, a 2-butenyl group, a 3-butenyl group, an ethynyl group, a 1-propynyl group, a 2-propynyl group, a 1-butynyl group, a 2-butynyl group, a 3-butynyl group, a methoxycarbonyl group, an ethoxycarbonyl group, a methoxycarbonyloxy group, an ethoxycarbonyloxy group, a methylsulfonyl group, an ethylsulfonyl group, a chloromethyl group, a chloroethyl group, a chloropropyl group, a chlorobutyl group, a chloropentyl group, a chlorohexyl group, a chlorooctyl group, a chlorododecyl group, a bromomethyl group, a bromoethyl group, a bromopropyl group, a bromobutyl group, a bromopentyl group, a bromohexyl group, a bromooctyl group, a bromododecyl group, a iodomethyl group, a iodoethyl group, a iodopropyl group, a iodobutyl group, a iodopentyl group, a iodohexyl group, a iodooctyl group, a iodododecyl group, a methylamide group, a dimethylamide group, an ethylamide group, a diethylamide group, a trimethylsilyl group, a triethylsilyl group, a triisopropylsilyl group, a triisobutylsilyl group, a trimethylsilylethyl group, a triethylsilylethyl group, a triisopropylsilylethyl group, a triisobutylsilylethyl group, a trimethylsilylethenyl group, a triethylsilylethenyl group, a triisopropylsilylethenyl group, a triisobutylsilylethynyl group, a trimethylsilylethynyl group, a triethylsilylethynyl group, a triisopropylsilylethynyl group, a triisobutylsilylethynyl group, benzene, naphthalene, phenanthrene, anthracene, chrysene, furan, thiophene, thienothiophene, dithienothiophene, pyrrole, carbazole, indolocarbazole, biphenyl, terphenyl, terthiophene, bipyridine, bipyrimidine, phenylnaphthalene, diphenylnaphthalene, phenylphenanthrene, pyridylbenzene, pyridylphenanthrene, bithiophene, terthiophene, bidithienothiophene, phenylindolocarbazole, phenylethenyl, naphthylethenyl, thienylethenyl, furanylethenyl, phenylethynyl, naphthylethynyl, thienylethynyl, and furanylethynyl. When two or more substituents are present, the substituents may be identical to or different from each other.

A preferred example of the compound represented by the general formula (1), that is, the aromatic heterocyclic compound (1) is an aromatic heterocyclic compound represented by the general formula (2). In the general formula (2), X and R have the same meanings as X and R in the general formula (1), respectively.

The aromatic heterocyclic compound represented by the general formula (2) is referred to as aromatic heterocyclic compound (2). The aromatic heterocyclic compound (2) is encompassed in the aromatic heterocyclic compound (1), and hence may be represented by the aromatic heterocyclic compound (1).

In addition, the present invention also relates to an aromatic heterocyclic compound represented by the following general formula (3):

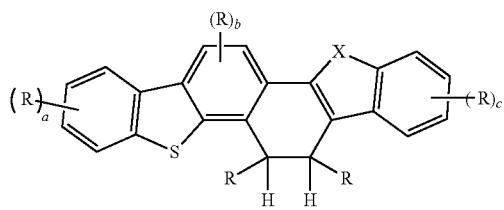

(3)

where X, R, a, b, c, and d have the same meanings as in the general formula (1).

As an aromatic heterocyclic compound represented by the general formula (3) according to a preferred embodiment of the present invention, there is given an aromatic heterocyclic compound represented by the following general formula (4):

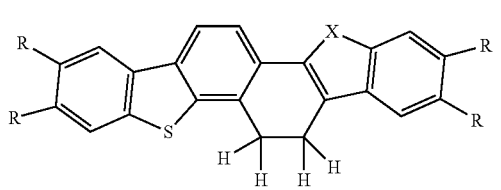

(4)

where X and R have the same meanings as in the general formula (3), and at least one of R's represents a monovalent substituent.

In addition, the present invention also relates to an aromatic heterocyclic compound represented by the following general formula (5):

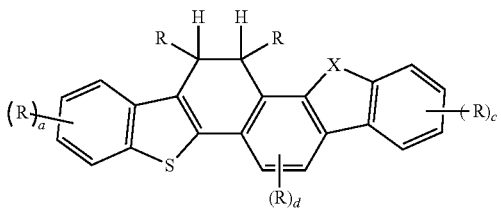

(5)

where X, R, a, b, c, and d have the same meanings as in the general formula (1).

As an aromatic heterocyclic compound represented by the general formula (5) according to a preferred embodiment of the present invention, there is given an aromatic heterocyclic compound represented by the following general formula (6):

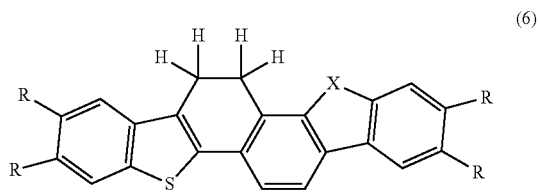

(6)

where X and R have the same meanings as in the general formula (5), and at least one of R's represents a monovalent group.

The aromatic heterocyclic compound represented by the general formula (3) or (5) is useful as an intermediate for producing the compound represented by the general formula (1) through a dehydrogenation reaction.

The aromatic heterocyclic compound represented by the general formula (4) or (6) is a more preferred compound of the general formula (3) or (5), and is useful as an intermediate for producing the compound represented by the general formula (2) through a dehydrogenation reaction.

The aromatic heterocyclic compounds represented by the general formulae (3) to (6) are referred to as aromatic heterocyclic compounds (3) to (6), respectively. The aromatic heterocyclic compound (4) is encompassed in the aromatic heterocyclic compound (3), and hence may be represented by the aromatic heterocyclic compound (3). The aromatic heterocyclic compound (6) is encompassed in the aromatic heterocyclic compound (5), and hence may be represented by the aromatic heterocyclic compound (5). In the general formulae (3) to (6), the same symbols as those in the general formula (1) have the same meanings as in the general formula (1).

Out of the aromatic heterocyclic compounds (3) of the present invention, a compound in which X represents N—R may be synthesized by, for example, a method as shown in the following reaction formula (A).

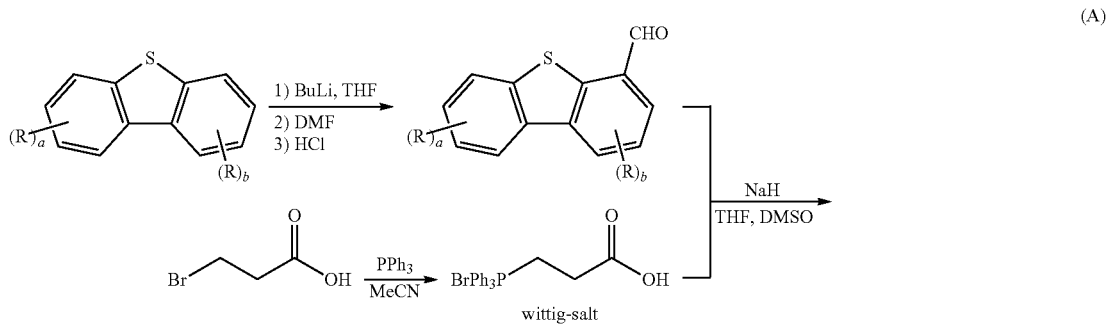

(A)

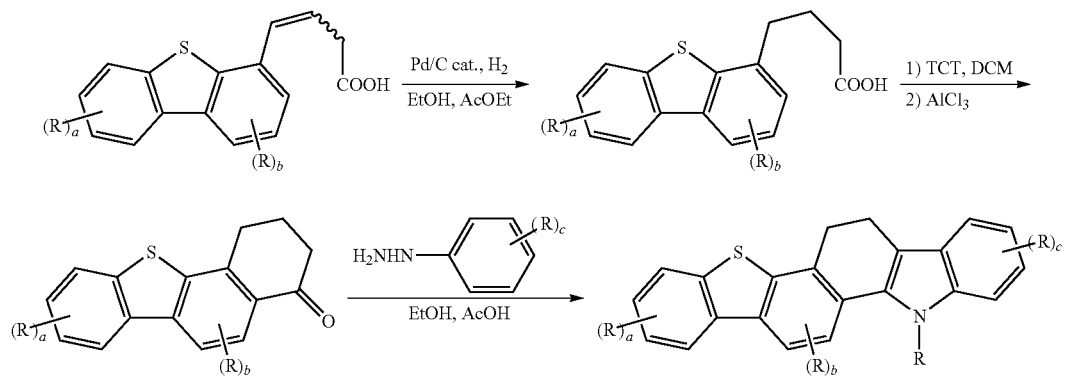

That is, the aromatic heterocyclic compound represented by the general formula (3) may be synthesized by: allowing a compound obtained by converting unsubstituted or substituted dibenzothiophene into an aldehyde, and a Wittig salt to act to synthesize a compound in which cyclohexanone is fused to dibenzothiophene; and allowing the synthesized compound to react with unsubstituted or substituted phenylhydrazine hydrochloride.

In addition, out of the aromatic heterocyclic compounds (3), a compound in which X represents O may be synthesized by, for example, a method as shown in the following reaction formula (B).

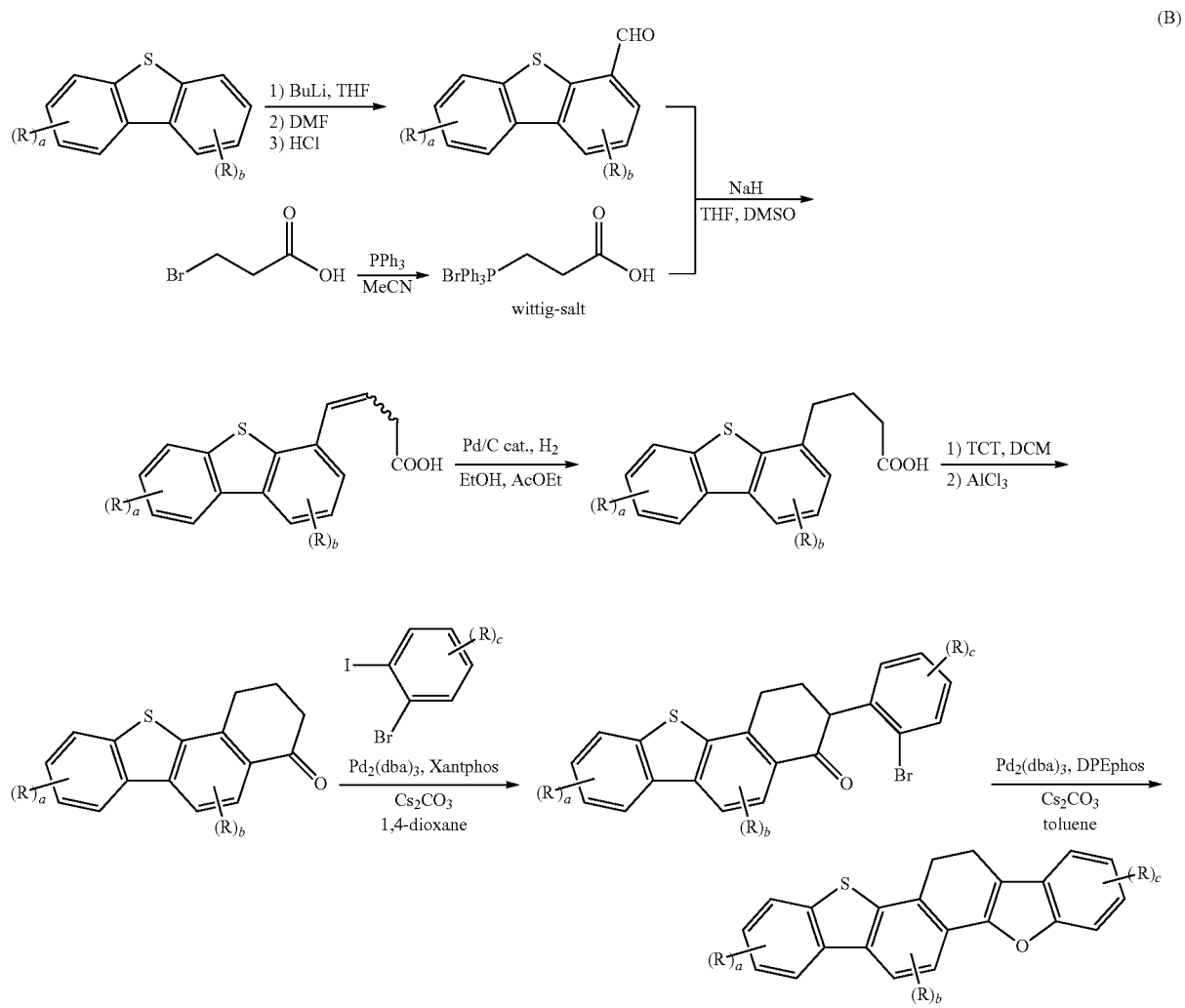

In addition, the aromatic heterocyclic compound (5) of the present invention may be synthesized by, for example, a method as shown in the following reaction formula (C).

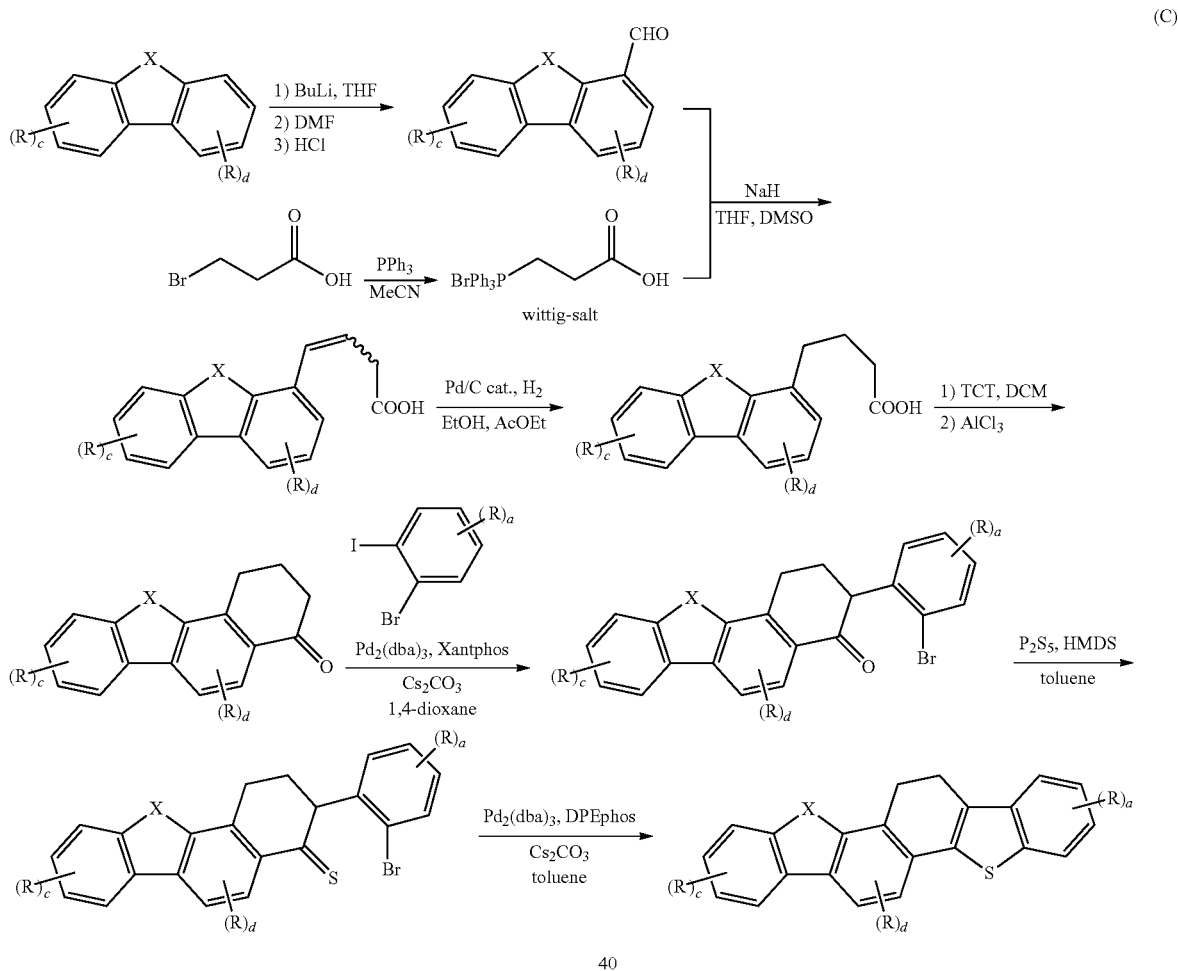

(C)

As shown in the following reaction formula (D), the aromatic heterocyclic compound (1) represented by the general formula (1) may be synthesized through a dehydrogenation reaction of the aromatic heterocyclic compound (3) or (5) represented by the general formula (3) or (5).

(D)

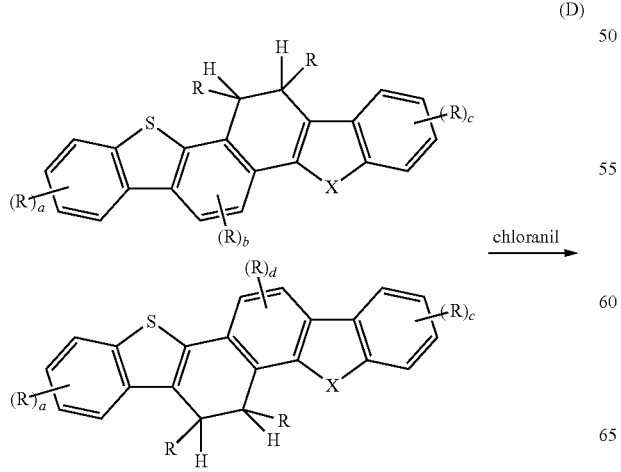

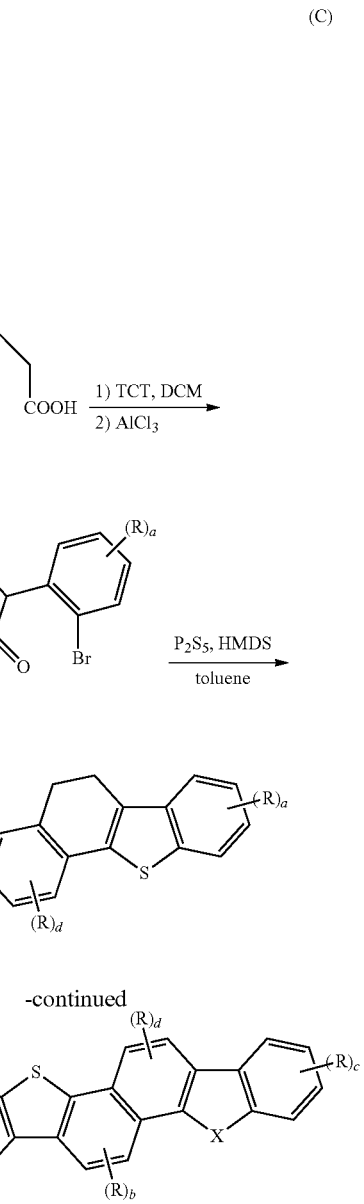

-continued

In addition, the aromatic heterocyclic compound (1) may be synthesized by allowing an aromatic heterocyclic compound represented by the general formula (7) (referred to as aromatic heterocyclic compound (7)) and a compound represented by the general formula (8) to react with each other.

In the general formula (7), X has the same meaning as X in the general formula (1). $X_1$'s each independently represent a reactive group selected from a halogen atom, a hydroxy group, —B(OH)$_2$, a sulfonyl group, a trifluoromethanesulfonate, a nonafluorobutanesulfonate, a fluorosulfonic acid ester, and a tosylate, or R in the general formula (1), provided that at least one of $X_1$'s represents a reactive group other than R. e and g each represent an integer of from 1 to 4, and f and h each represent an integer of 1 or 2. In the general formula (8), R has the same meaning as the monovalent group represented by R in the general formula (1), and Y represents a group which reacts with $X_1$ in the general formula (7) to leave as $X_1$—Y and to allow substitution of $X_1$ with R.

For example, a reaction method as shown in the following reaction formula (E) or (F) may be used.

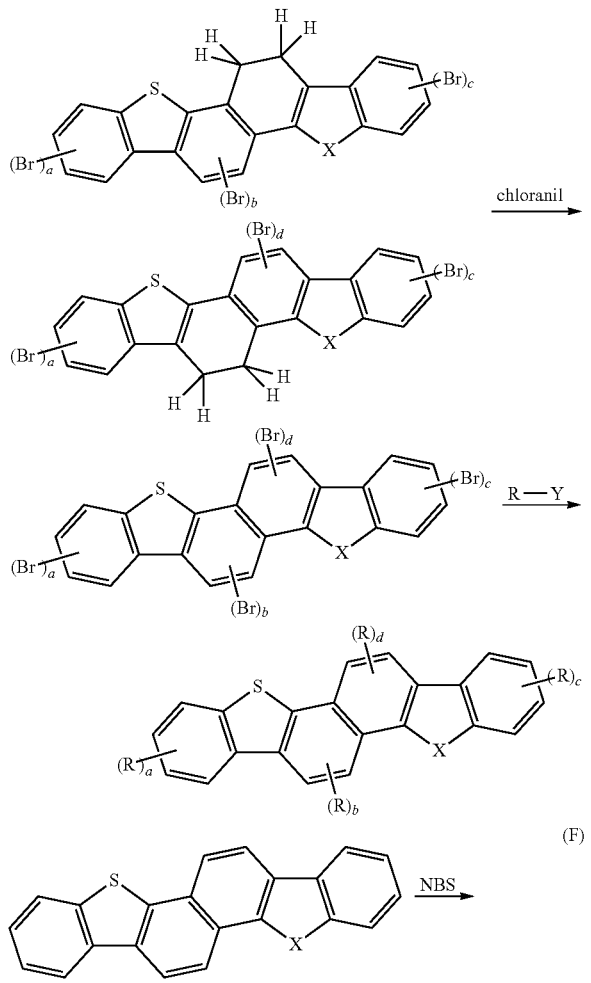

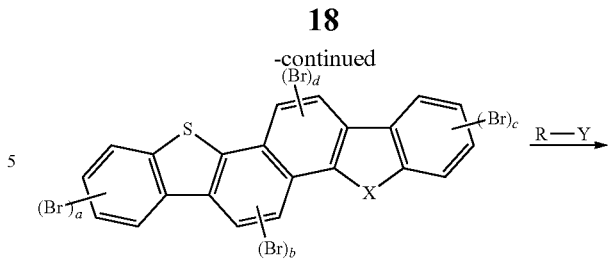

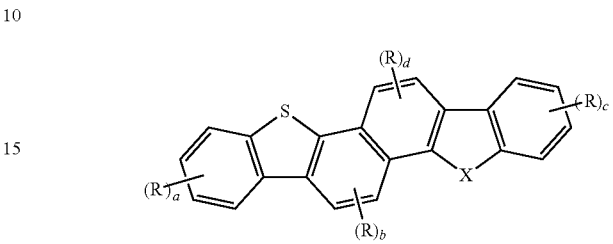

That is, when at least one of $X_1$'s in the general formula (7) represents a leaving functional group, such as a halogen atom, the aromatic heterocyclic compound represented by the general formula (1) or (2) may be synthesized through, for example, a cross-coupling reaction like a dehydrohalogenation reaction with the compound of the general formula (8) (R—Y). Examples of the cross-coupling reaction may include the Tamao-Kumada-Corriu reaction, the Negishi reaction, the Kosugi-Migita-Stille reaction, the Suzuki-Miyaura reaction, the Hiyama reaction, the Sonogashira reaction, and the Mizoroki-Heck reaction. A target product may be obtained by performing a reaction selected as required. In this case, the reaction is performed by selecting a metal catalyst, a reaction solvent, a base, a reaction temperature, a reaction time, and the like appropriate for each reaction. After that, as required, a post-treatment operation or a purification operation, such as extraction, is performed, and thus a target product having a desired purity may be obtained.

Preferred specific examples of the compound represented by the general formula (1) are shown below, but the compound is not limited thereto.

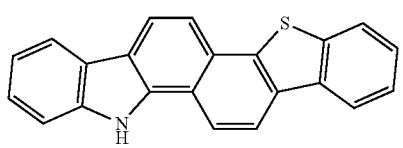 (A101)

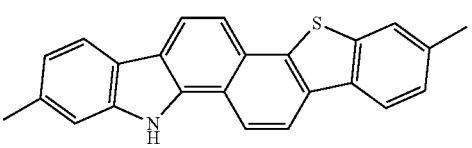 (A102)

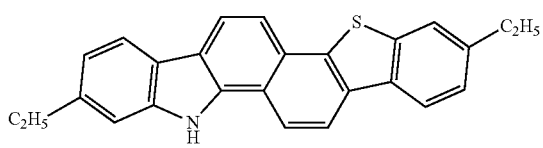 (A103)

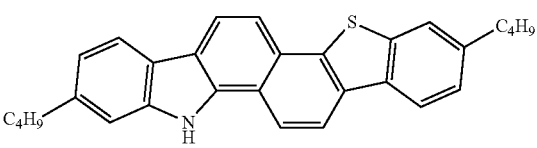 (A104)

-continued

-continued
(A123)
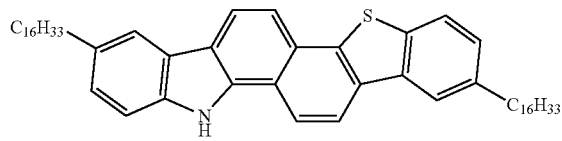
(A124)
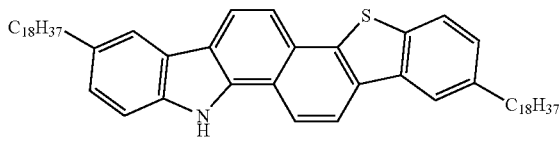
(A125)
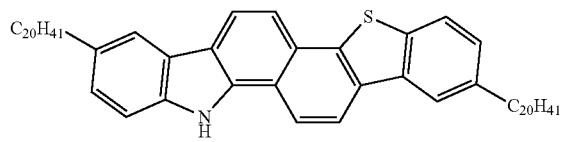
(A126)
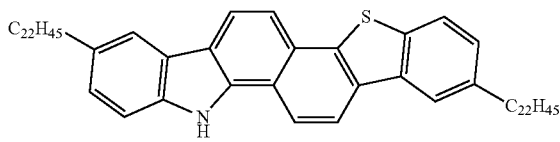
(A127)
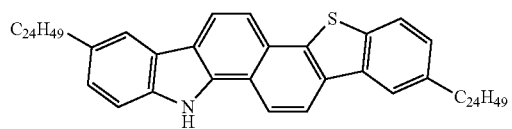
(A128)
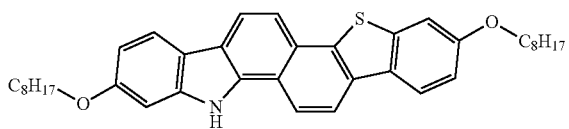
(A129)
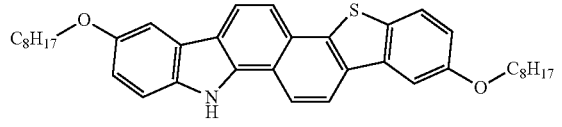
(A130)
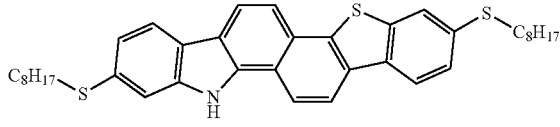
(A131)
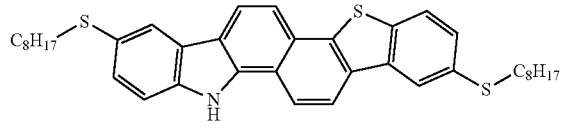
(A132)
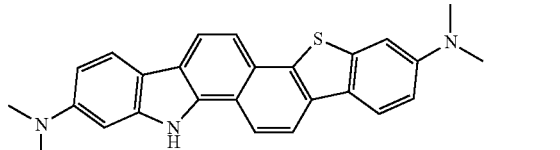
(A133)
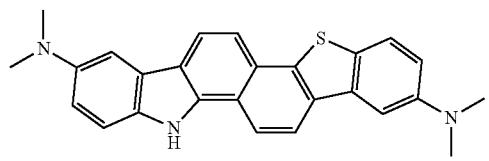
(A134)
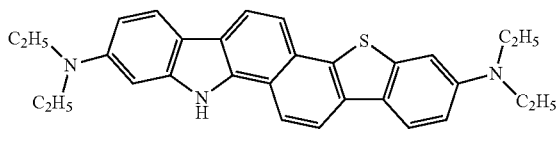
(A135)
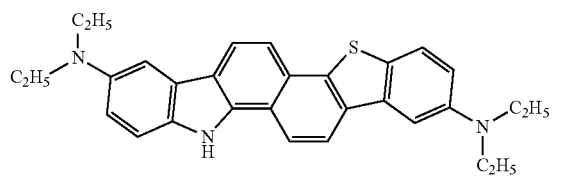
(A136)
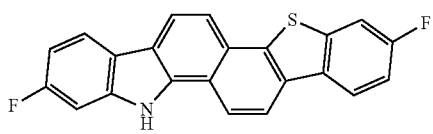
(A137)
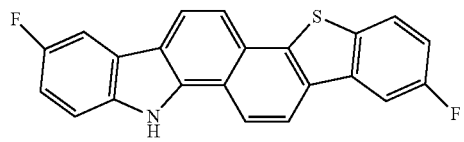
(A138)
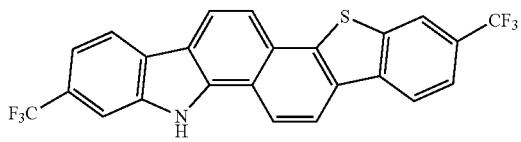
(A139)
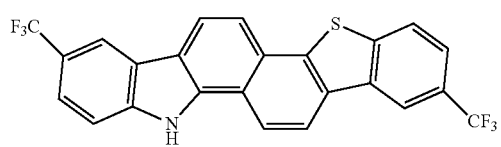
(A140)
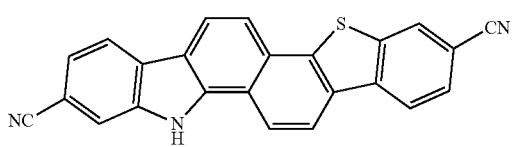

-continued
| (A141) | (A142) |
|---|---|
| 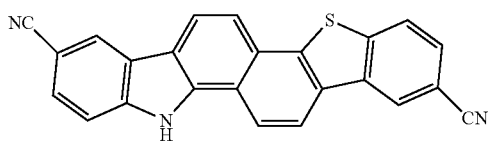 | 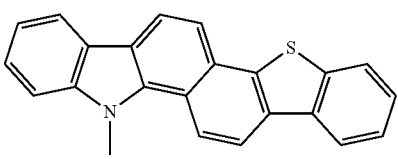 |
| (A143) | (A144) |
| 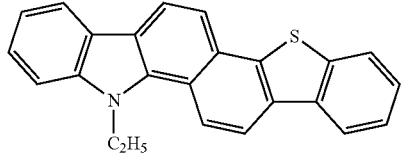 | |
| (A145) | (A201) |
| 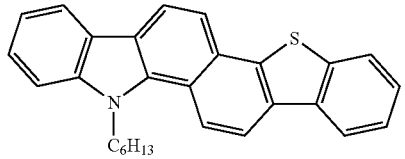 | |
| | (A202) |
| 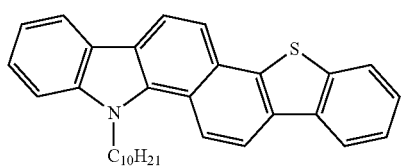 | |
| (A203) | (A204) |
| 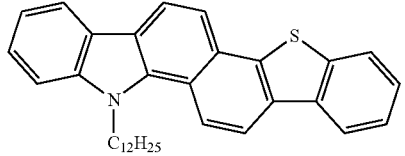 | |
| (A205) | (A206) |
| 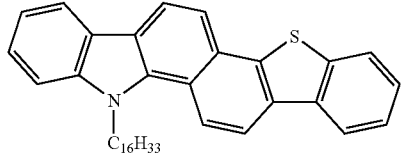 | |
| (A207) | (A208) |
| 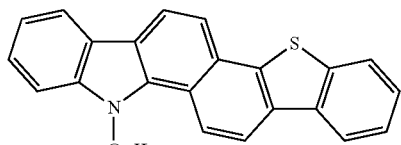 | |
| (A209) | (A210) |
| 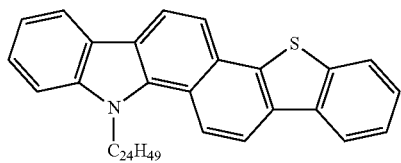 | |
| (A211) | (A212) |
| 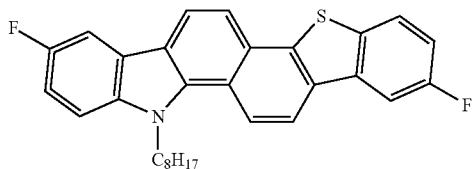 | 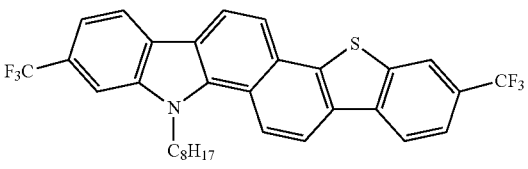 |

-continued
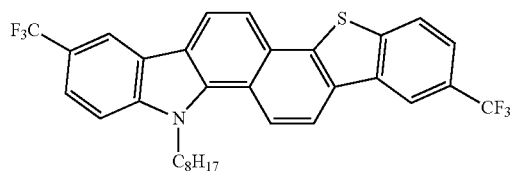
(A213)
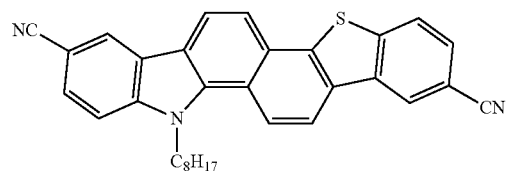
(A214)
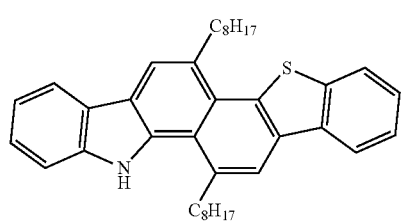
(A215)
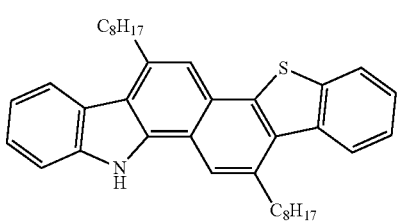
(A216)
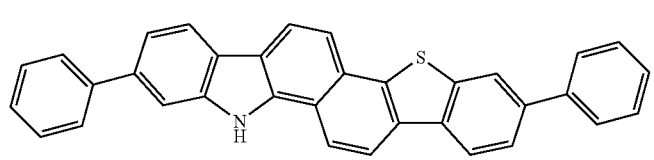
(A217)
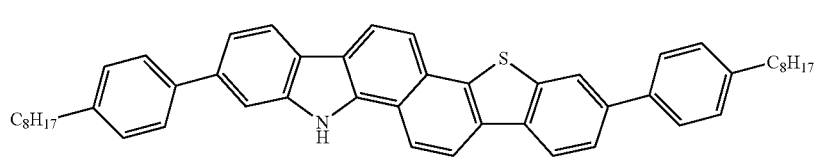
(A218)
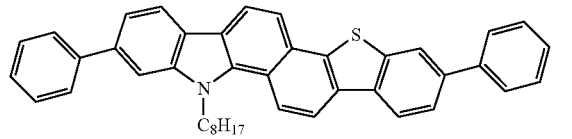
(A219)
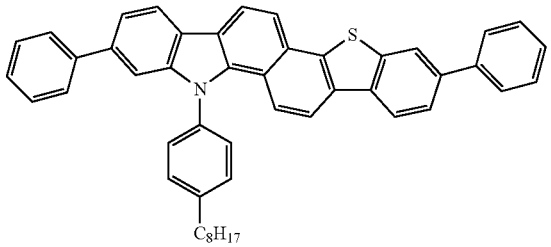
(A220)
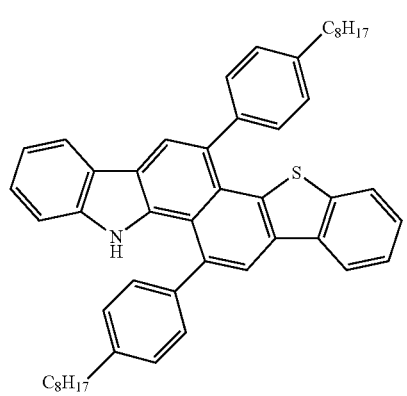
(A221)
(A222)
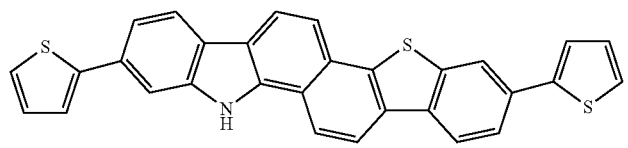
(A223)

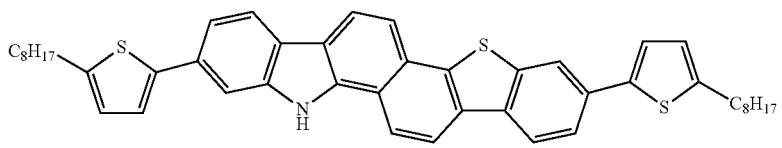
(A224)
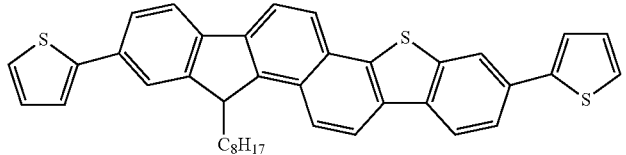
(A225)
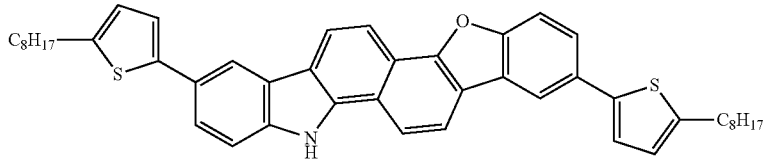
(A226)
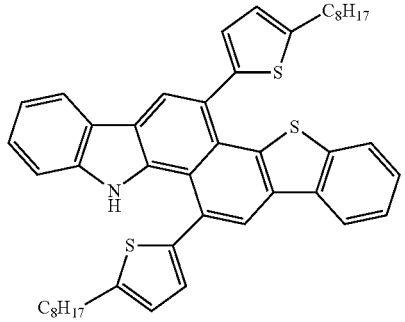
(A227)
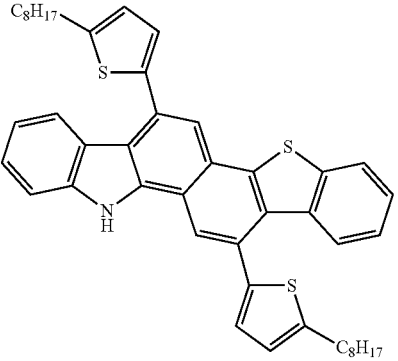
(A228)
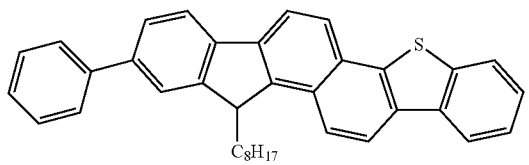
(A229)
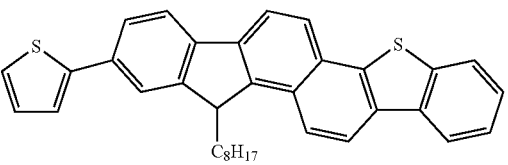
(A230)
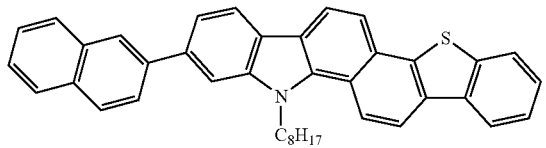
(A231)
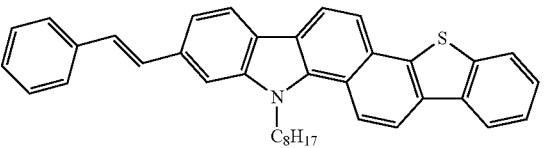
(A301)
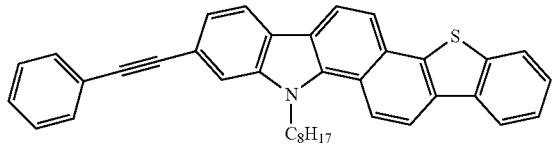
(A401)
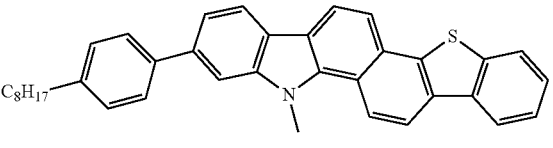
(A402)
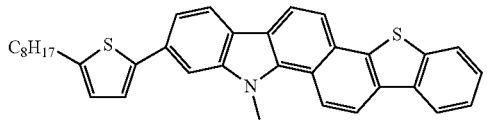
(A403)
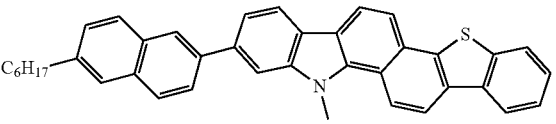
(A404)

-continued
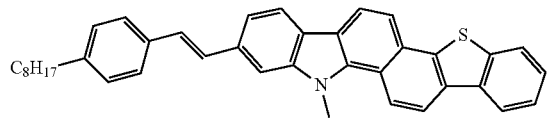
(A501)
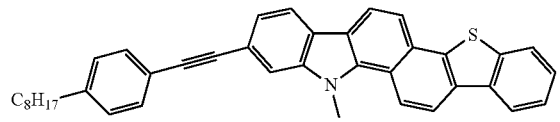
(A601)
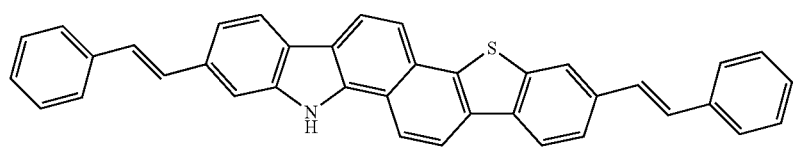
(A701)
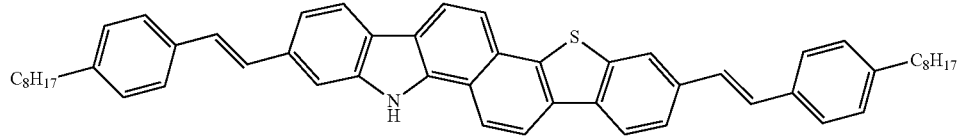
(A702)
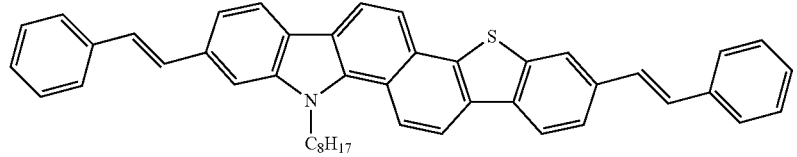
(A703)
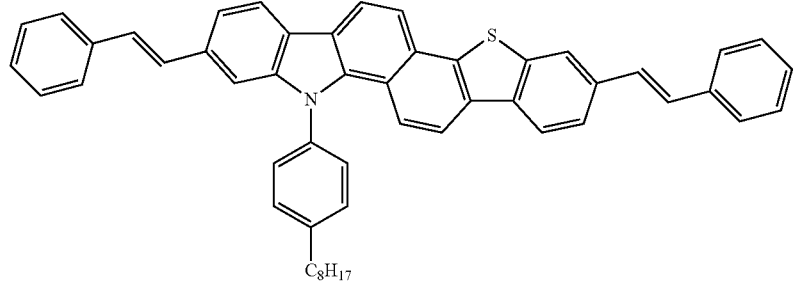
(A704)
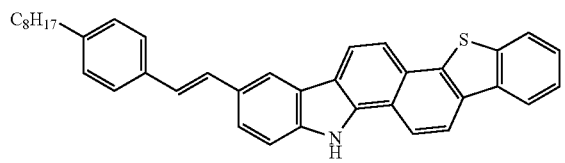
(A705)
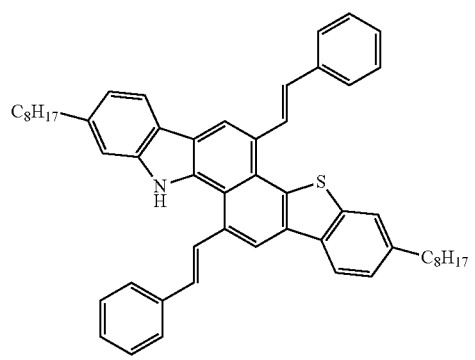
(A706)

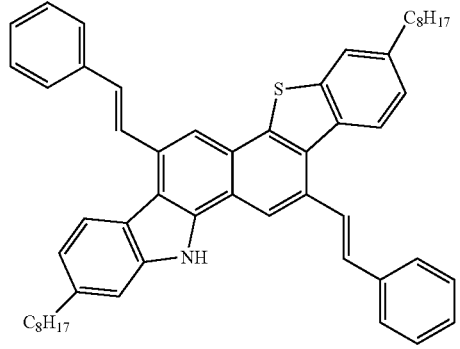
(A707)
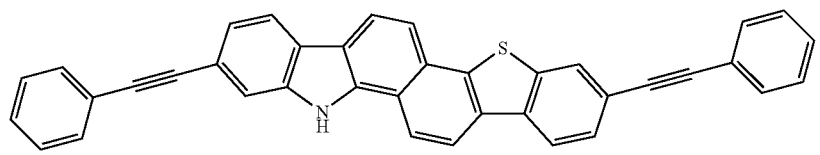
(A801)
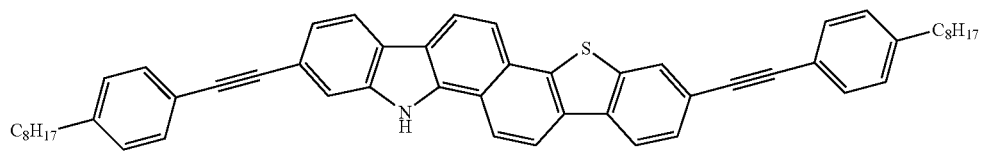
(A802)
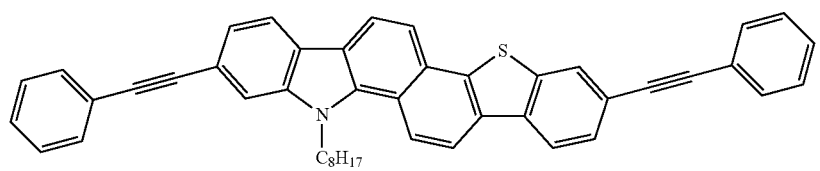
(A803)
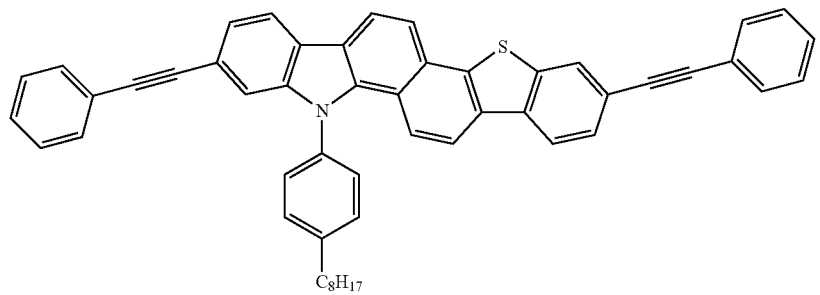
(A804)
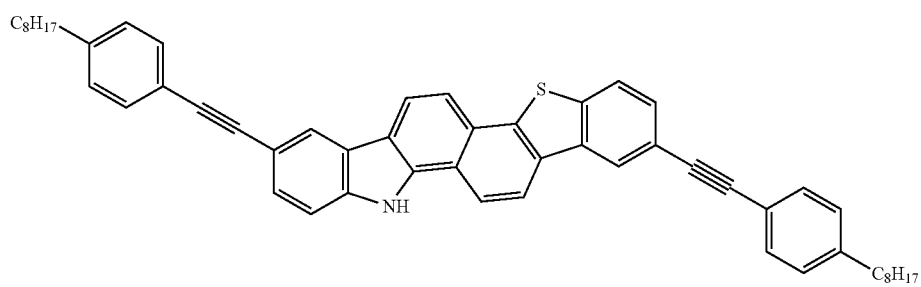
(A805)

(A806) 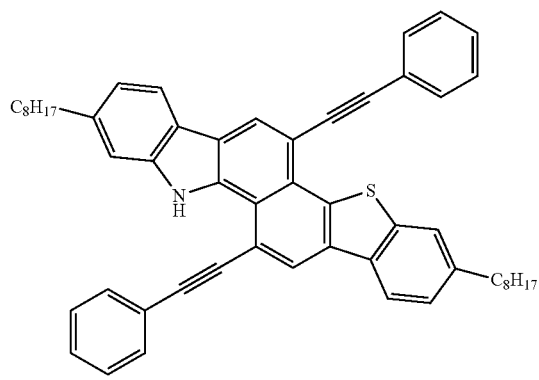
(A807) 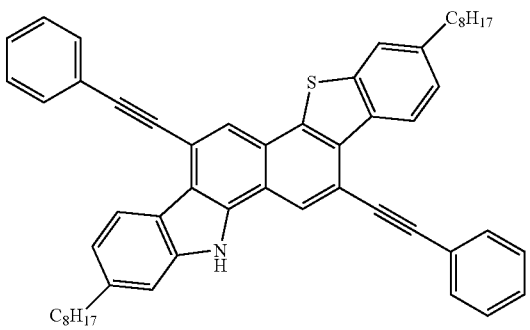
(A808) 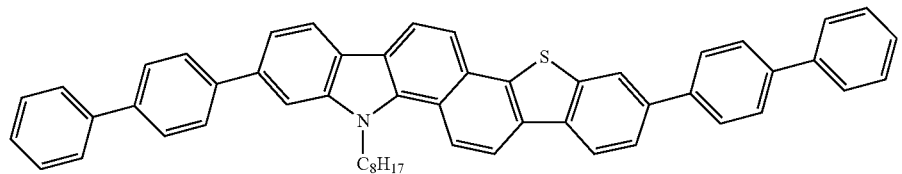
(A809) 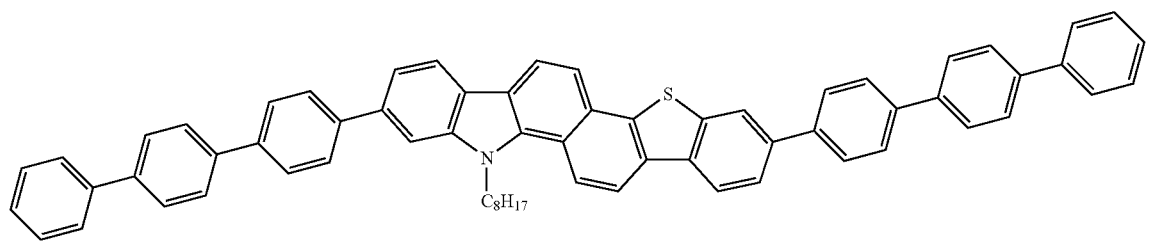
(A810) 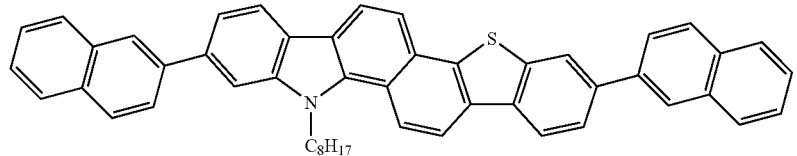
(A811) 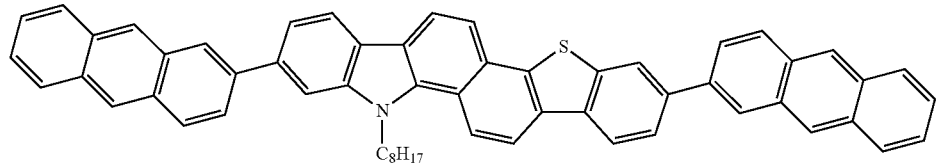
(A812) 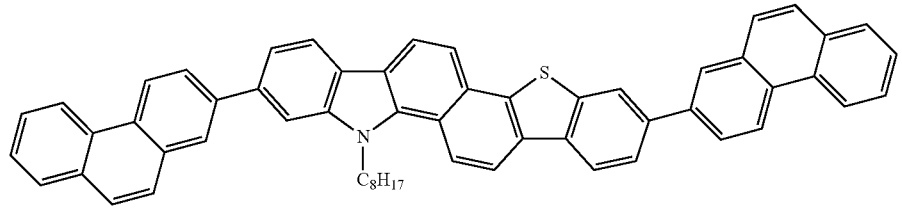
(A813) 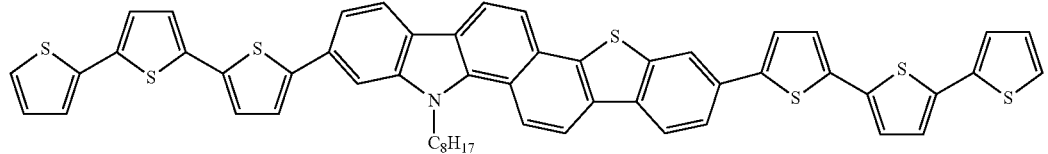

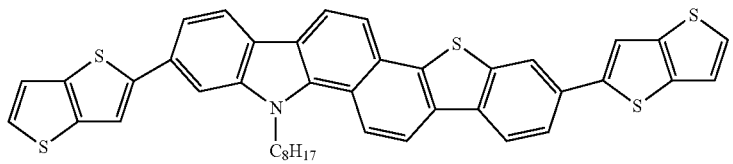
(A814)
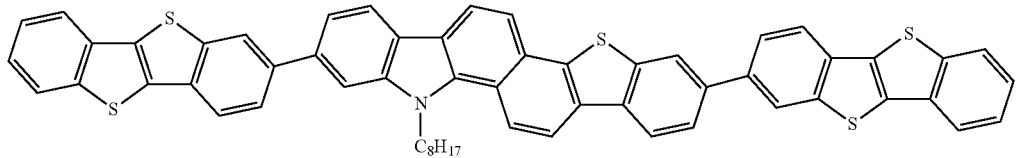
(A815)
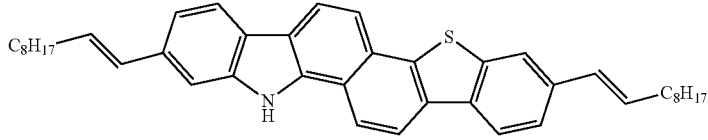
(A816)
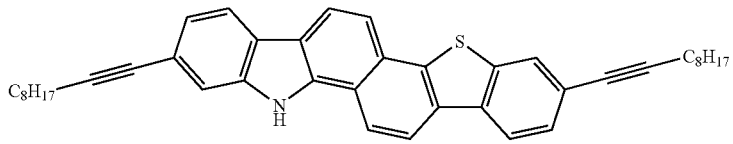
(A817)
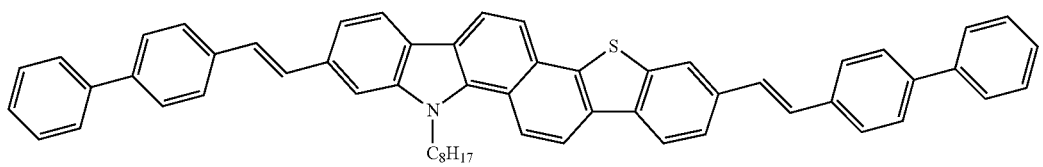
(A818)
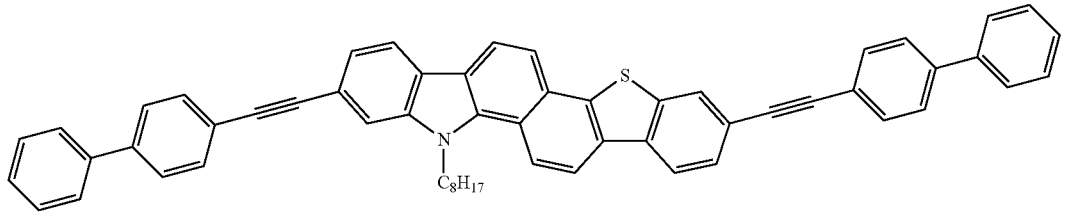
(A819)
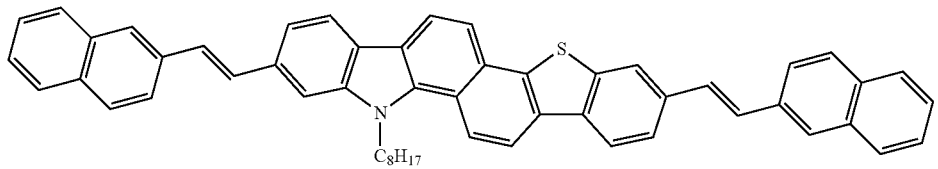
(A820)
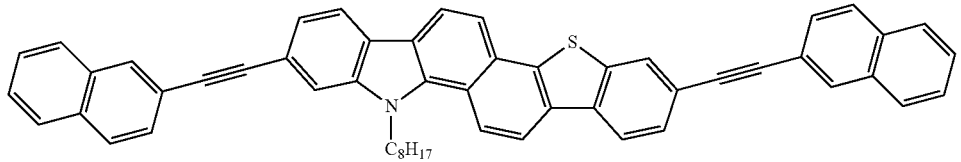
(A821)
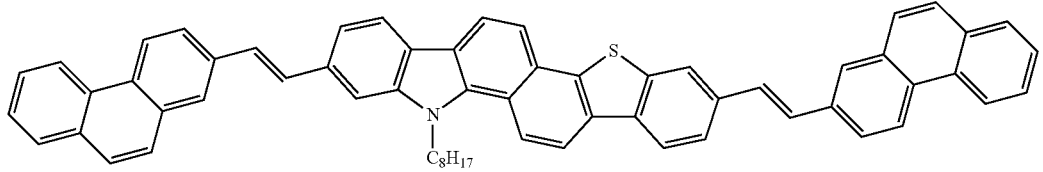
(A822)

-continued
(A823)
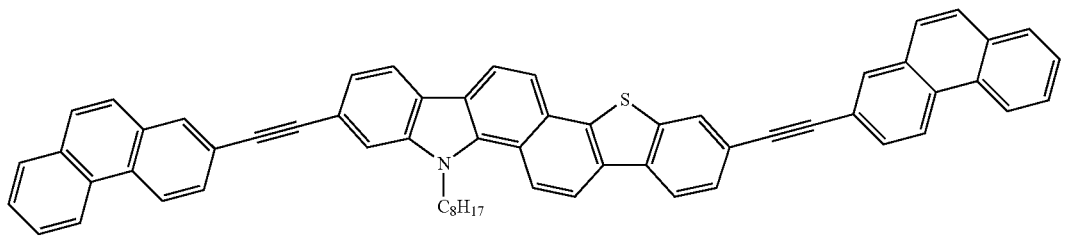
(A824)
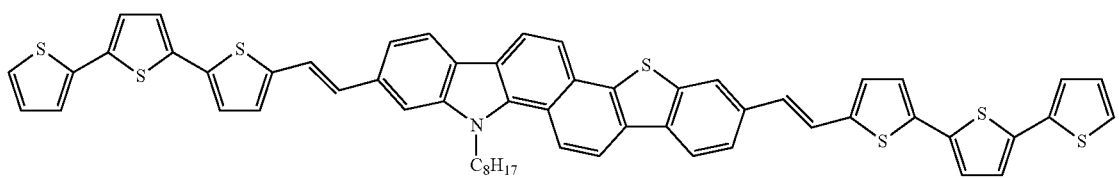
(A825)
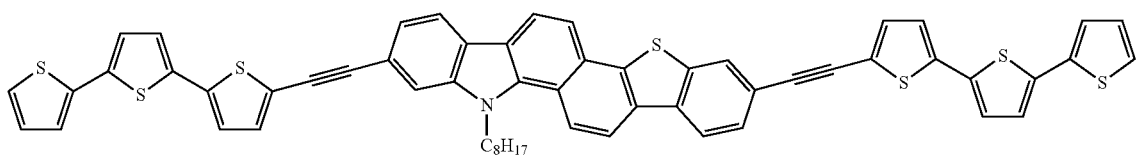
(A826)
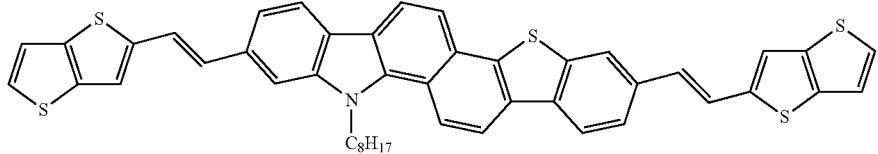
(A827)
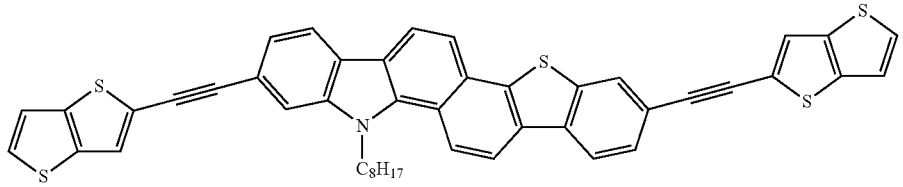
(A828)
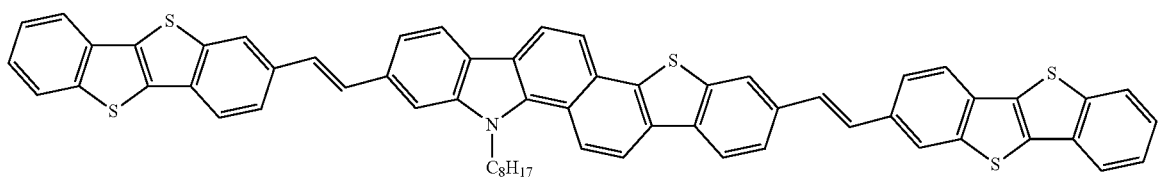
(A829)
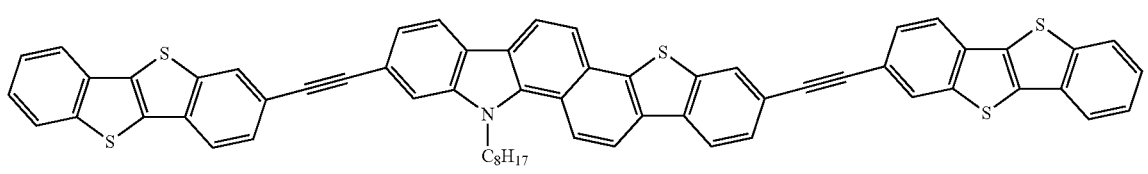
(A830)
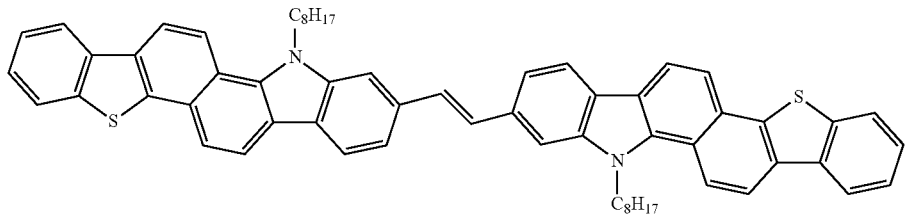

-continued
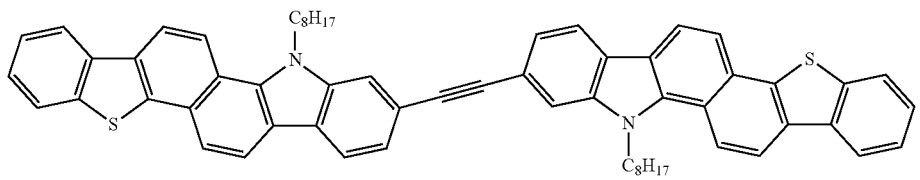
(A831)
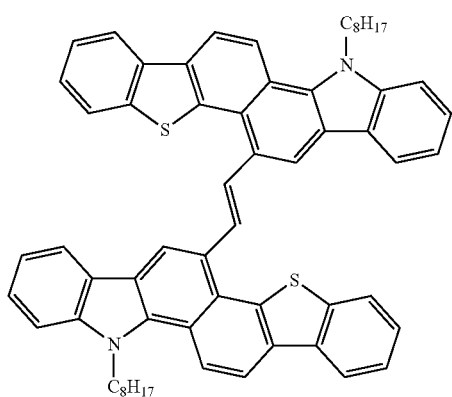
(A832)
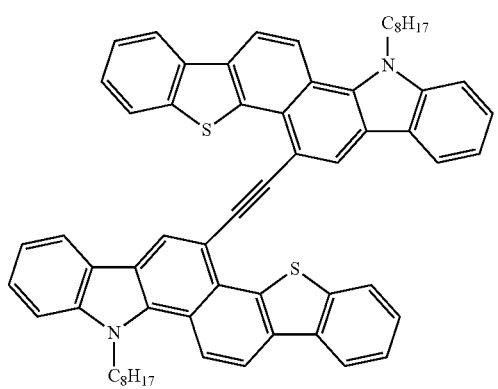
(A833)
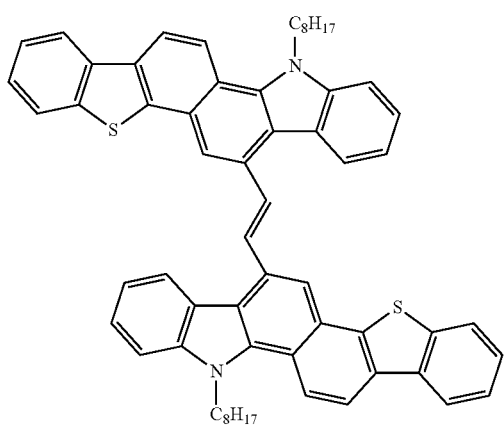
(A834)
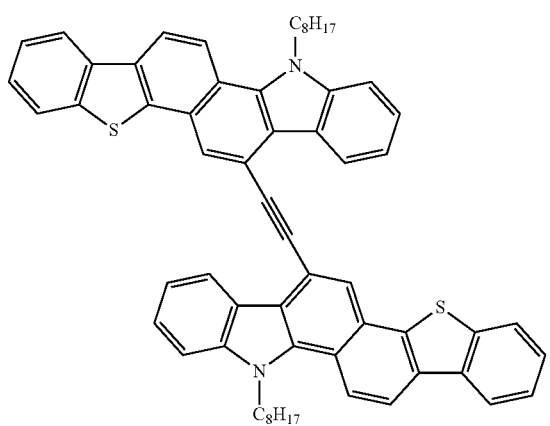
(A835)
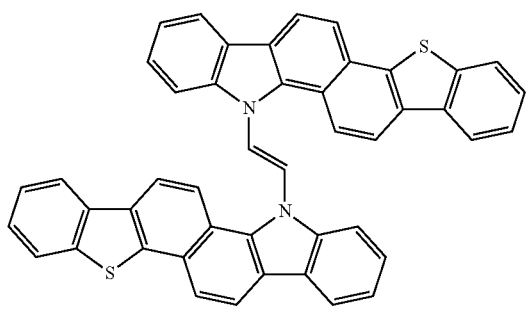
(A836)
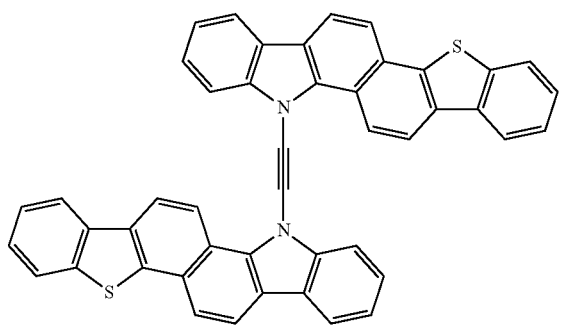
(A837)

-continued
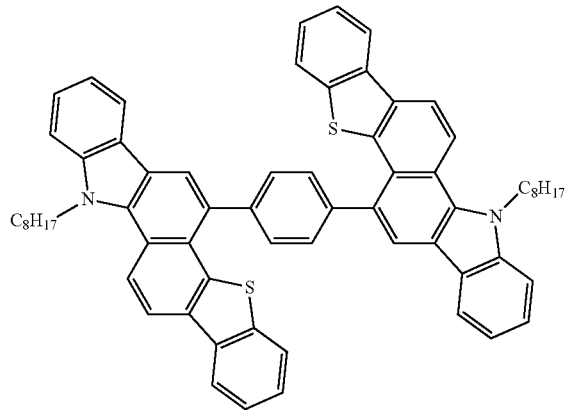
(A838)
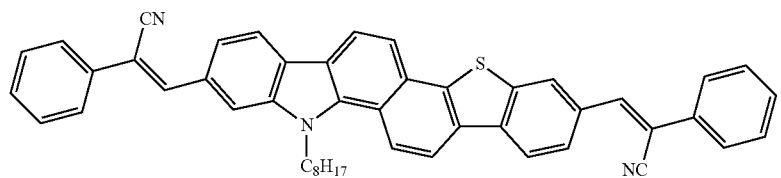
(A839)
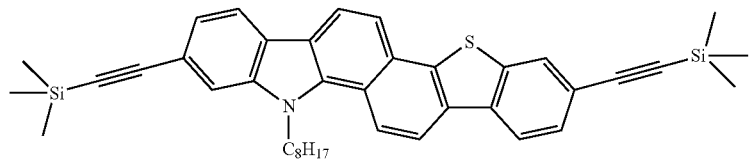
(A840)
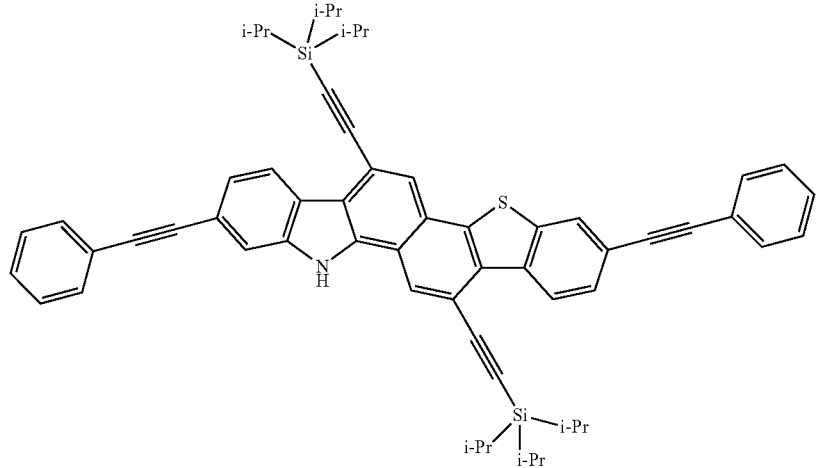
(A841)
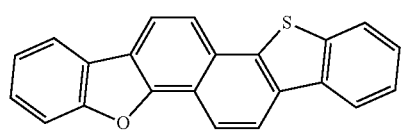
(B101)
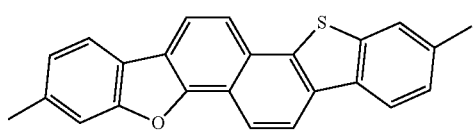
(B102)
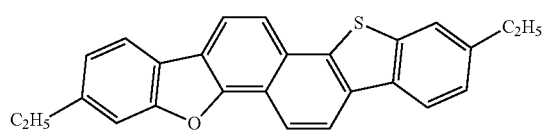
(B103)
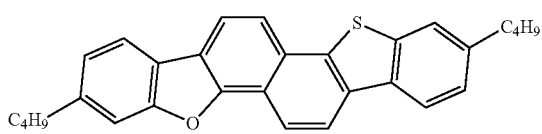
(B104)

-continued
(B105)
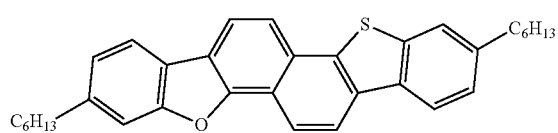
(B106)
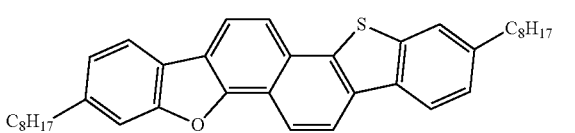
(B107)
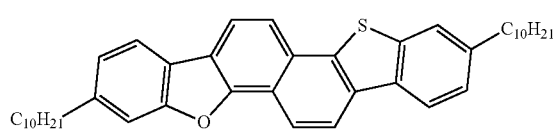
(B108)
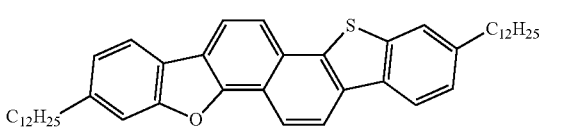
(B109)
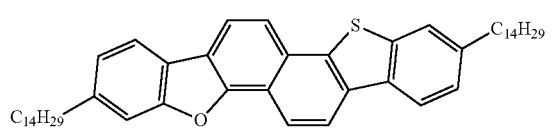
(B110)
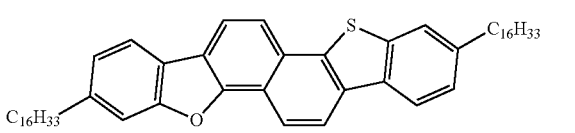
(B111)
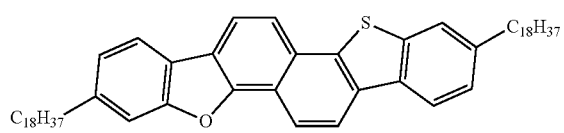
(B112)
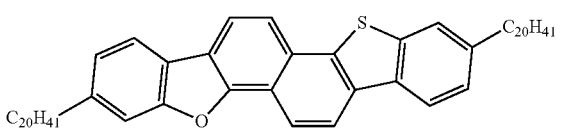
(B113)
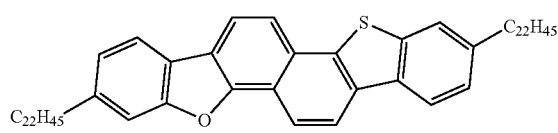
(B114)
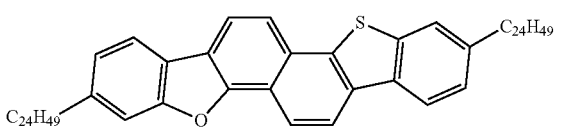
(B115)
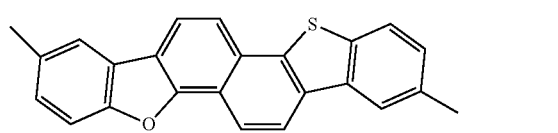
(B116)
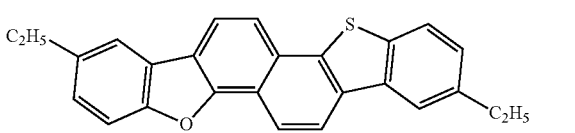
(B117)
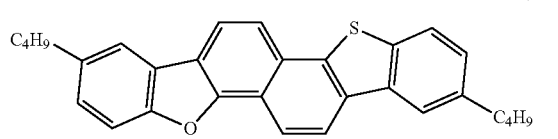
(B118)
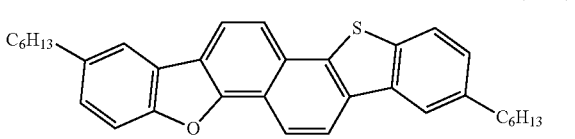
(B119)
(B120)
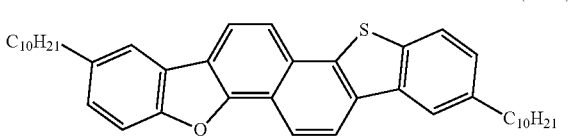
(B121)
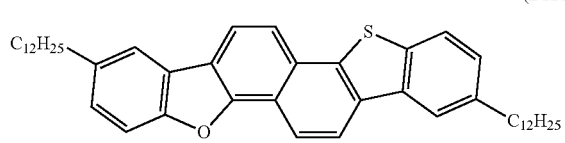
(B122)
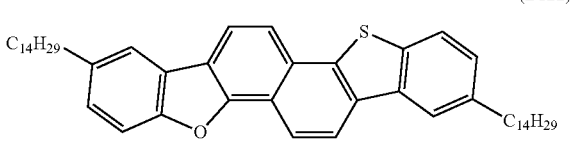
(B123)
(B124)
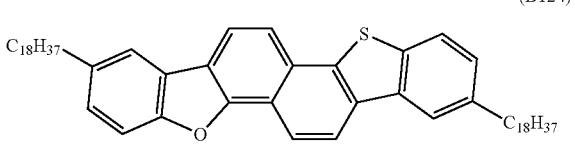

-continued
(B125) 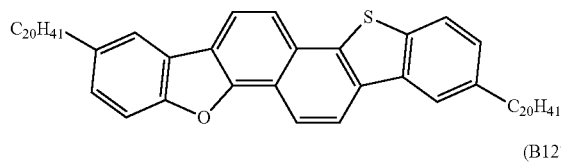
(B126) 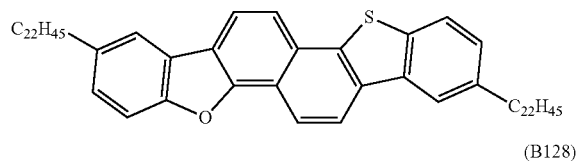
(B127) 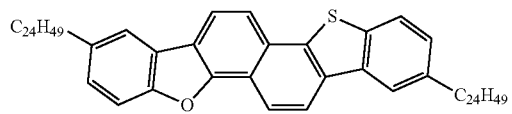
(B128) 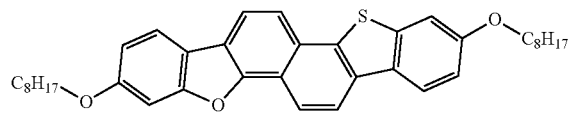
(B129) 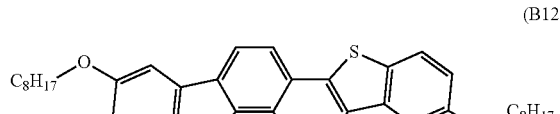
(B130) 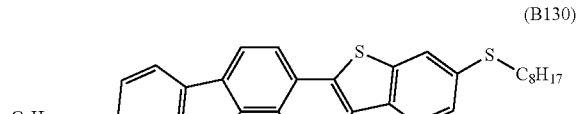
(B131) 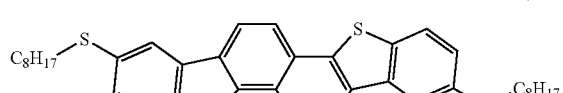
(B132) 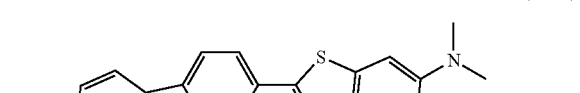
(B133) 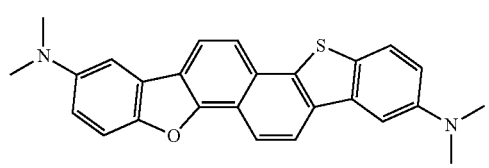
(B134) 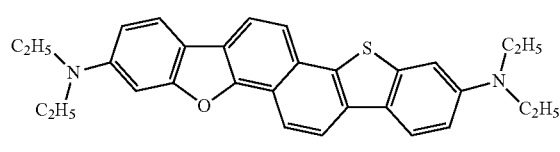
(B135) 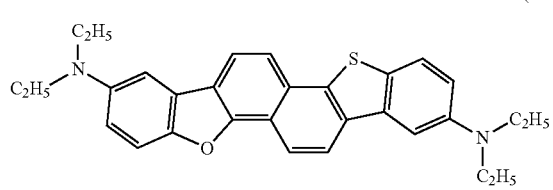
(B136) 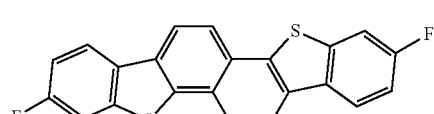
(B137) 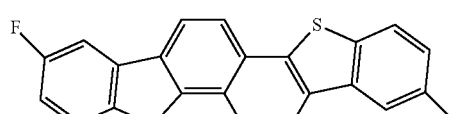
(B138) 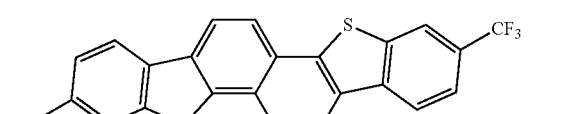
(B139) 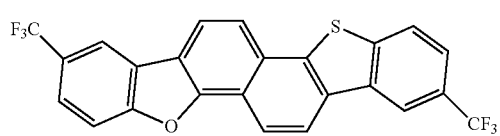
(B140) 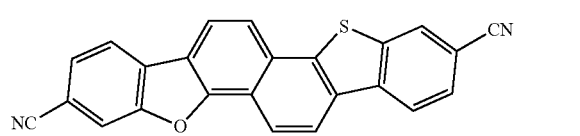
(B141) 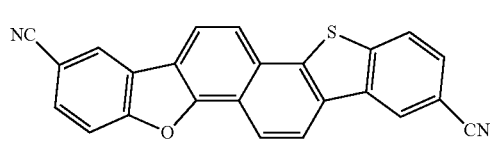
(B142) 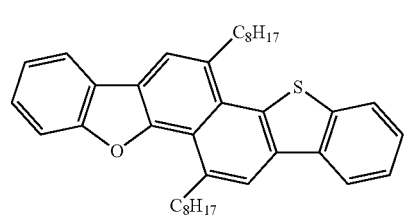

-continued
(B143) 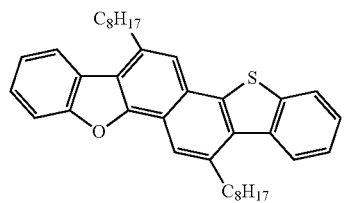 (B144)(B145) 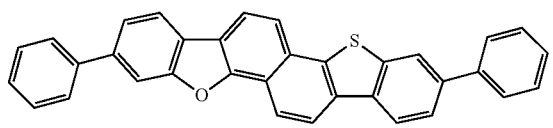
(B146)
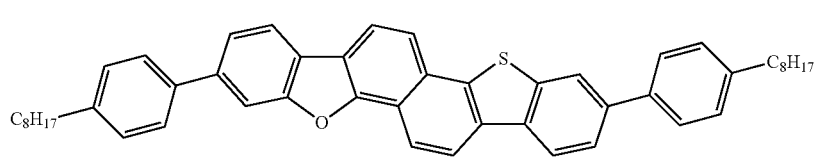
(B147) (B148)
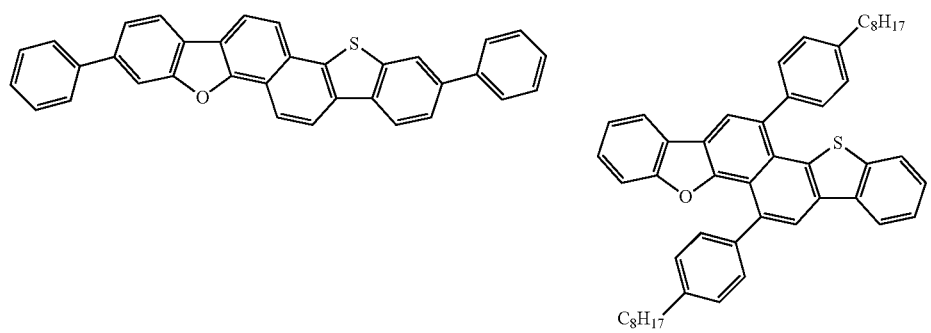
(B149) 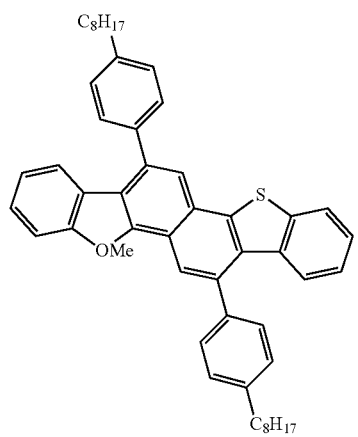 (B150) 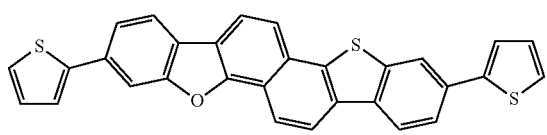
(B151)
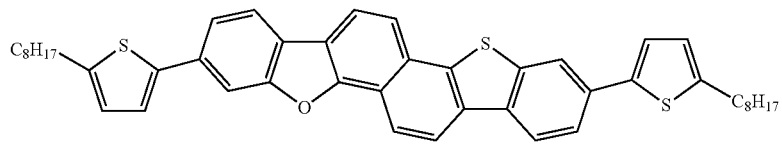
(B152)
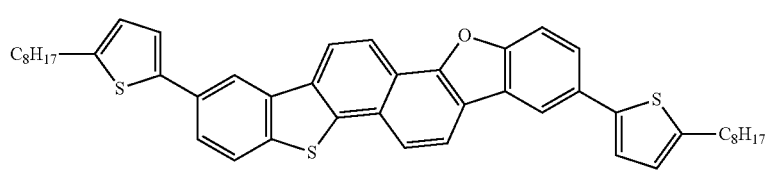

-continued
(B153) 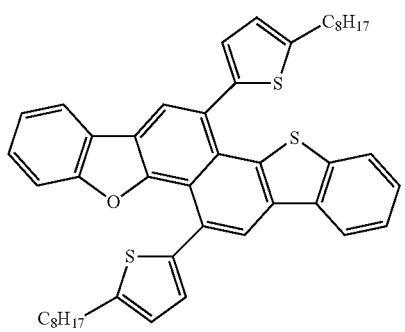
(B154) 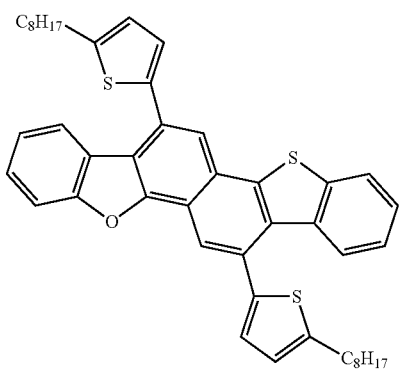
(B155) 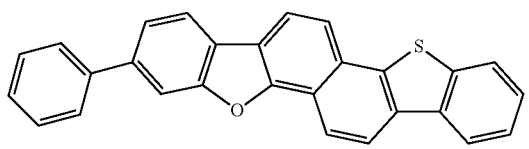
(B156) 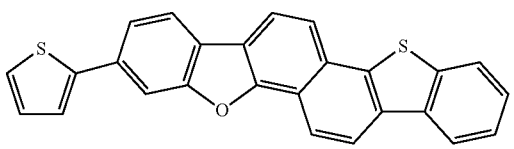
(B157) 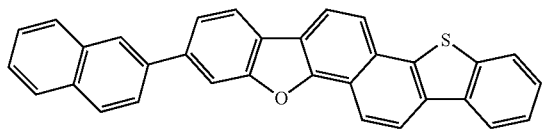
(B158) 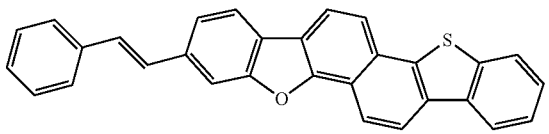
(B159) 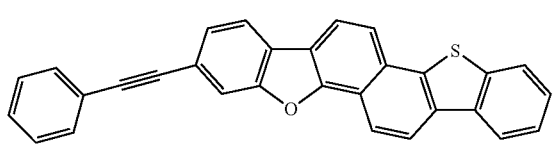
(B160) 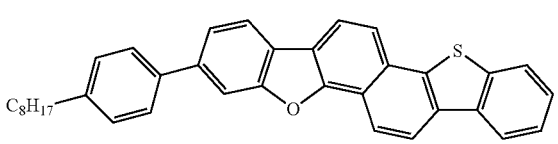
(B161) 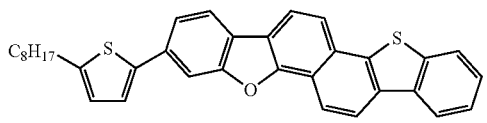
(B162) 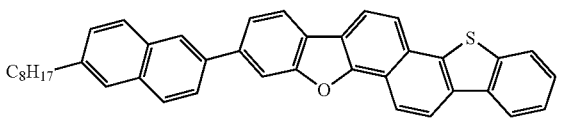
(B163) 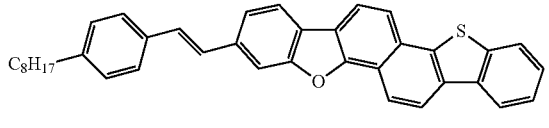
(B164) 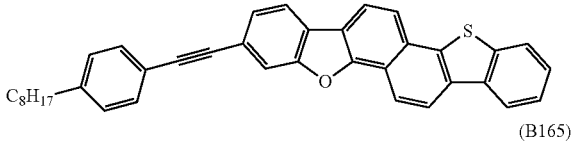
(B165) 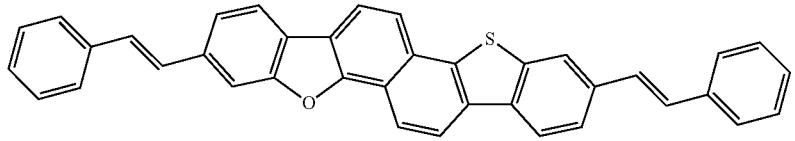
(B166) 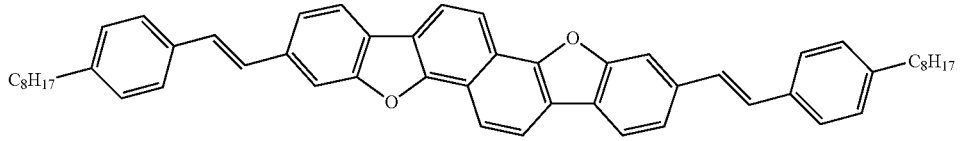
(B167) 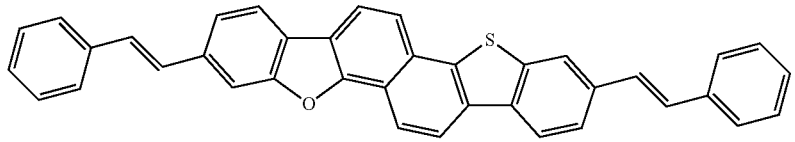

-continued
(B168)
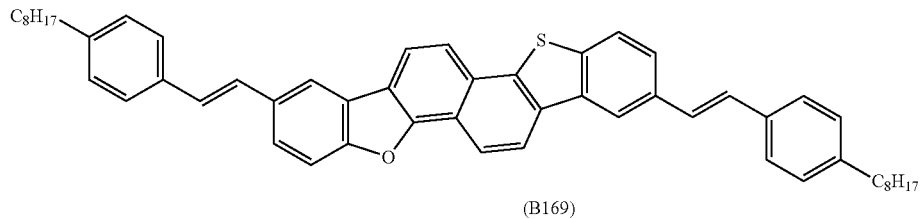
(B169)
(B170)
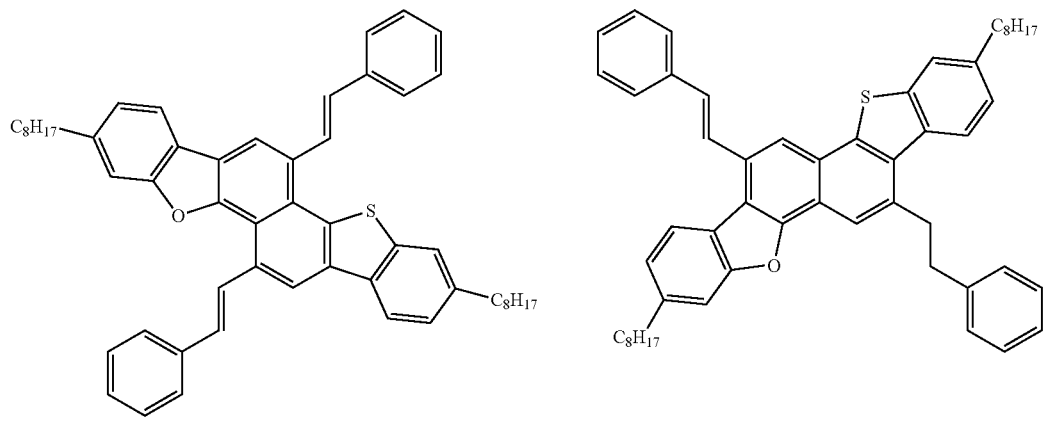
(B171)
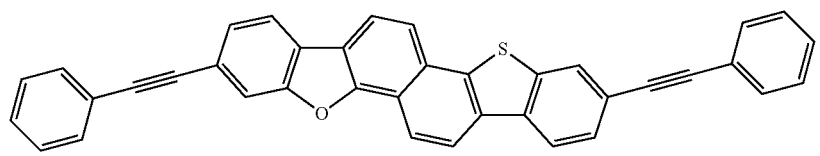
(B172)
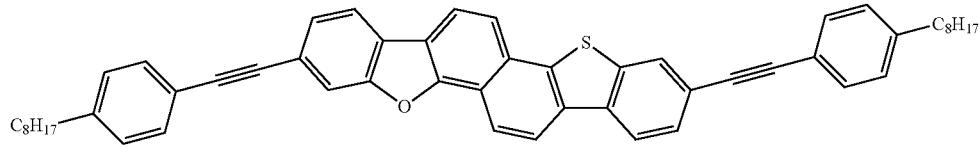
(B173)
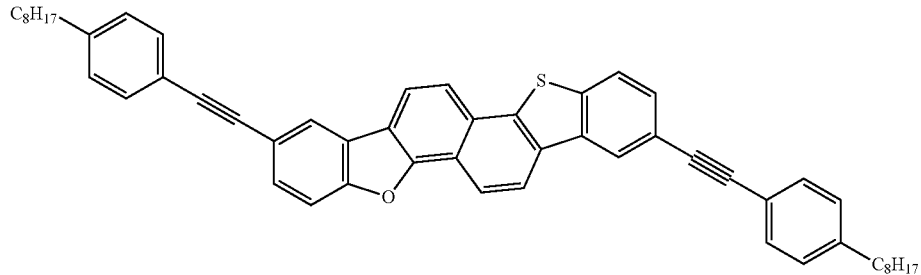
(B174)
(B175)
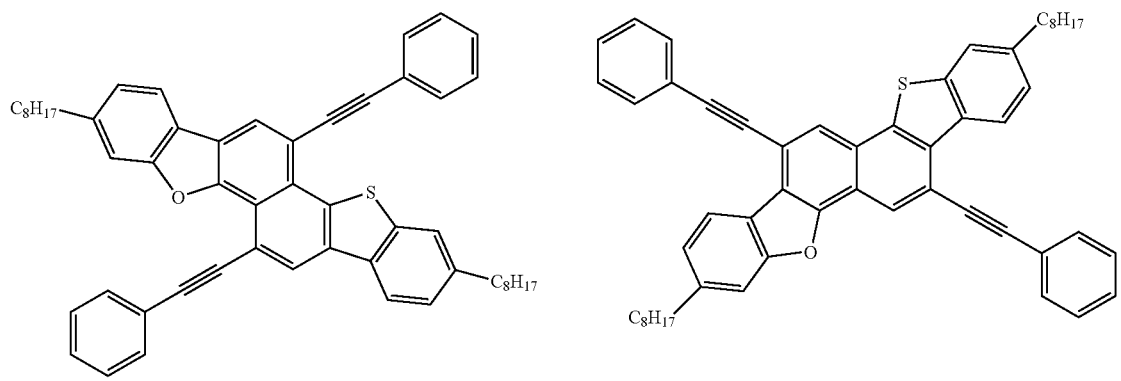

(B176)
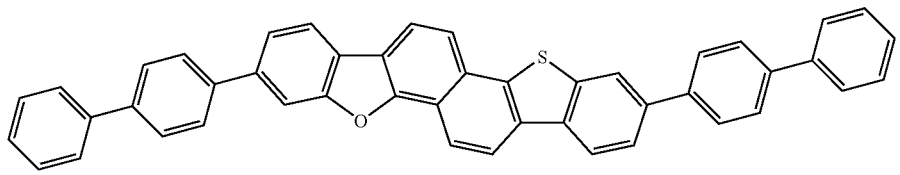
(B177)
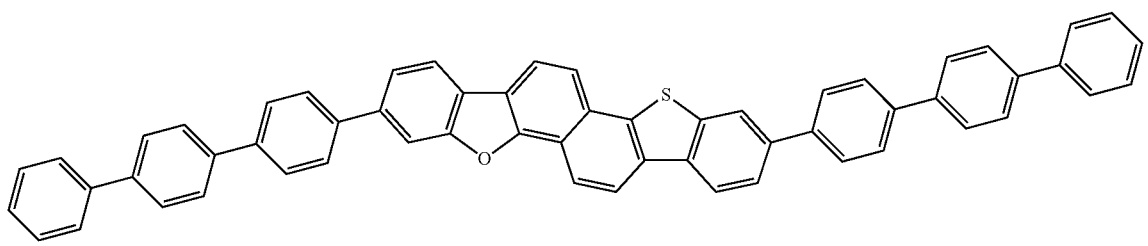
(B178)
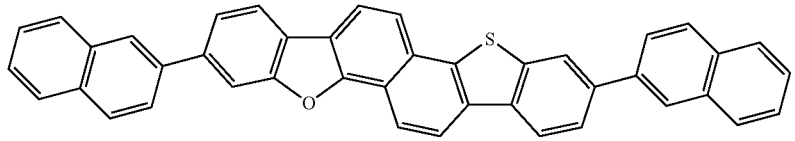
(B179)
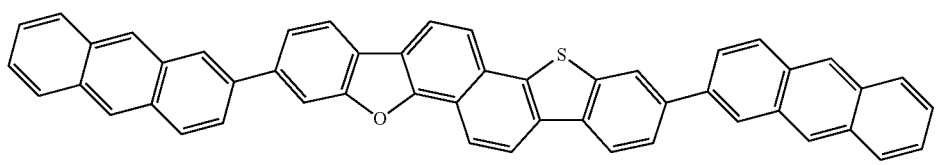
(B180)
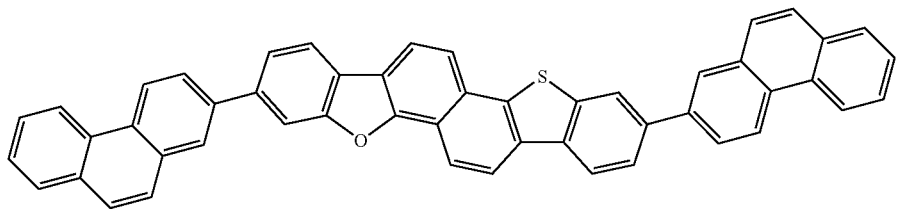
(B181)
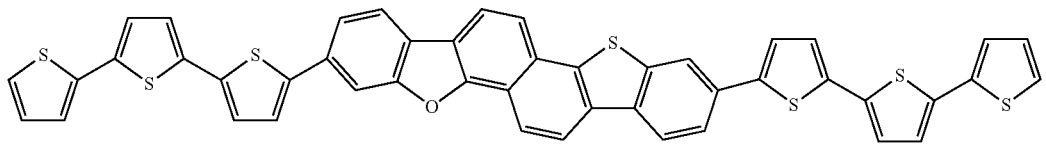
(B182)
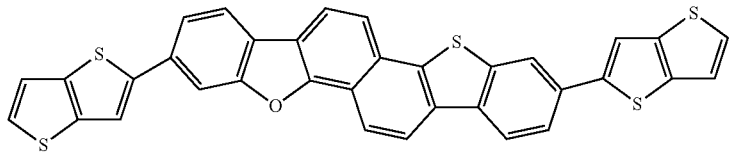
(B183)
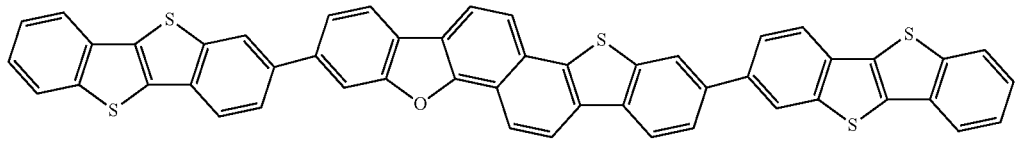
(B184)
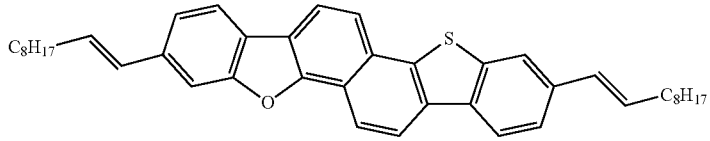

-continued
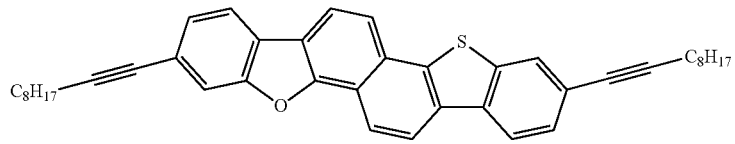
(B185)
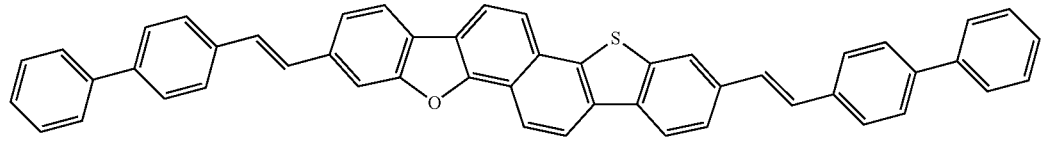
(B186)
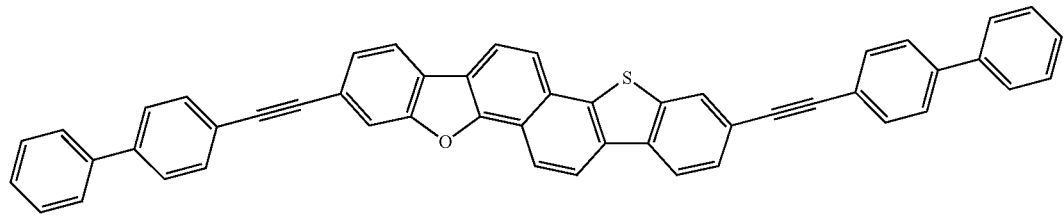
(B187)
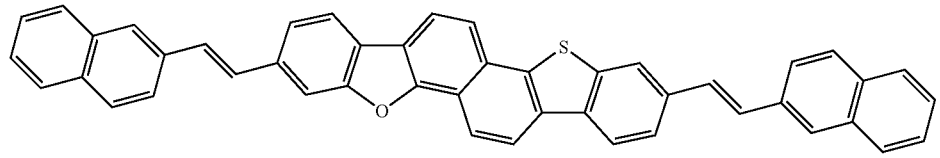
(B188)
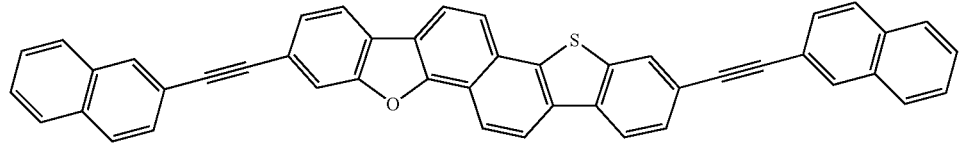
(B189)
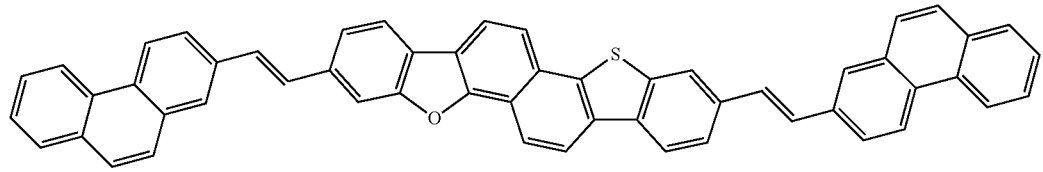
(B190)
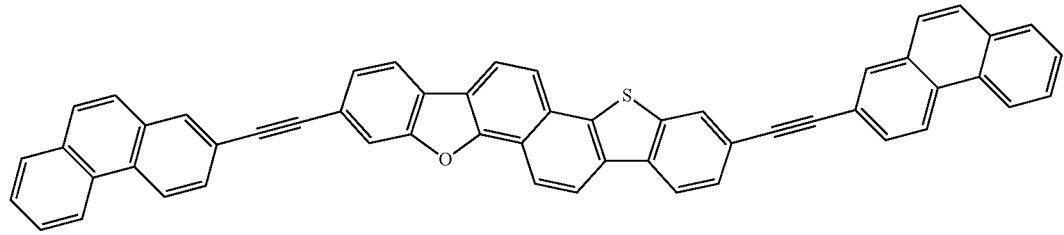
(B191)
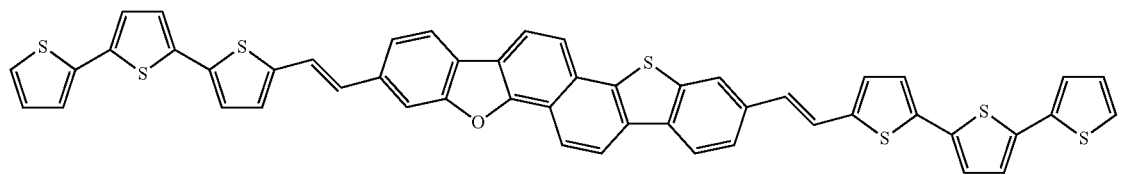
(B192)

(B193)
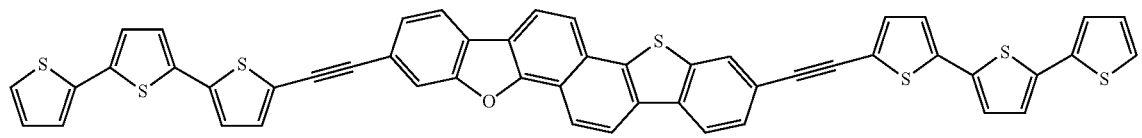
(B194)
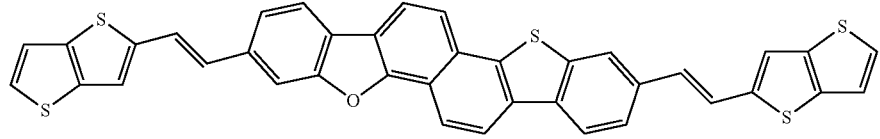
(B195)
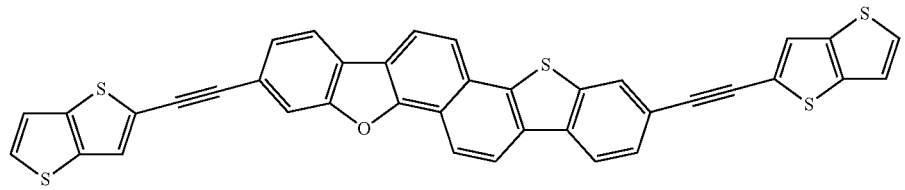
(B196)
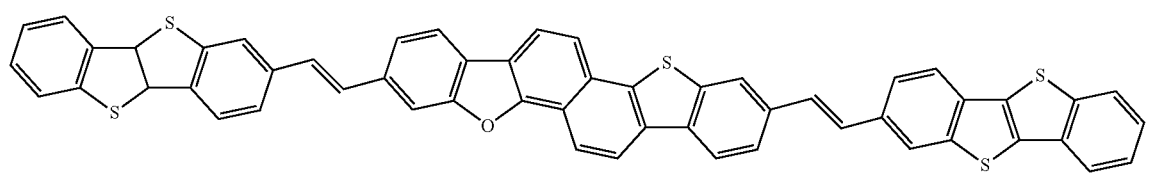
(B197)
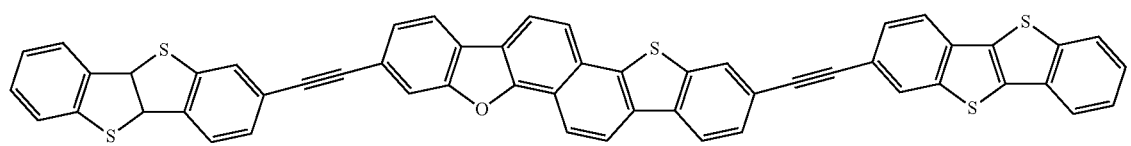
(B198)
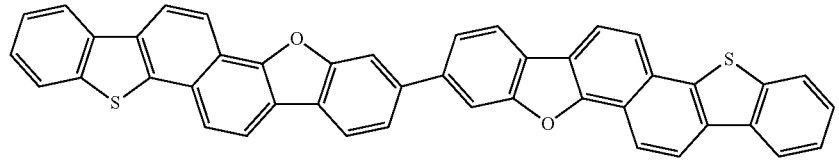
(B199)
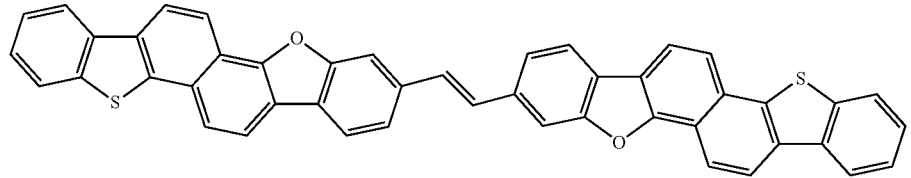
(B200)
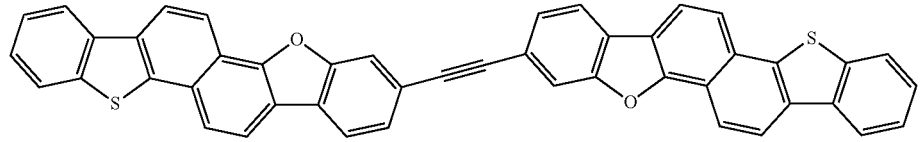

-continued
(B201)
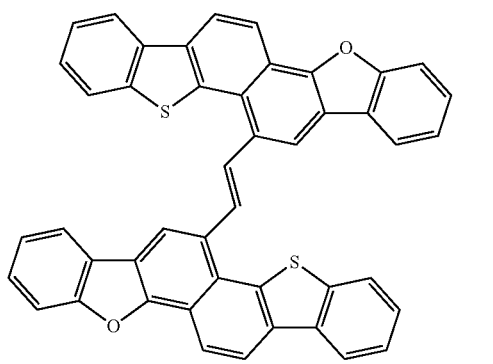
(B202)
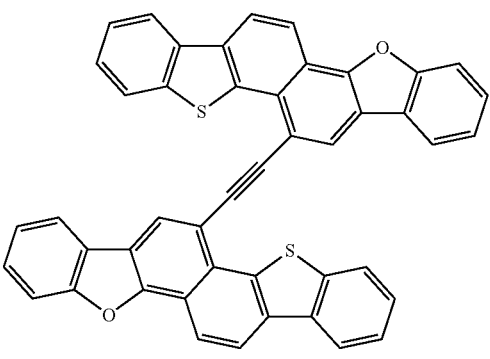
(B203)
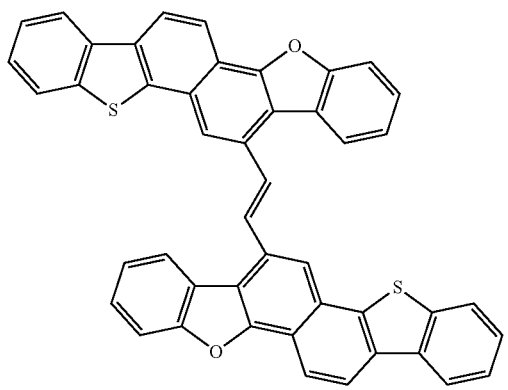
(B204)
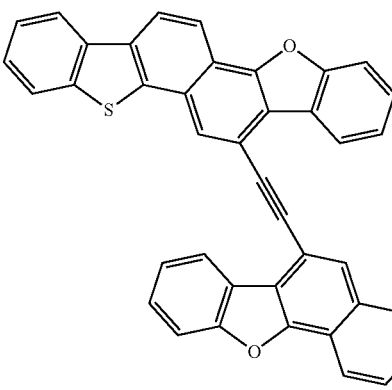
(B205)
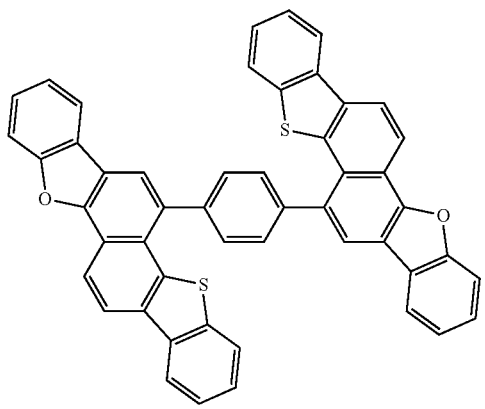
(B206)
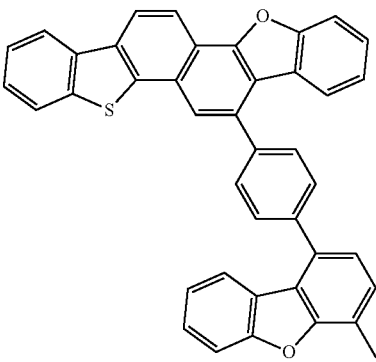
(B207)
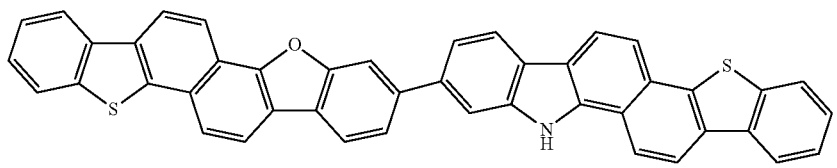
(B208)
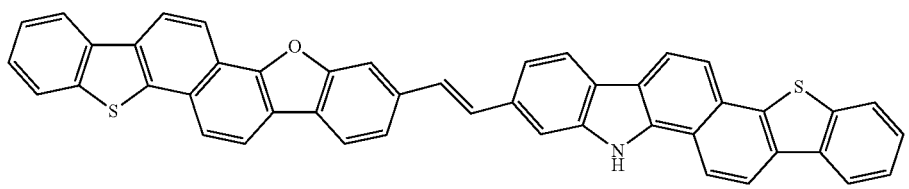

-continued
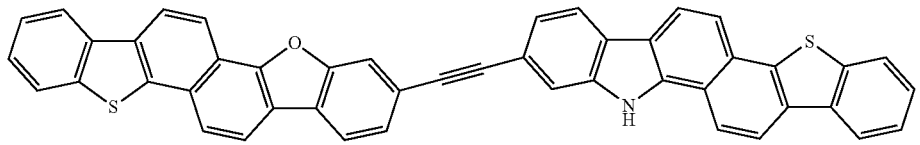
(B209)
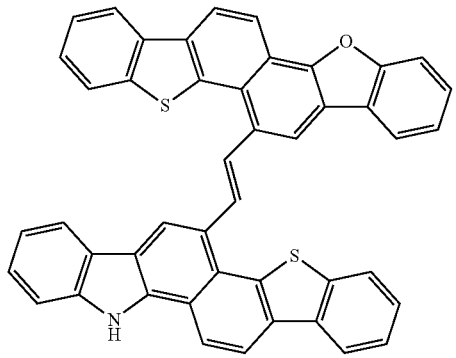
(B210)
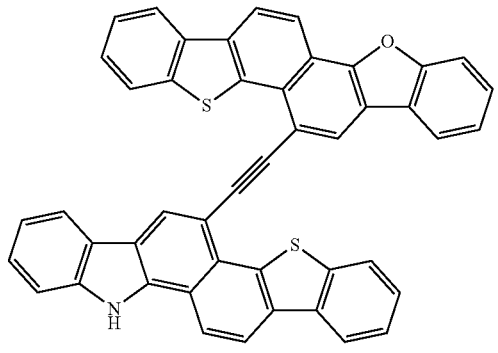
(B211)
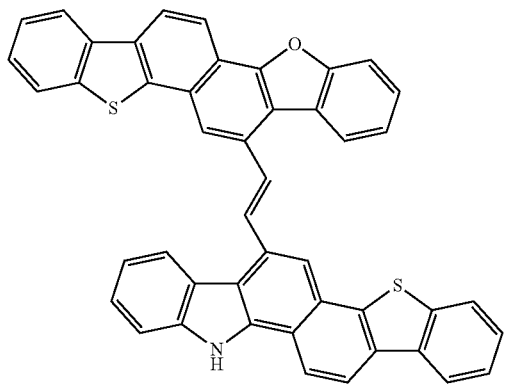
(B212)
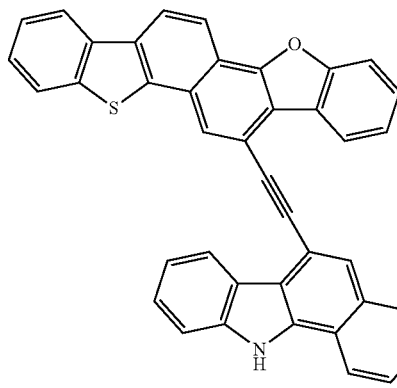
(B213)
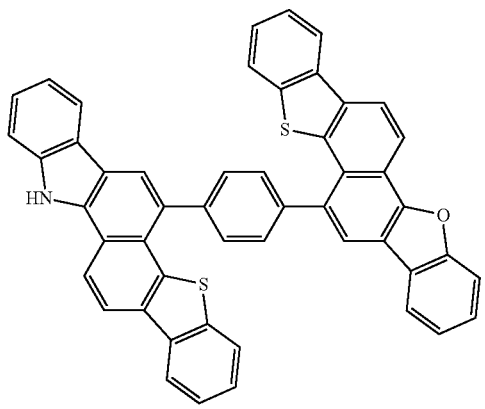
(B214)
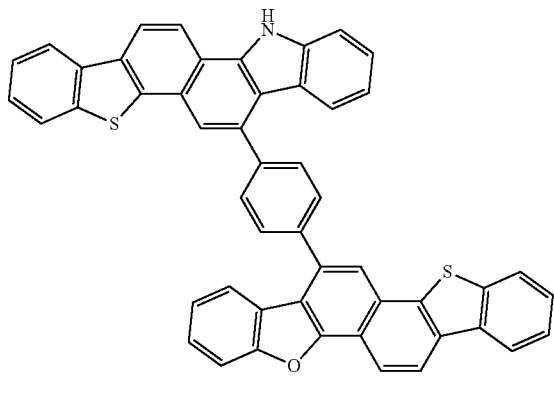
(B215)
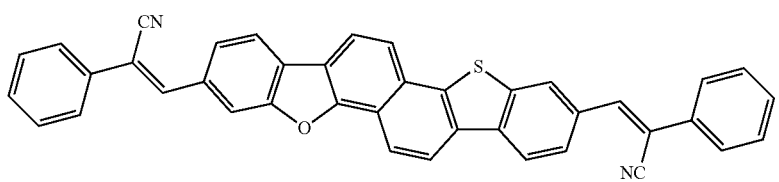
(B216)

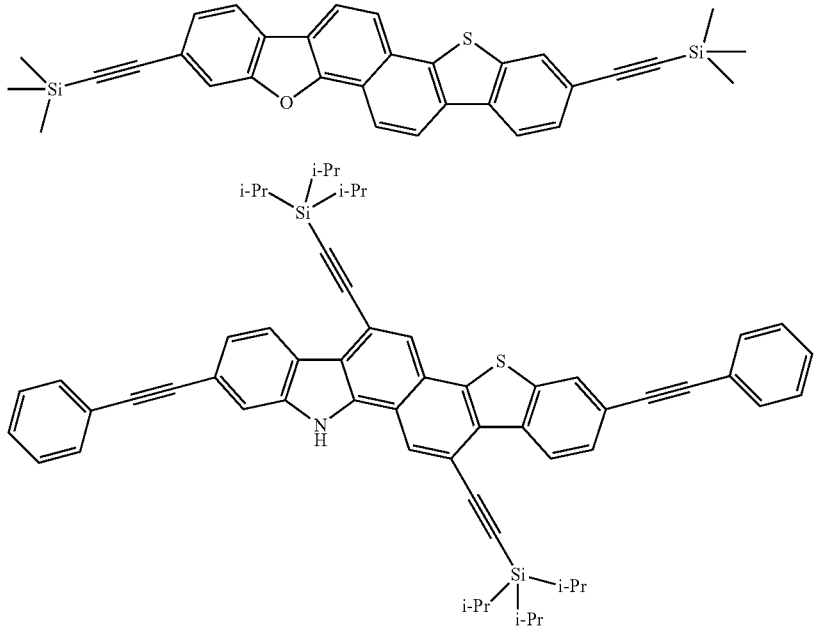

An organic semiconductor material of the present invention contains the aromatic heterocyclic compound (1) of the general formula (1). The organic semiconductor material of the present invention preferably contains the compound at 50 wt % or more, and more preferably contains the compound at 90 wt % or more. It is also preferred that the aromatic heterocyclic compound (1) itself be the organic semiconductor material. A component to be contained in the organic semiconductor material together with the aromatic heterocyclic compound (1) is not particularly limited as long as performance as the organic semiconductor material is not impaired, but an organic semiconductor material formed of a charge-transporting compound is preferred.

An organic semiconductor film of the present invention is formed of the organic semiconductor material. The organic semiconductor film is advantageously formed through a step of applying and drying a solution prepared by dissolving the organic semiconductor material in an organic solvent. The organic semiconductor film is useful as an organic semiconductor layer in an organic semiconductor device.

Next, an organic semiconductor device including an organic semiconductor material formed of the organic semiconductor material of the present invention is described by taking an organic field-effect transistor device (OTFT device) as an example with reference to FIG. 1 to FIG. 4.

FIG. 1, FIG. 2, FIG. 3, and FIG. 4 are each an illustration of an OTFT device according to an embodiment of the present invention, and are each a schematic sectional view for illustrating the structure of an OTFT device.

In an OTFT device illustrated in FIG. 1, a gate electrode 2 is arranged on the surface of a substrate 1, an insulating film layer 3 is formed on the gate electrode 2, a source electrode 5 and a drain electrode 6 are formed on the insulating film layer 3, and an organic semiconductor layer 4 is further formed thereon.

Figure 2:
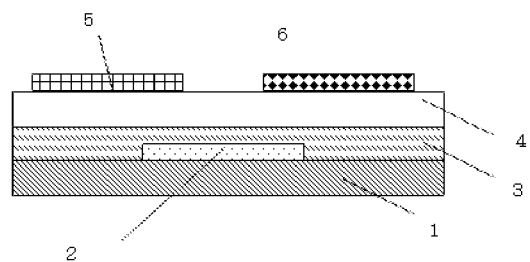
FIG. 2 is a schematic sectional view for illustrating another example of the organic field-effect transistor device.

In an OTFT device illustrated in FIG. 2, the gate electrode 2 is arranged on the surface of the substrate 1, the insulating film layer 3 is formed on the gate electrode 2, the organic semiconductor layer 4 is formed thereon, and the source electrode 5 and the drain electrode 6 are formed on the organic semiconductor layer 4.

Figure 3:
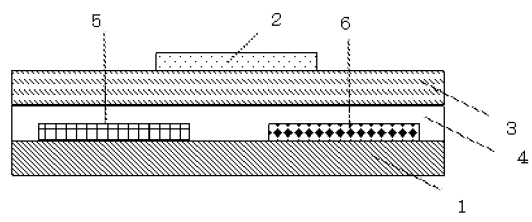
FIG. 3 is a schematic sectional view for illustrating another example of the organic field-effect transistor device.

In an OTFT device illustrated in FIG. 3, the source electrode 5 and the drain electrode 6 are formed on the surface of the substrate 1, and the gate electrode 2 is formed at the outermost surface through the intermediation of the organic semiconductor layer 4 and the insulating film layer 3.

Figure 4:
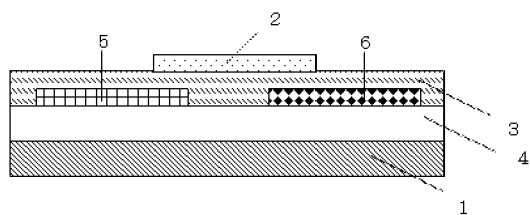
FIG. 4 is a schematic sectional view for illustrating another example of the organic field-effect transistor device.

In the case of an OTFT device illustrated in FIG. 4, in an organic semiconductor device according to the present invention, the organic semiconductor layer 4, the source electrode 5, and the drain electrode 6 are formed on the surface of the substrate 1, and the gate electrode 2 is formed at the outermost surface through the intermediation of the insulating film layer 3.

As a material to be used as the substrate 1, there are given, for example: ceramics substrates formed of glass, quartz, aluminum oxide, sapphire, silicon nitride, silicon carbide, and the like; semiconductor substrates formed of silicon, germanium, gallium arsenide, gallium phosphide, gallium nitride, and the like; and resin substrates formed of polyester such as polyethylene terephthalate or polynaphthalene terephthalate, polyethylene, polypropylene, polyvinyl alcohol, an ethylene vinyl alcohol copolymer, cyclic polyolefin, polyimide, polyamide, polystyrene, and the like. The thickness of the substrate may be set to from about 10 μm to about 2 mm. In particular, in the case of a flexible plastic substrate, the thickness may be set to, for example, from about 50 μm to about 100 μm, and in the case of a rigid substrate, such as a glass plate or a silicon wafer, the thickness may be set to from about 0.1 mm to about 2 mm.

The gate electrode 2 may be, for example, a metal thin film, a conductive polymer film, or a conductive film formed from a conductive ink or paste. Alternatively, for example, a substrate itself like heavily doped silicon may be used as the gate electrode. As a material for the gate electrode, there may be given, for example, aluminum, copper, stainless steel, gold, chromium, an n-doped or p-doped silicon, an indium tin oxide, a conductive polymer such as polystyrenesulfonic acid-doped poly(3,4-ethylenedioxythiophene), a conductive ink/paste containing carbon black/graphite, and one obtained by dispersing colloidal silver into a polymer binder.

The gate electrode 2 may be produced by using, for example, vacuum deposition, sputtering of a metal or a conductive metal oxide, or spin coating, inkjet, spraying, coating, or casting of a conductive polymer solution or a conductive ink. The thickness of the gate electrode 2 preferably falls within, for example, the range of from about 10 nm to about 10 μm.

The insulating film layer 3 may be generally an inorganic material film or an organic polymer film. As an inorganic material suitable as the insulating film layer 3, there may be given, for example, silicon oxide, silicon nitride, aluminum oxide, barium titanate, and barium zirconium titanate. As an organic compound suitable as the insulating film layer 3, there are given, for example, polyester, polycarbonate, poly(vinylphenol), polyimide, polystyrene, poly(methacrylate), poly(acrylate), and an epoxy resin. In addition, an insulating layer film obtained by dispersing an inorganic material in an organic polymer may be used. The thickness of the insulating film layer varies depending on the dielectric constant of an insulating material to be used, but is, for example, from about 10 nm to about 10 μm.

As means for forming the insulating film layer, there are given, for example: a dry film-forming method, such as a vacuum deposition method, a CVD method, a sputtering method, and a laser deposition method; and a wet film-forming method, such as a spin coating method, a blade coating method, a screen printing, inkjet printing, and a stamp method, and the means may be used depending on the material.

The source electrode 5 and the drain electrode 6 may each be formed from a material which provides low-resistance ohmic contact to the organic semiconductor layer 4 to be described later. As materials preferred as the source electrode 5 and the drain electrode 6, those given as materials preferred for the gate electrode 2 may be used, and examples thereof include gold, nickel, aluminum, platinum, a conductive polymer, and a conductive ink. The thickness of each of the source electrode 5 and the drain electrode 6 is typically, for example, from about 40 nm to about 10 μm, and the thickness is more preferably from about 10 nm to about 1 μm.

As means for forming each of the source electrode 5 and the drain electrode 6, for example, there are given a vacuum deposit ion method, a sputtering method, an application method, a thermal transfer method, a printing method, and a sol-gel method. At the time of film formation or after film formation, patterning is preferably performed as required. As a method for the patterning, for example, there is given a photolithography method involving a combination of patterning and etching of a photoresist. In addition, the patterning may also be performed by utilizing, for example, a printing method, such as inkjet printing, screen printing, or offset printing, a soft lithography method such as a microcontact printing method, or a method involving a combination of a plurality of these methods.

As means for forming the organic semiconductor layer 4, for example, there are given: a dry film-forming method, such as a vacuum deposition method, a CVD method, a sputtering method, or a laser deposition method; and a wet film-forming method, which involves applying a solution or a dispersion onto a substrate, and then removing a solvent or a dispersion medium to form a thin film. Of those, a wet film-forming method is preferably used. Examples of the wet film-forming method may include a spin coating method, a blade coating method, screen printing, inkjet printing, and a stamp method. For example, when the spin coating method is used, the organic semiconductor material of the present invention is dissolved in an appropriate solvent in which the organic semiconductor material has solubility, to thereby prepare a solution having a concentration of from 0.01 wt % to 10 wt %, and then the solution of the organic semiconductor material is dropped onto the insulating film layer 3 formed on the substrate 1, followed by rotating the resultant at from 500 rotations/min to 6,000 rotations/min for from 5 sec to 120 sec. The solvent is selected depending on the solubility of the organic semiconductor material in each solvent and film quality after film formation, and there may be used a solvent selected from, for example: water; alcohols typified by methanol; aromatic hydrocarbons typified by toluene; aliphatic hydrocarbons typified by hexane, cyclohexane, and the like; organic nitro compounds such as nitromethane and nitrobenzene; cyclic ether compounds such as tetrahydrofuran and dioxane; nitrile-based compounds such as acetonitrile and benzonitrile; ketones such as acetone and methyl ethyl ketone; esters such as ethyl acetate; and aprotic polar solvents typified by dimethyl sulfoxide, dimethylacetamide, sulfolane, N-methylpyrrolidone, dimethylimidazolidinone, and the like. In addition, two or more kinds of those solvents may be used in combination.

An organic field-effect transistor device using the organic semiconductor material of the present invention may be produced by the method described above. In the obtained organic field-effect transistor device, the organic semiconductor layer forms a channel region, and on-off operation is performed through the control of a current flowing between the source electrode and the drain electrode based on a voltage to be applied to the gate electrode.

As an organic semiconductor device according to another preferred embodiment of the present invention obtained from the organic semiconductor material of the present invention, there is given an organic photovoltaic device. Specifically, the organic semiconductor device is an organic photovoltaic device including, on a substrate, a positive electrode, an organic semiconductor layer, and a negative electrode, in which the organic semiconductor layer contains the organic semiconductor material of the present invention described above.

The structure of the organic photovoltaic device of the present invention is described with reference to the drawings, but the structure of the organic photovoltaic device of the present invention is by no means limited to those illustrated in the drawings.

Figure 5:
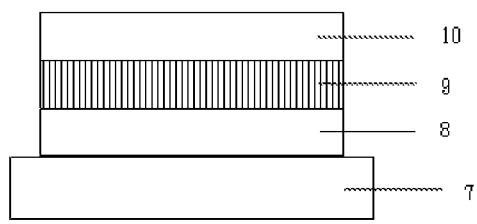
FIG. 5 is a schematic sectional view for illustrating another example of the organic field-effect transistor device.
Figure 6:
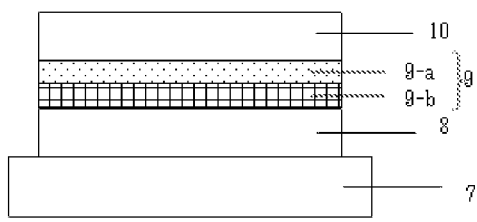
FIG. 6 is a schematic sectional view for illustrating another example of the organic field-effect transistor device.

FIG. 5 is a sectional view for illustrating an example of the structure of a general organic photovoltaic device to be used in the present invention. Reference numeral 7 represents the substrate, reference numeral 8 represents the positive electrode, reference numeral 9 represents the organic semiconductor layer, and reference numeral 10 represents the negative electrode. In addition, FIG. 6 is a sectional view for illustrating an example of the structure in the case where organic semiconductor layers are laminated. Reference symbol 9-*a* represents a p-type organic semiconductor layer and reference symbol 9-*b* represents an n-type organic semiconductor layer.

The substrate is not particularly limited and may adopt, for example, a hitherto known construction. A glass substrate or a transparent resin film having mechanical and thermal strengths, and having transparency is preferably used. Examples of the transparent resin film include polyethylene, an ethylene-vinyl acetate copolymer, an ethylene-vinyl alcohol copolymer, polypropylene, polystyrene, polymethyl methacrylate, polyvinyl chloride, polyvinyl alcohol, polyvinyl butyral, nylon, polyether ether ketone, polysulfone, polyether sulfone, a tetrafluoroethylene-perfluoroalkyl vinyl ether copolymer, polyvinyl fluoride, a tetrafluoroethylene-ethylene copolymer, a tetrafluoroethylene-hexafluoropropylene copolymer, polychlorotrifluoroethylene, polyvinylidene fluoride, polyester, polycarbonate, polyurethane, polyimide, polyether imide, polyimide, and polypropylene.

It is preferred that a conductive material having a large work function be used as an electrode material for one electrode, and a conductive material having a small work function be used as an electrode material for the other electrode. The electrode using the conductive material having a large work function serves as the positive electrode. As the conductive material having a large work function, there is preferably used a metal oxide of, for example, indium or tin, or a composite metal oxide thereof (such as indium tin oxide (ITO) or indium zinc oxide (IZO)) having transparency as well as a metal such as gold, platinum, chromium, or nickel. In this case, the conductive material to be used in the positive electrode is preferably capable of ohmic junction with the organic semiconductor layer. Further, when a hole-transporting layer to be described later is used, the conductive material to be used in the positive electrode is preferably capable of ohmic junction with the hole-transporting layer.

The electrode using the conductive material having a small work function serves as the negative electrode. As the conductive material having a small work function, there is used an alkali metal or an alkaline earth metal, specifically lithium, magnesium, or calcium. In addition, tin, silver, or aluminum is also preferably used. Further, alloys formed of the metals and electrodes formed of laminates of the metals are also each preferably used. In addition, a metal fluoride, such as lithium fluoride or cesium fluoride, may be introduced into an interface between the negative electrode and an electron-transporting layer to increase an extracted current. In this case, the conductive material to be used in the negative electrode is preferably capable of ohmic junction with the organic semiconductor layer. Further, when the electron-transporting layer to be described later is used, the conductive material to be used in the negative electrode is preferably capable of ohmic junction with the electron-transporting layer.

The organic semiconductor layer contains the aromatic heterocyclic compound (1). That is, the organic semiconductor layer is formed by using the organic semiconductor material of the present invention containing the aromatic heterocyclic compound represented by the general formula (1). The organic semiconductor material of the present invention is used for a p-type organic semiconductor material (hereinafter referred to as p-type organic material), an n-type organic semiconductor material (hereinafter referred to as n-type organic material), or both. Two or more kinds of aromatic heterocyclic compounds (1) may be used as follows: one or more thereof are used as p-type organic material components, and other one or more thereof are used as n-type organic material components. In addition, one of the p-type organic material or the n-type organic material may be a compound free of the aromatic heterocyclic compound (1).

The organic semiconductor layer is formed by using the organic semiconductor material containing at least one compound represented by the formula (1). The compound represented by the formula (1) functions as the p-type organic material or the n-type organic material.

The p-type organic material and the n-type organic material are preferably mixed, and it is preferred that the p-type organic material and the n-type organic material be compatible with each other, or undergo phase separation, at a molecular level. The domain size of the phase-separated structure is not particularly limited, but is generally a size of 1 nm or more and 50 nm or less. In addition, when the p-type organic material and the n-type organic material are laminated, it is preferred that a layer containing the p-type organic material be on a positive electrode side and a layer containing the n-type organic material be on a negative electrode side. The organic semiconductor layer has a thickness of preferably from 5 nm to 500 nm, more preferably from 30 nm to 300 nm. When the layers are laminated, the layer containing the p-type organic material of the present invention has a thickness of preferably from 1 nm to 400 nm, more preferably from 15 nm to 150 nm out of the above-mentioned thickness.

The p-type organic material may use an aromatic heterocyclic compound (1) which shows a p-type semiconductor characteristic alone, or may contain any other p-type organic material. Examples of the other p-type organic material include: conjugated polymers, such as a polythiophene-based polymer, a benzothiadiazole-thiophene-based derivative, a benzothiadiazole-thiophene-based copolymer, a poly-p-phenylene vinylene-based polymer, a poly-p-phenylene-based polymer, a polyfluorene-based polymer, a polypyrrole-based polymer, a polyaniline-based polymer, a polyacetylene-based polymer, and a polythienylene vinylene-based polymer; and low-molecular weight organic compounds, such as phthalocyanine derivatives, e.g., H2 phthalocyanine (H2Pc), copper phthalocyanine (CuPc), and zinc phthalocyanine (ZnPc), porphyrin derivatives, triarylamine derivatives, e.g., N,N'-diphenyl-N,N'-di(3-methylphenyl)-4,4'-diphenyl-1,1'-diamine (TPD) and N,N'-di-naphthyl-N,N'-diphenyl-4,4'-diphenyl-1,1'-diamine (NPD), carbazole derivatives, e.g., 4,4'-di(carbazol-9-yl)biphenyl (CBP), and oligothiophene derivatives (e.g., terthiophene, quaterthiophene, sexithiophene, and octithiophene).

The n-type organic material may use an aromatic heterocyclic compound (1) which shows an n-type semiconductor characteristic alone, or may use any other n-type organic material. Examples of the other n-type organic material include 1,4,5,8-naphthalenetetracarboxylic dianhydride (NTCDA), 3,4,9,10-perylenetetracarboxylic dianhydride (PTCDA), 3,4,9,10-perylenetetracarboxylic bisbenzimidazole (PTCBI), N,N'-dioctyl-3,4,9,10-naphthyltetracarboxydiimide (PTCDI-C8H), oxazole derivatives, such as 2-(4-biphenylyl)-5-(4-t-butylphenyl)-1,3,4-oxadiazole (PBD) and 2,5-di(1-naphthyl)-1,3,4-oxadiazole (BND), triazole derivatives, such as 3-(4-biphenylyl)-4-phenyl-5-(4-t-butylphenyl)-1,2,4-triazole (TAZ), phenanthroline derivatives, phosphine oxide derivatives, fullerene compounds (such as unsubstituted fullerene compounds typified by C60, C70, C76, C78, C82, C84, C90, and C94 fullerenes, and [6,6]-phenyl C61 butyric acid methyl ester ([6,6]-PCBM), [5,6]-phenyl C61 butyric acid methyl ester ([5,6]-PCBM), [6,6]-phenyl C61 butyric acid hexyl ester ([6,6]-PCBH), [6,6]-phenyl C61 butyric acid dodecyl ester ([6,6]-PCBD), phenyl C71 butyric acid methyl ester (PC70BM), and phenyl C85 butyric acid methyl ester (PC84BM)), a carbon nanotube (CNT), and derivatives each obtained by introducing a cyano group into a poly-p-phenylene vinylene-based polymer (CN-PPV).

In the organic photovoltaic device of the present invention, the hole-transporting layer may be formed between the positive electrode and the organic semiconductor layer. As a material for forming the hole-transporting layer, there is preferably used a conductive polymer, such as a polythiophene-based polymer, a poly-p-phenylenevinylene-based polymer, or a polyfluorene-based polymer, or a low-molecular weight organic compound showing a p-type semiconductor characteristic, such as a phthalocyanine derivative (e.g., H2Pc, CuPc, or ZnPc) or a porphyrin derivative. In particular, polyethylenedioxythiophene (PEDOT) as a polythiophene-based polymer or PEDOT having added thereto polystyrene sulfonate (PSS) is preferably used. The hole-transporting layer has a thickness of preferably from 5 nm to 600 nm, more preferably from 30 nm to 200 nm.

In addition, in the organic photovoltaic device of the present invention, the electron-transporting layer may be formed between the organic semiconductor layer and the negative electrode. A material for forming the electron-transporting layer is not particularly limited, but it is preferred to use an organic material showing an n-type semiconductor characteristic like the above-mentioned n-type organic materials (such as NTCDA, PTCDA, PTCDI-C8H, the oxazole derivative, the triazole derivative, the phenanthroline derivative, the phosphine oxide derivative, the fullerene compound, the CNT, and the CN-PPV). The electron-transporting layer has a thickness of preferably from 5 nm to 600 nm, more preferably from 30 nm to 200 nm.

In addition, in the organic photovoltaic device of the present invention, two or more organic semiconductor layers may be laminated (put in tandem) through the intermediation of one or more intermediate electrodes to form series junction. An example of the laminate construction may be as follows: "substrate/positive electrode/first organic semiconductor layer/intermediate electrode/second organic semiconductor layer/negative electrode." Such lamination can increase an open-circuit voltage. It should be noted that the hole-transporting layer may be formed between the positive electrode and the first organic semiconductor layer, and between the intermediate electrode and the second organic semiconductor layer, or the hole-transporting layer may be formed between the first organic semiconductor layer and the intermediate electrode, and between the second organic semiconductor layer and the negative electrode.

In the case of such laminate construction, it is preferred that at least one layer of the organic semiconductor layers contain the compound of the present invention represented by the formula (1) and the other layer contain a p-type organic material having a band gap different from that of the p-type organic material of the present invention in order to prevent a reduction in short-circuit current. Examples of such p-type organic material include: the above-mentioned conjugated polymers, such as a polythiophene-based polymer, a poly-p-phenylene vinylene-based polymer, a poly-p-phenylene-based polymer, a polyfluorene-based polymer, a polypyrrole-based polymer, a polyaniline-based polymer, a polyacetylene-based polymer, and a polythienylene vinylene-based polymer; and low-molecular weight organic compounds, such as phthalocyanine derivatives, e.g., H2 phthalocyanine (H2Pc), copper phthalocyanine (CuPc), and zinc phthalocyanine (ZnPc), porphyrin derivatives, triarylamine derivatives, e.g., N,N'-diphenyl-N,N'-di(3-methylphenyl)-4,4'-diphenyl-1,1'-diamine (TPD) and N,N'-dinaphthyl-N,N'-diphenyl-4,4'-diphenyl-1,1'-diamine (NPD), carbazole derivatives, e.g., 4,4'-di(carbazol-9-yl) biphenyl (CEP), and oligothiophene derivatives (e.g., terthiophene, quaterthiophene, sexithiophene, and octithiophene).

In addition, a highly conductive material is preferred as a material for the intermediate electrode used herein, and examples thereof include: the above-mentioned metals such as gold, platinum, chromium, nickel, lithium, magnesium, calcium, tin, silver, and aluminum; metal oxides of, for example, indium or tin and composite metal oxides thereof (such as indium tin oxide (ITO) and indium zinc oxide (IZO)) having transparency; alloys formed of the metals; laminates of the metals; polyethylenedioxythiophene (PEDOT); and PEDOT having added thereto polystyrenesulfonate (PSS). The intermediate electrode preferably has light permeability, and sufficient light permeability can be secured by reducing its thickness in many cases even when the intermediate electrode is made of a material like a metal having low light permeability.

The organic semiconductor layer may be formed using any method such as spin coating application, blade coating application, slid die coating application, screen printing application, bar coater application, cast application, a printing transfer method, a dip-pulling method, an inkjet method, a spraying method, and a vacuum deposition method. A formation method may be selected depending on organic semiconductor layer characteristics to be obtained, such as thickness control and orientation control.

An organic semiconductor device of the present invention uses the organic semiconductor material of the present invention. The organic semiconductor device is preferably an organic field-effect transistor or an organic photovoltaic device.

EXAMPLES

The present invention is described in more detail by way of Examples below. It should be appreciated that the present invention is not limited to these Examples and may be carried out in various forms as long as the various forms do not deviate from the gist of the present invention. It should be noted that numbers of compounds correspond to the numbers described in the chemical formulae.

Example 1

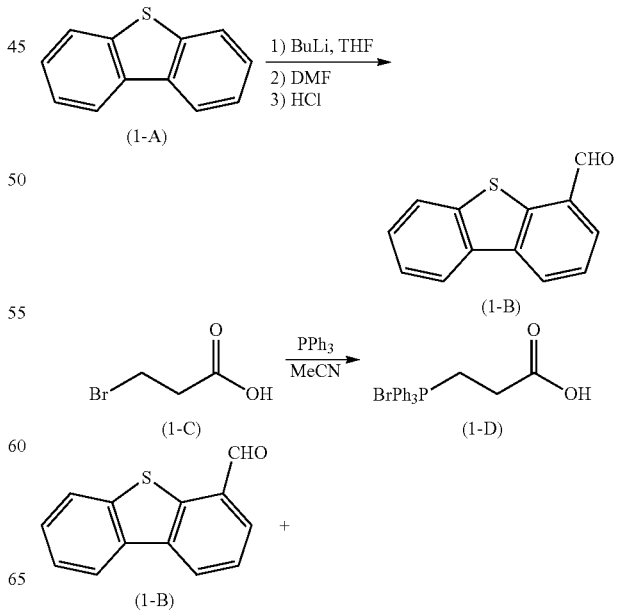

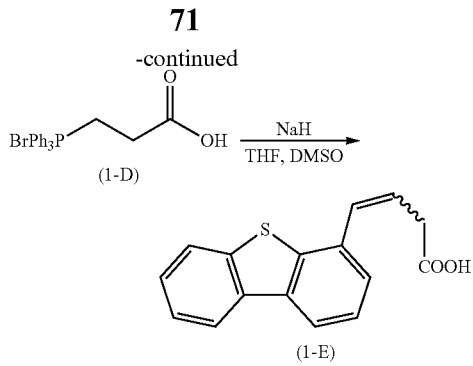

Under a stream of nitrogen gas, a 1,000-mL reaction vessel was loaded with dibenzothiophene (1-A) (109 mmol, 20.0 g) and anhydrous THF (100 mL), and the mixture was stirred at 0° C. for 30 min. To the mixture, a 2 N BuLi-hexane solution (60 mL, 156 mmol) was added dropwise. After the completion of the dropwise addition, the mixture was heated to reflux for 6 hr. After cooling to room temperature, anhydrous DMF (20 mL, 160 mmol) was added dropwise, and then the mixture was stirred overnight at room temperature. The reaction mixture was poured into 6 N hydrochloric acid (500 mL) and extracted with acetic acid, and the organic layer was washed with water and dried. Column chromatography was performed to provide 8.0 g of Compound (1-B).

Under a stream of nitrogen gas, a 500-mL reaction vessel was loaded with 3-bromopropionic acid (1-C) (169 mmol, 25 g), triphenylphosphine (196 mmol, 51.42 g), and anhydrous acetonitrile (70 mL). After the completion of the addition, the mixture was stirred under heating to reflux for 5 hr. The reaction liquid was allowed to cool to room temperature, and then concentrated. The resultant solid was washed with ethyl acetate to provide 65.2 g of wittig-salt (1-D).

Under a stream of nitrogen gas, a 500-mL reaction vessel was loaded with Compound (1-B) (37.7 mmol, 8.0 g), wittig-salt (1-D) (3,377 mmol, 1,402 g), anhydrous THF (75 mL), and anhydrous DMSO (75 mL), and the mixture was stirred at 27° C. (water bath) for 30 min. Into the mixture, 60% sodium hydride (112.1 mmol, 3.5 g) was poured in small portions, and the mixture was stirred for 6 hr. The reaction mixture was poured into a 2 N sodium hydroxide aqueous solution and washed with ethyl acetate, and the ethyl acetate layer was extracted with a 2 N sodium hydroxide aqueous solution. The combined aqueous layer was adjusted to a pH of 1 by the addition of 6N-hydrochloric acid, and extracted with ethyl acetate. The organic layer was washed with water, and the solvent was evaporated to provide 9.6 g of Compound (1-E).

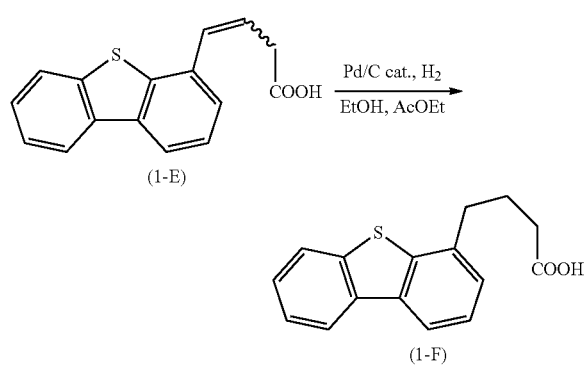

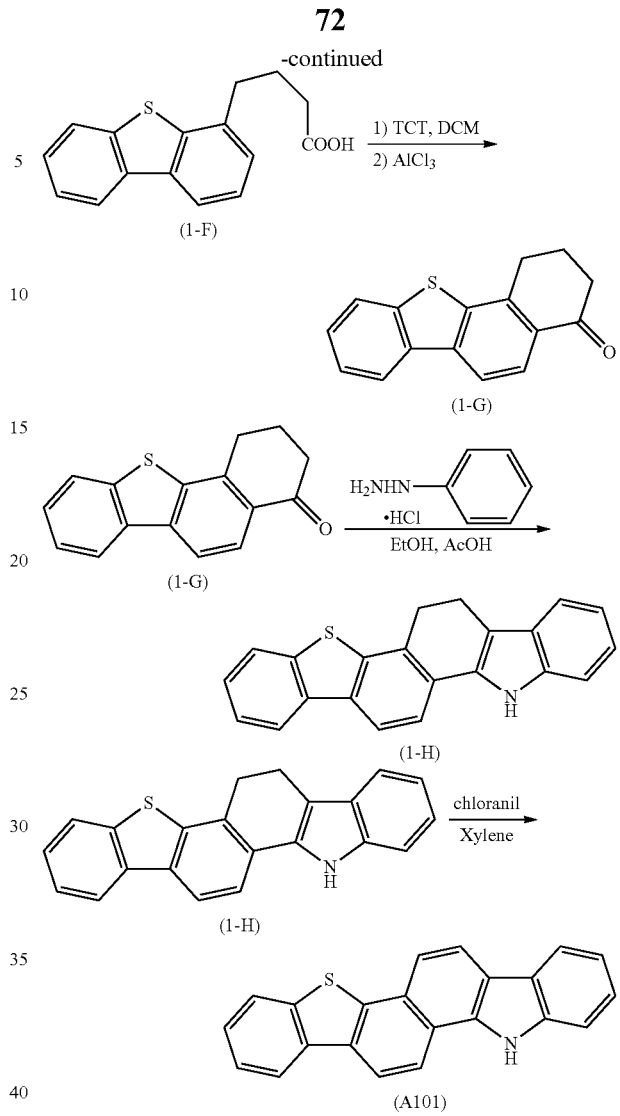

Under a stream of nitrogen gas, a 300-mL reaction vessel was loaded with Compound (1-E) (35 mmol, 9.4 g), anhydrous ethanol (50 mL), anhydrous ethyl acetate (50 mL), and 10% Pd/C (0.5 g), and nitrogen was performed for 10 min. A hydrogen bubbler was used to blow hydrogen gas into the solvent at room temperature for 10 hr. Further, 10% Pd/C (0.5 g) was added, and hydrogen was blown for 9 hr. After the completion of the reaction, the catalyst was separated by filtration, and then the solvent was evaporated to provide 8.8 g of Compound (1-F).

Under a stream of nitrogen gas, a 200-mL reaction vessel was loaded with Compound (1-F) (32.6 mmol, 8.8 g), 2,4,6-trichloro-1,3,5-triazine (65.1 mmol, 12.0 g), and anhydrous dichloromethane (50 mL), and the mixture was stirred at room temperature for 5 min. After that, anhydrous pyridine (97.7 mmol, 7.7 g) was slowly poured at room temperature, and the mixture was stirred for 8 hr. Subsequently, aluminum chloride (65.1 mmol, 8.7 g) was slowly added at room temperature, and the mixture was stirred for 4 hr. After the completion of the reaction, the resultant was poured into 1 N HCl, and extracted with chloroform. The organic layer was washed with water and dried, and the solvent was evaporated, followed by column chromatography to provide 3.3 g of Compound (1-G).

Figure 7:
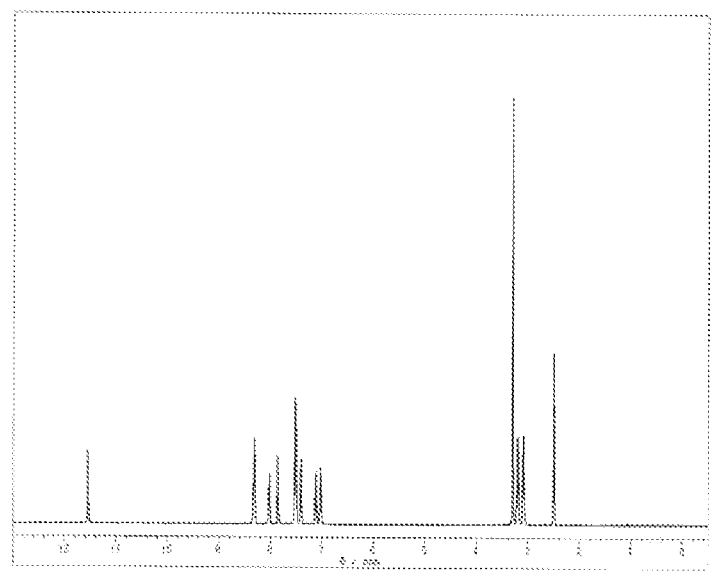
FIG. 7 is an NMR spectrum of Compound (1-H).

Under a stream of nitrogen gas, a 50-mL reaction vessel was loaded with Compound (1-G) (6.0 mmol, 2.5 g) and a solution of phenylhydrazine hydrochloride (12 mmol, 1.7 g) in anhydrous ethanol (5 mL), and the mixture was stirred at room temperature for 5 min. After that, glacial acetic acid (4.8 mmol, 0.3 g) was poured, and the mixture was stirred at 90° C. for 4.5 hr. After the completion of the reaction, the produced precipitate was taken by filtration, washed with ethanol and water, and then further washed with dichloromethane to provide 2.7 g of Compound (1-H). NMR spectral data on Compound (H) thus obtained is shown in FIG. 7.

Figure 8:
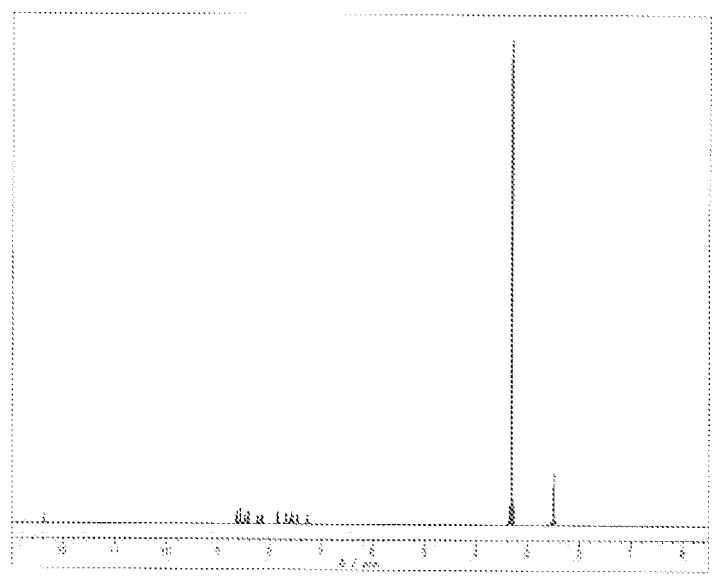
FIG. 8 is an NMR spectrum of Aromatic Heterocyclic Compound (A101).

Under a nitrogen gas atmosphere, a 300-mL recovery flask was loaded with Compound (1-H) (10.3 mmol, 3.4 g), chloranil (14.4 mmol, 3.5 g), and xylene (150 mL), and the mixture was heated to reflux for 6 hr. After the completion of the reaction, the reaction mixture was cooled to room temperature, and the precipitated solid was separated by filtration. The solid taken by filtration was washed with toluene and dichloromethane to provide 3.0 g of a compound (Compound A101). NMR spectral data on Compound (A101) thus obtained is shown in FIG. 8.

Example 2

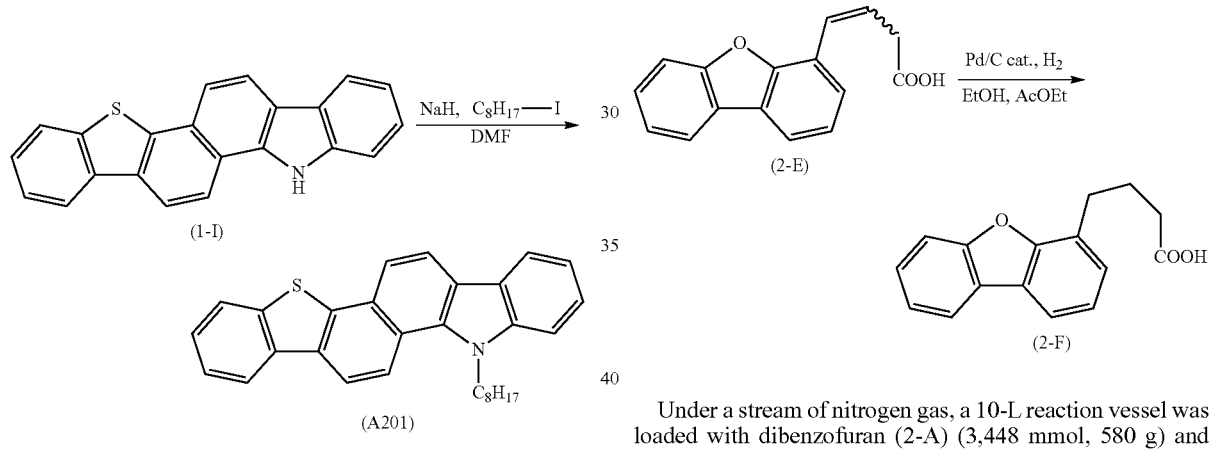

Figure 9:
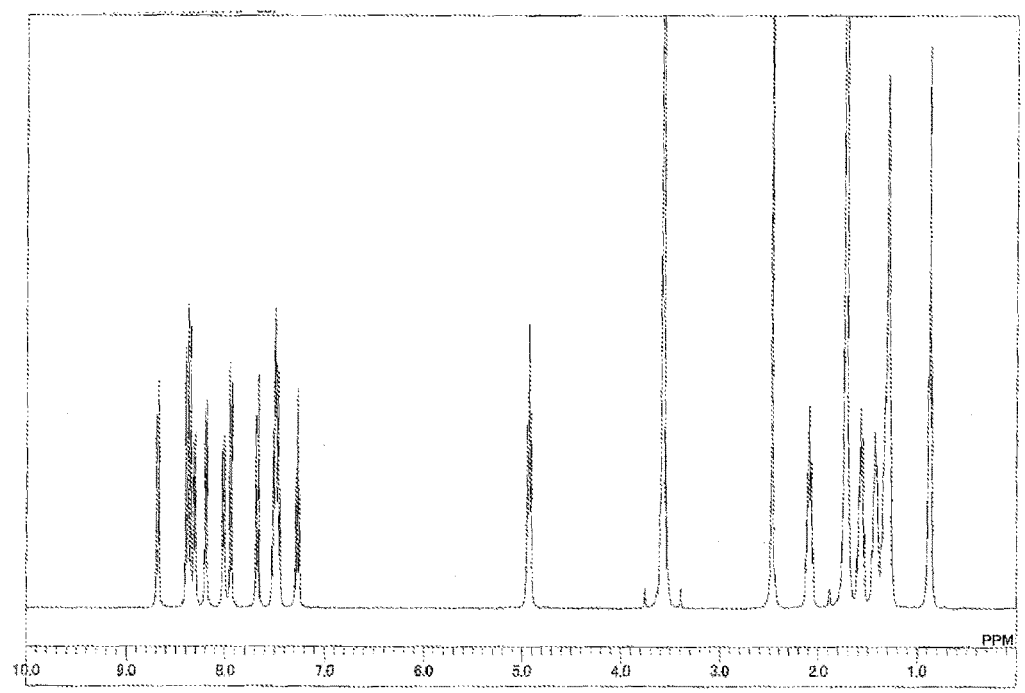
FIG. 9 is an NMR spectrum of Aromatic Heterocyclic Compound (A201).

Under a nitrogen gas atmosphere, a 200-mL three-necked flask was loaded with Compound (101) (7.7 mmol, 2.5 g), DMF (120 mL), 62% NaH (8.4 mmol, 0.34 g), and iodooctane (8.4 mmol, 2.1 g), and the mixture was stirred at room temperature overnight. A small amount of methanol was added to the reaction liquid and it was confirmed that no bubble was generated. After that, the reaction mixture was poured into water and a precipitate was separated by filtration, and washed with methanol and hexane to provide 2.4 g of Compound (201) of interest. NMR spectral data on the compound thus obtained (Compound A201) is shown in FIG. 9.

Example 3

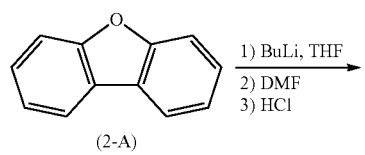

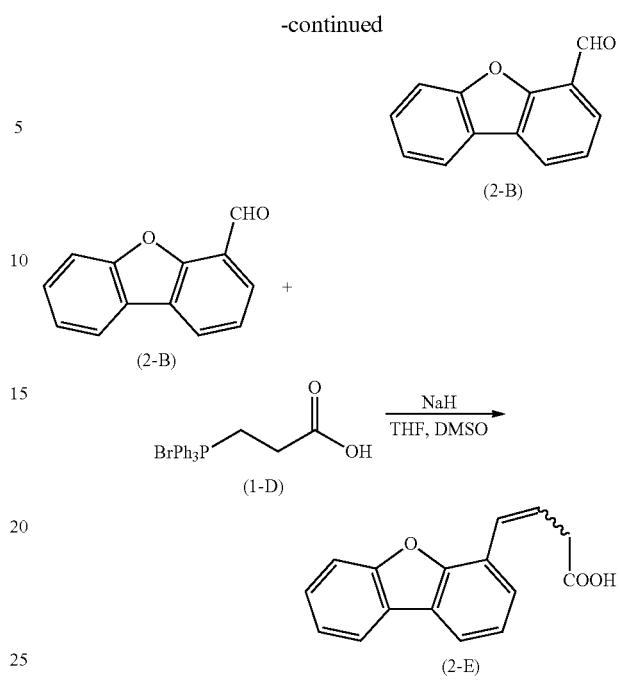

Under a stream of nitrogen gas, a 10-L reaction vessel was loaded with dibenzofuran (2-A) (3,448 mmol, 580 g) and anhydrous THF (2,260 mL), and the mixture was stirred at 0° C. for 30 min. To the mixture, a 1.6 M BuLi-heptane solution (3,414 mmol, 2,134 mL) was added dropwise. The mixture was stirred at −78° C. for 30 min, and then DMF (5,173 mmol, 401 mL) was added dropwise. The temperature of the mixture was increased to room temperature, and the stirring was continued for 2 hr thereafter. The reaction solution was poured into 6 M hydrochloric acid and adjusted to a pH of 1. The resultant was extracted with ethyl acetate, and then washed with water and brine, followed by drying over sodium sulfate, filtration, and concentration to provide 690 g of a crude product of Compound (2-B) as a yellowish white solid.

Under a stream of nitrogen gas, a 20-L reaction vessel was loaded with Compound (2-B) (3,411 mmol, 690 g), wittig-salt (1-D) (3,377 mmol, 1,402 g), anhydrous THF (6 L), and anhydrous DMSO (6 L), and the mixture was stirred at 27° C. (water bath) for 30 min. Into the mixture, sodium hydride (7,164 mmol, 286 g) was poured in small portions, and the mixture was stirred for 20 hr. The reaction liquid was poured into a 1 M hydrochloric acid aqueous solution, and the resultant was extracted with toluene and then washed with water, followed by drying over sodium sulfate, filtration, and concentration to provide 1,545 g of a crude product of Compound (2-E) as a yellow viscous liquid.

Under a stream of nitrogen gas, a 1-L recovery flask was loaded with Compound (2-E) (198 mmol, 50 g), anhydrous ethanol (280 mL), and anhydrous ethyl acetate (280 mL), and while the mixture was stirred at room temperature for 1 hr, nitrogen gas bubbling was performed. Subsequently, 10% Pd/C (31 g) was added, and while the mixture was stirred at room temperature for 1 hr, hydrogen gas bubbling was performed. After that, under a hydrogen gas atmosphere (using a 1-L balloon, 1 atm), the resultant was stirred at room temperature for 22 hr. Celite filtration was performed to remove insoluble matter, and washing was performed with ethyl acetate. After that, the resultant filtrate was concentrated to provide a crude product of Compound (2-F) as a yellow liquid.

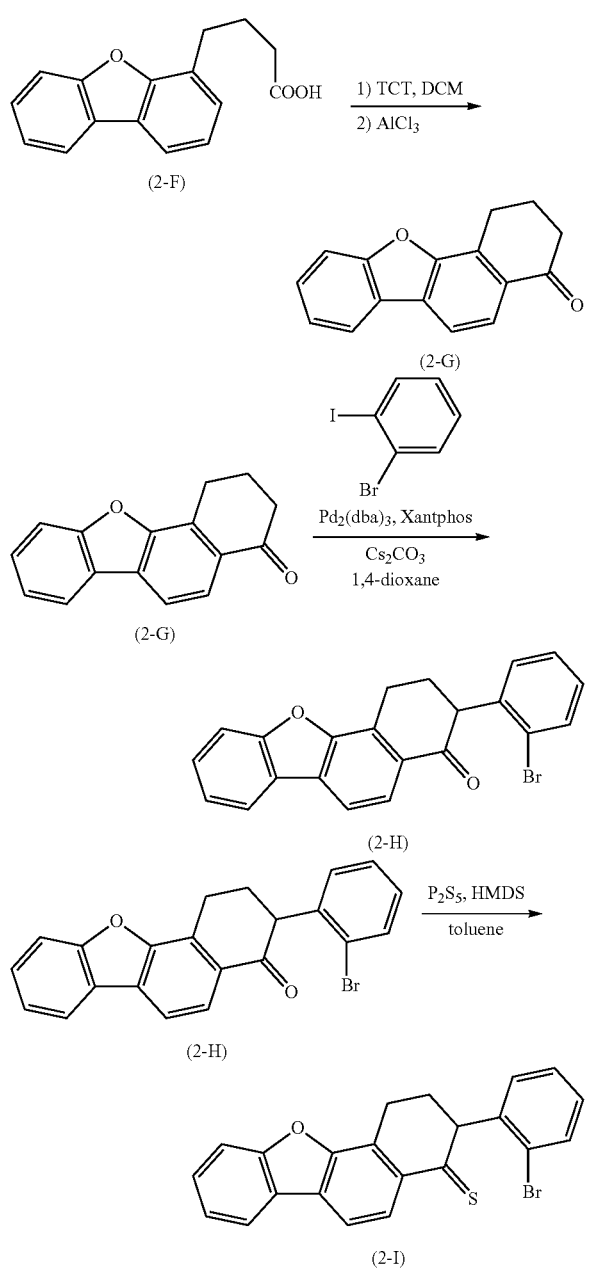

Under a stream of nitrogen gas, a 1-L recovery flask was loaded with Compound (2-F) (161 mmol, 41 g), 2,4,6-trichloro-1,3,5-triazine (322 mmol, 59.4 g), and anhydrous dichloromethane (415 mL), and the mixture was stirred at room temperature for 5 min. After that, anhydrous pyridine (484 mmol, 39.1 mL) was slowly poured at room temperature, and the mixture was stirred for 20 hr. Subsequently, aluminum chloride (322 mmol, 43 g) was slowly added at room temperature, and the mixture was stirred for 4 hr. The reaction liquid was poured into acetone cooled to 0° C. to terminate the reaction. After stirring for a while, the suspension solution was subjected to Celite filtration. Methanol was added to the filtrate, and the precipitated solid was removed by Celite filtration. The resultant filtrate was concentrated, extracted with toluene, and washed with a 1 M hydrochloric acid aqueous solution. After that, the resultant was dried over sodium sulfate, filtered, concentrated, and washed with methanol to provide 46.4 g of Compound (2-G).

Under a stream of nitrogen gas, a 300-mL recovery flask was loaded with cesium carbonate (85.8 mmol, 28.0 g), $Pd_2(dba)_3$ (0.20 mmol, 0.18 g), xantphos (0.48 mmol, 0.28 g), and 200 mL of 1,4-dioxane. Compound (2-G) (78.0 mmol, 18.4 g) and 1-bromo-2-iodobenzene (39.0 mmol, 11.0 g) were added, and the mixture was stirred at 80° C. for 24 hr. After cooling to room temperature, ethyl acetate and water were added to perform a separating operation, and the organic layer was washed with water and then dried over sodium sulfate. The resultant was filtered and then concentrated, and column chromatography was performed to provide 11.9 g of Compound (2-H).

Under a stream of nitrogen gas, a 100-mL recovery flask was loaded with Compound (2-H) (3.4 mmol, 11.9 g), diphosphorus pentasulfide (7.6 mmol, 1.7 g), and 40 mL of anhydrous toluene, and the mixture was stirred at room temperature for 10 min. After that, hexamethyldisiloxane (51.7 mmol, 8.4 g) was added, and the mixture was stirred at 90° C. for 21 hr. After cooling to room temperature, the reaction mixture was passed through a layer of silica gel and the filtrate was concentrated. The concentrate was directly used in the subsequent reaction.

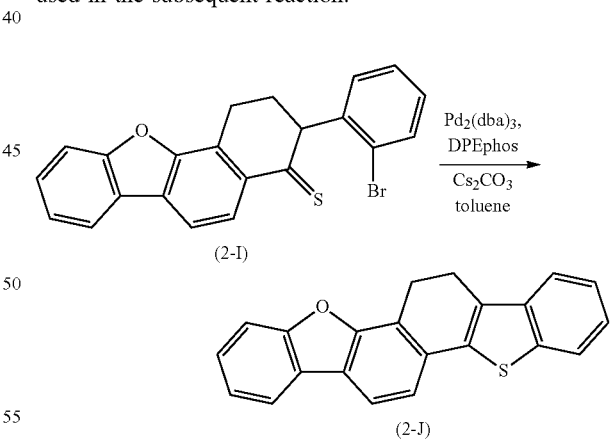

Under a stream of nitrogen gas, a 200-mL recovery flask was loaded with cesium carbonate (45.6 mmol, 14.9 g), $Pd_2(dba)_3$ (0.82 mmol, 0.75 g), 2,2'-bis(diphenylphosphino)diphenyl ether DPE (1.64 mmol, 0.88 g), Compound (2-I) (30.4 mmol, 12.4 g), and 100 mL of anhydrous toluene, and the mixture was stirred at 100° C. for 20 hr. The resultant was cooled to room temperature and then subjected to Celite filtration. The filtrate was concentrated and subjected to column chromatography to provide 7.3 g of Compound (2-J).

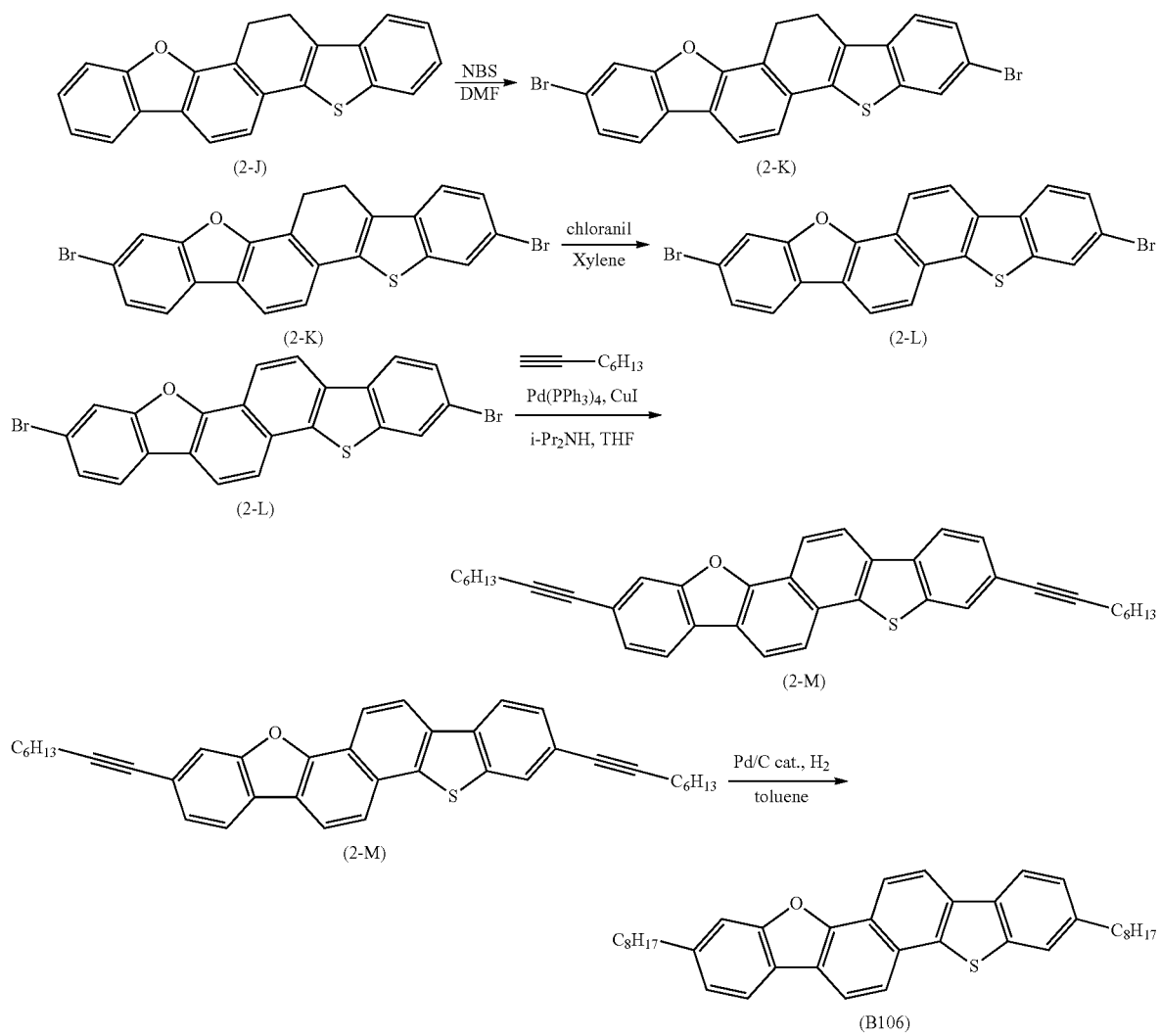

Under a stream of nitrogen gas, a 300-mL recovery flask was loaded with Compound (2-J) (22.4 mmol, 7.3 g) and anhydrous DMF (150 mL), and the mixture was stirred. While the mixture was cooled in an ice bath, NBS (45.0 mmol, 8.0 g) was added. After 2.5 hr, the ice bath was removed, and at room temperature, the mixture was stirred overnight. Methanol was added to the reaction liquid, and the precipitate was filtered and then washed with methanol to provide 9.2 g of Compound (2-K).

Under a nitrogen gas atmosphere, a 300-mL recovery flask was loaded with Compound (2-K) (15.1 mmol, 7.3 g), chloranil (22.6 mmol, 5.6 g), and xylene (300 mL), and the mixture was heated to reflux for 6 hr. After the completion of the reaction, the reaction mixture was cooled to room temperature, and the precipitated solid was separated by filtration. The solid taken by filtration was washed with toluene and dichloromethane to provide 6.8 g of Compound (2-L).

Under a nitrogen gas atmosphere, a 300-mL recovery flask was loaded with Compound (2-L) (10.4 mmol, 5.0 g), anhydrous THF (80 mL), diisopropylamine (80 mL), 1-octyne (24 mmol, 2.7 g), copper iodide (4.0 mmol, 0.75 g), tetrakistriphenylphosphinepalladium (2.1 mmol, 2.4 g), and the mixture was stirred at 85° C. for 6 hr. The reaction mixture was concentrated under reduced pressure, and the residue was dissolved in dichloromethane, washed with water, concentrated under reduced pressure, and dried. The resultant solid was washed with methanol to provide 4.7 g of Compound (2-M).

Under a stream of nitrogen gas, a 100-mL recovery flask was loaded with Compound (2-M) (8.3 mmol, 4.5 g) and anhydrous toluene (30 mL), and while the mixture was stirred at room temperature for 1 hr, nitrogen gas bubbling was performed. Subsequently, 10% Pd/C (3.0 g) was added, and while the mixture was stirred at room temperature for 1 hr, hydrogen gas bubbling was performed. After that, under a hydrogen gas atmosphere (using a 1-L balloon, 1 atm), the resultant was stirred at room temperature for 22 hr. Celite filtration was performed to remove insoluble matter, and the resultant filtrate was concentrated and then subjected to column chromatography to provide Compound (B106). FDMS: m/z 548

Example 4

The characteristics of the organic semiconductor material of the present invention were evaluated by producing an organic field-effect transistor having a construction illustrated in FIG. 2. First, a silicon wafer (n-doped) having a thermally grown silicon oxide layer having a thickness of about 300 nm was washed with a solution of sulfuric acid in hydrogen peroxide water and boiled with isopropyl alcohol, followed by drying. A solution (2 wt %) of Compound (A201) in chlorobenzene was formed into a film on the resultant silicon wafer (n-doped) having a thermally grown silicon oxide layer by a spin coating method, followed by heat treatment at 80° C. to form a thin film of Compound (A201) having a thickness of 50 nm. Further, gold was deposited onto the surface of the film using a mask to form a source electrode and a drain electrode. The source electrode and the drain electrode had a width of 100 μm and a thickness of 200 nm, and an organic field-effect transistor having a channel width of W=2 mm and a channel length of L=50 μm was produced.

A voltage of −100 V was applied between the source electrode and drain electrode of the resultant organic field-effect transistor, and then a gate voltage was changed in the range of from −20 V to −100 V to determine its voltage-current curve at a temperature of 25° C., followed by the evaluation of the organic field-effect transistor for its transistor characteristics. A field-effect mobility (μ) was calculated with the following equation (I) representing a drain current $I_d$.

$$I_d = (W/2L)\mu C_i (V_g - V_t)^2 \quad (I)$$

In the equation (I), L represents the channel length and W represents the channel width. In addition, $C_i$ represents the capacity of an insulating layer per unit area, $V_g$ represents the gate voltage, and $V_t$ represents a threshold voltage. The calculated field-effect mobility was found to be $8.0 \times 10^{-1}$ cm²/Vs.

Example 5

Compounds (A101), (A216), (A218), (A221), (A226), (A501), (A702), and (A805) were synthesized in the same manner as Compounds (A201) and (B106). An organic field-effect transistor was produced by performing the same operations as those of Example 4 except that a solution (2 wt %) of Compound (A101), (A216), (A218), (A221), (A226), (A501), (A702), or (A805) in chlorobenzene was used instead of the solution (2 wt %) of Compound (A201) in chlorobenzene, and the resultant device was evaluated for its transistor characteristic in the same manner as in Example 4. The results are shown in Table 1.

TABLE 1

| Compound | Field-effect mobility (cm²/Vs) |
|---|---|
| A101 | $6.3 \times 10^{-1}$ |
| A216 | $9.3 \times 10^{-1}$ |
| A218 | $7.5 \times 10^{-1}$ |
| A221 | $8.6 \times 10^{-1}$ |
| A226 | $3.2 \times 10^{-1}$ |
| A501 | 1.2 |
| A702 | $4.8 \times 10^{-1}$ |
| A802 | $7.5 \times 10^{-1}$ |

Example 6

An organic field-effect transistor was produced by performing the same operations as those of Example 4 except that a solution (2 wt %) of Compounds (B101), (B106), (B147), (B151), (B166), or (B172) in chlorobenzene was used instead of the solution (2 wt %) of Compound (A201) in chlorobenzene. The resultant device was evaluated for its transistor characteristics in the same manner as in Example 4. The results are shown in Table 2.

TABLE 2

| Compound | Field-effect mobility (cm²/Vs) |
|---|---|
| B101 | $6.7 \times 10^{-1}$ |
| B106 | 2.3 |
| B147 | $7.8 \times 10^{-1}$ |
| B151 | $9.6 \times 10^{-1}$ |
| B166 | $4.3 \times 10^{-1}$ |
| B172 | 1.8 |

Comparative Example 1

An organic field-effect transistor was produced by performing the same operations as those of Example 4 except that a solution (2 wt %) of Compound (H1) below in chlorobenzene was used instead of the solution (2 wt %) of Compound (A201) in chlorobenzene. The resultant device was evaluated for its transistor characteristics in the same manner as in Example 4 and found to have a field-effect mobility of $1.1 \times 10^{-2}$ cm²/Vs.

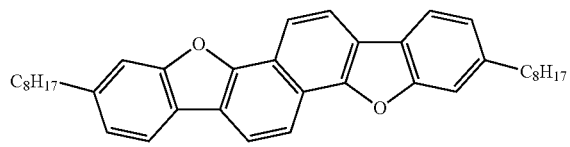

(H1)

On the basis of the comparison of Examples to Comparative Example 1, it was revealed that the organic field-effect transistors each using the aromatic heterocyclic compound represented by the formula (1) had high characteristics.

REFERENCE SIGNS LIST

1; substrate, 2; gate electrode, 3; insulating film layer, 4; organic semiconductor, 5; source electrode, 6; drain electrode, 7; substrate, 8; positive electrode, 9; organic semiconductor layer, 9-a; electron-donating organic semiconductor layer, 9-b; electron-accepting organic semiconductor layer, 10; negative electrode.

The invention claimed is:
1. An aromatic heterocyclic compound, which is represented by the following general formula (1):

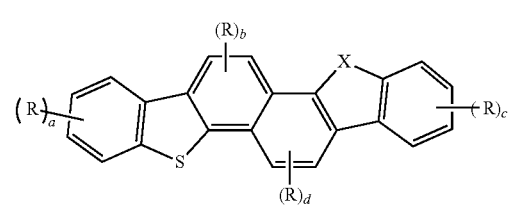

(1)

wherein:
X represents an oxygen atom or N—R;

R's each independently represent a hydrogen atom or a monovalent substituent; and at least one of the R's represents a monovalent group selected from the group consisting of: a halogen atom; a hydroxy group; a substituted or unsubstituted aliphatic hydrocarbon group having 1 to 30 carbon atoms; a substituted or unsubstituted alkoxy group having 1 to 30 carbon atoms; an amino group; a substituted amino group; a thiol group; a substituted sulfonyl group; a cyano group; a substituted or unsubstituted aromatic hydrocarbon group having 6 to 48 carbon atoms; a substituted or unsubstituted aromatic heterocyclic group having 2 to 48 carbon atoms; a substituted or unsubstituted aromatic hydrocarbon-substituted alkynyl group having 8 to 50 carbon atoms; a substituted or unsubstituted aromatic heterocycle-substituted alkynyl group having 4 to 50 carbon atoms; a substituted or unsubstituted aromatic hydrocarbon-substituted alkenyl group having 8 to 50 carbon atoms; a substituted or unsubstituted aromatic heterocycle-substituted alkenyl group having 4 to 50 carbon atoms; a substituted or unsubstituted alkylsilylalkynyl group having 5 to 30 carbon atoms; a substituted or unsubstituted alkylsilyl group having 3 to 30 carbon atoms; a substituted or unsubstituted siloxane group having 1 to 30 silicon atoms; a substituted or unsubstituted siloxane alkyl group having 1 to 30 silicon atoms; and a substituted or unsubstituted polysilane group having 1 to 30 silicon atoms;

a and c each represent an integer of from 1 to 4; and b and d each represent an integer of 1 or 2.

2. The aromatic heterocyclic compound according to claim 1, wherein at least one of the R's represents a monovalent substituent of: a halogen atom; a substituted or unsubstituted aliphatic hydrocarbon group having 1 to 12 carbon atoms; a substituted or unsubstituted alkoxy group having 1 to 12 carbon atoms; a thiol group; a substituted sulfonyl group having 1 to 12 carbon atoms; a cyano group; a substituted or unsubstituted aromatic hydrocarbon group having 6 to 24 carbon atoms; a substituted or unsubstituted aromatic heterocyclic group having 3 to 18 carbon atoms; a substituted or unsubstituted aromatic hydrocarbon-substituted alkynyl group having 8 to 26 carbon atoms; a substituted or unsubstituted aromatic heterocycle-substituted alkynyl group having 6 to 26 carbon atoms; a substituted or unsubstituted aromatic hydrocarbon-substituted alkenyl group having 8 to 26 carbon atoms; a substituted or unsubstituted aromatic heterocycle-substituted alkenyl group having 6 to 26 carbon atoms; a substituted or unsubstituted alkylsilylalkynyl group having 5 to 20 carbon atoms; a substituted or unsubstituted alkylsilyl group having 3 to 20 carbon atoms; a substituted or unsubstituted siloxane group having 1 to 20 silicon atoms; a substituted or unsubstituted siloxane alkyl group having 1 to 20 silicon atoms; or a substituted or unsubstituted polysilane group having 1 to 20 silicon atoms.

3. The aromatic heterocyclic compound according to claim 1, wherein the aromatic heterocyclic compound is represented by the following general formula (2):

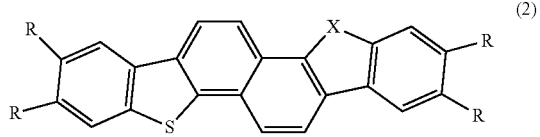

(2)

wherein, X and R have the same meanings as X and R in the general formula (1), respectively.

4. The aromatic heterocyclic compound according to claim 1, wherein X represents N—R.

* * * * *